US012369996B2

(12) United States Patent
Sankai

(10) Patent No.: US 12,369,996 B2
(45) Date of Patent: Jul. 29, 2025

(54) INTERACTIVE INFORMATION TRANSFER SYSTEM, INTERACTIVE INFORMATION TRANSFER METHOD, AND INFORMATION TRANSFER SYSTEM

(71) Applicants: CYBERDYNE INC., Tsukuba (JP); UNIVERSITY OF TSUKUBA, Tsukuba (JP)

(72) Inventor: Yoshiyuki Sankai, Tsukuba (JP)

(73) Assignees: CYBERDYNE INC., Ibaraki (JP); UNIVERSITY OF TSUKUBA, Ibaraki (JP)

( * ) Notice: Subject to any disclaimer, the term of this patent is extended or adjusted under 35 U.S.C. 154(b) by 977 days.

(21) Appl. No.: 17/289,372

(22) PCT Filed: Oct. 30, 2019

(86) PCT No.: PCT/JP2019/042698
§ 371 (c)(1),
(2) Date: Apr. 28, 2021

(87) PCT Pub. No.: WO2020/090943
PCT Pub. Date: May 7, 2020

(65) Prior Publication Data
US 2021/0393343 A1  Dec. 23, 2021

(30) Foreign Application Priority Data

Oct. 30, 2018 (JP) .................. 2018-204539
Dec. 28, 2018 (JP) .................. 2018-248614
Mar. 5, 2019 (JP) .................. 2019-039641

(51) Int. Cl.
*A61B 34/30* (2016.01)
*A61B 34/00* (2016.01)
*A61B 90/00* (2016.01)

(52) U.S. Cl.
CPC .............. *A61B 34/30* (2016.02); *A61B 34/74* (2016.02); *A61B 34/76* (2016.02); *A61B 90/37* (2016.02); *A61B 2034/741* (2016.02)

(58) Field of Classification Search
CPC ......... A61B 34/30; A61B 34/74; A61B 34/76; A61B 90/37; A61B 2034/741
See application file for complete search history.

(56) References Cited

U.S. PATENT DOCUMENTS 5,354,162 A * 10/1994 Burdea .................. G06F 3/016
  414/4
2009/0177452 A1 * 7/2009 Ullrich .................. G06F 3/014
  703/11

(Continued)

FOREIGN PATENT DOCUMENTS

JP  2000-125024 A  4/2000
JP  2004-117779 A  4/2004

(Continued)

OTHER PUBLICATIONS

Extended European Search Report issued on Jun. 15, 2022 for European Patent Application No. 19880454.4.

(Continued)

*Primary Examiner* — Dmitry Suhol
*Assistant Examiner* — Alyssa N Brandley
(74) *Attorney, Agent, or Firm* — Volpe Koenig

(57) ABSTRACT

As an expert gives instructions to cause movements of their own hands transferred directly as tactile force sense while perceiving surrounding information of a collaborator on a real-time basis and watching the collaborator's line-of-sight end and movements of the collaborator's hands, the collaborator indirectly receives the instructions of the expert's manual skills, which are the expert's tacit knowledge, on a real-time basis while sharing realistic sensations with the (Continued)

expert who is at a remote location when the collaborator performs an act of working with their own hands.

27 Claims, 34 Drawing Sheets

(56) References Cited

U.S. PATENT DOCUMENTS

| | | | |
|---|---|---|---|
| 2012/0045742 A1 | 2/2012 | Meglan et al. | |
| 2012/0253360 A1* | 10/2012 | White | A61B 34/35 606/130 |
| 2014/0220527 A1 | 8/2014 | Li et al. | |
| 2014/0287393 A1* | 9/2014 | Kumar | G09B 5/02 434/262 |
| 2015/0248847 A1* | 9/2015 | Wang | A61B 34/37 434/262 |
| 2016/0187974 A1 | 6/2016 | Mallinson | |
| 2016/0234461 A1* | 8/2016 | Mizuhara | H04N 7/147 |
| 2016/0314717 A1* | 10/2016 | Grubbs | G09B 23/306 |
| 2018/0185110 A1* | 7/2018 | Kumar | G09B 23/28 |
| 2018/0250086 A1 | 9/2018 | Grubbs | |

FOREIGN PATENT DOCUMENTS

| | | |
|---|---|---|
| JP | 2005-287656 A | 10/2005 |
| JP | 2006-259926 A | 9/2006 |
| JP | 2014-004655 A | 1/2014 |
| JP | 2014-004656 A | 1/2014 |
| JP | 2016-140720 A | 8/2016 |
| JP | 2017-191490 A | 10/2017 |
| JP | 2018-500674 A | 1/2018 |
| JP | 2019-029203 A | 2/2019 |
| JP | 2019-164216 A | 9/2019 |
| JP | 2019-217557 A | 12/2019 |

OTHER PUBLICATIONS

International Search Report, PCT/JP2019/042698, Jan. 28, 2020, 3 pgs.

* cited by examiner

FIG. 1
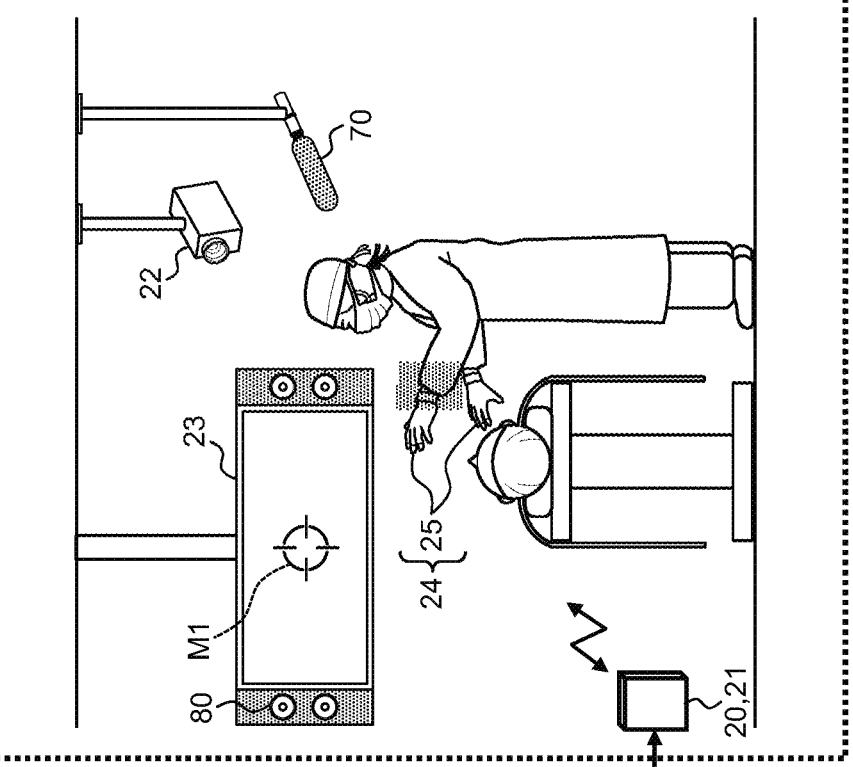
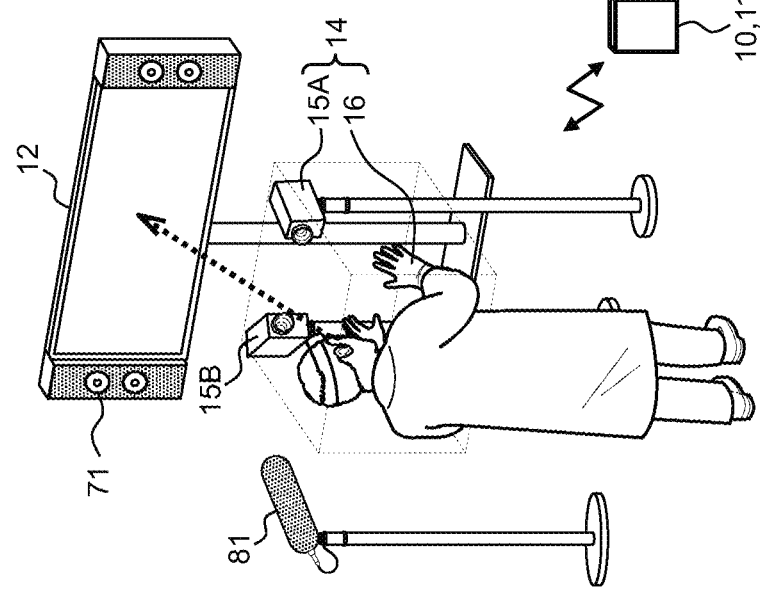

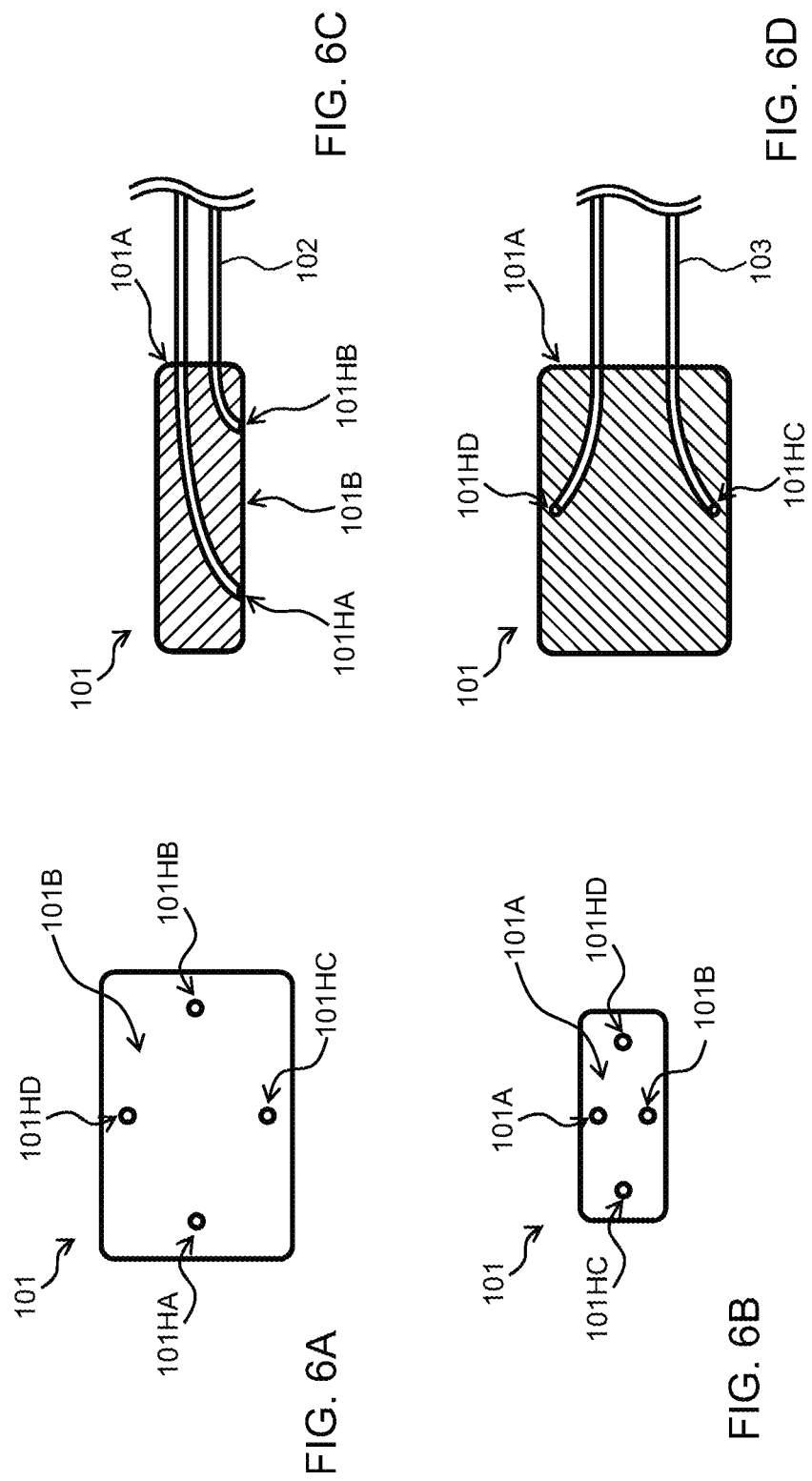

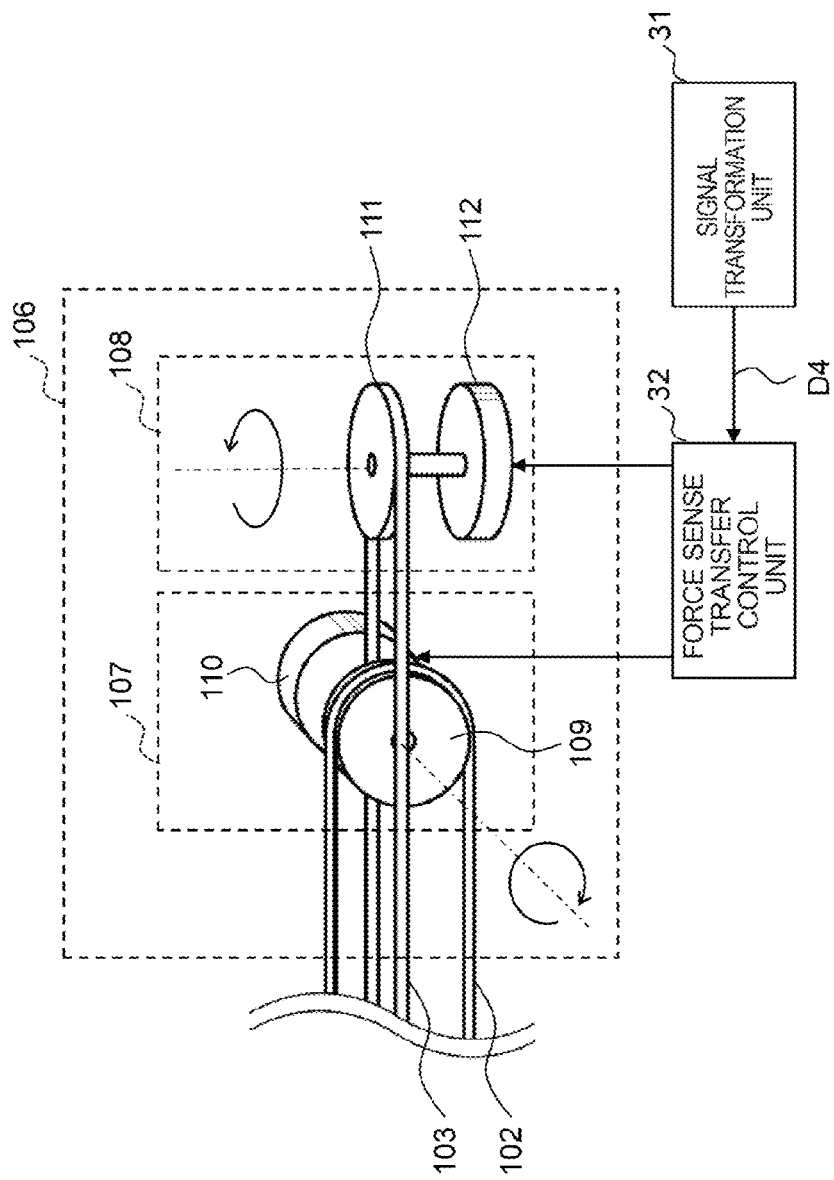

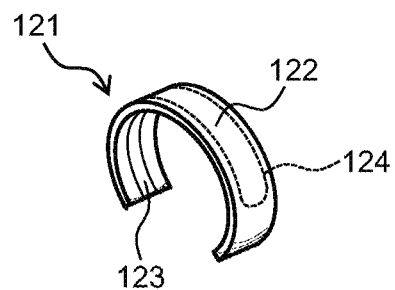
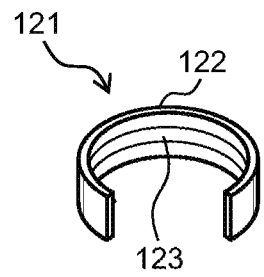
FIG. 8A          FIG. 8B
FIG. 9
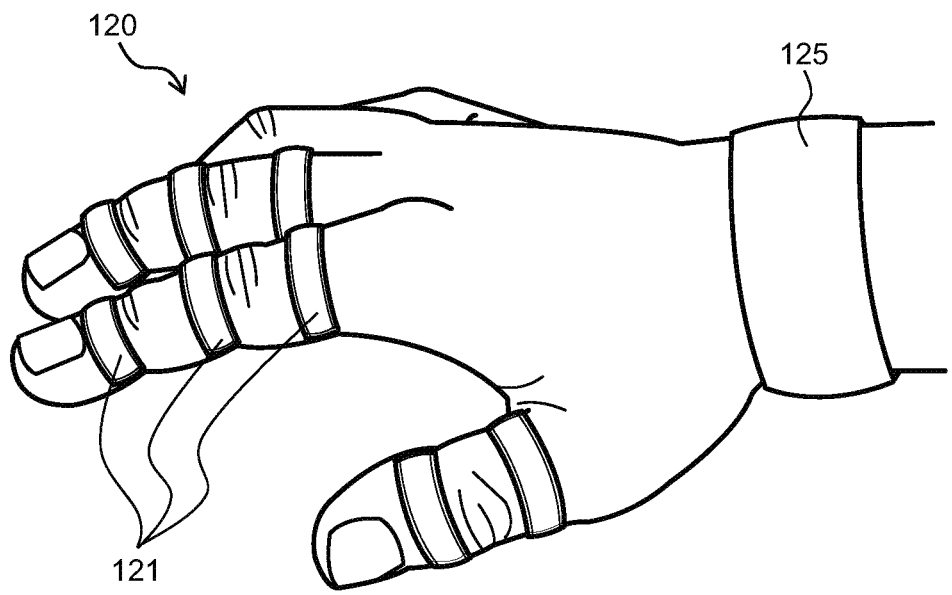

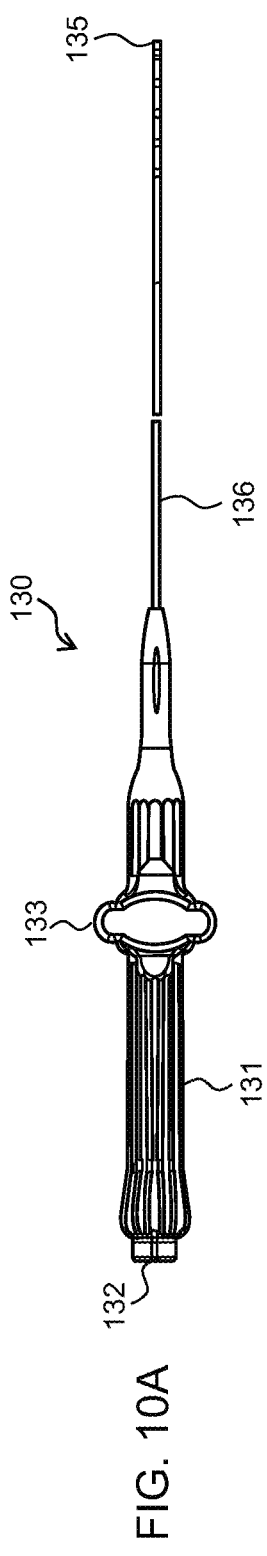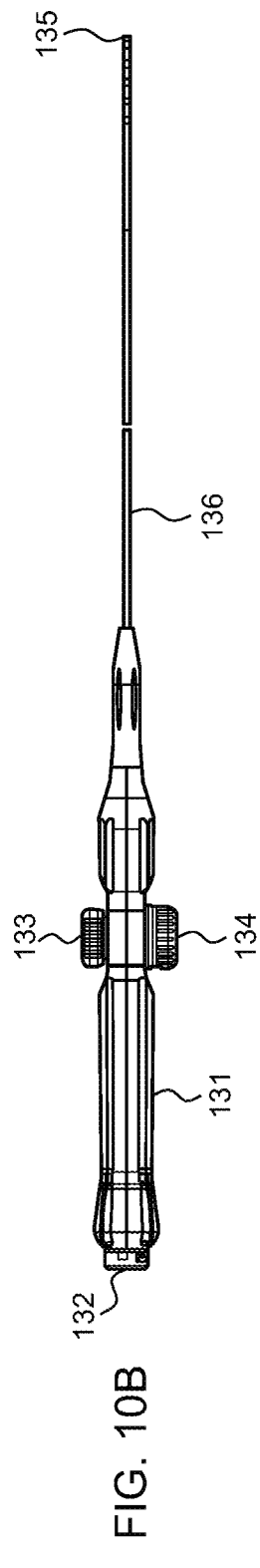
FIG. 10

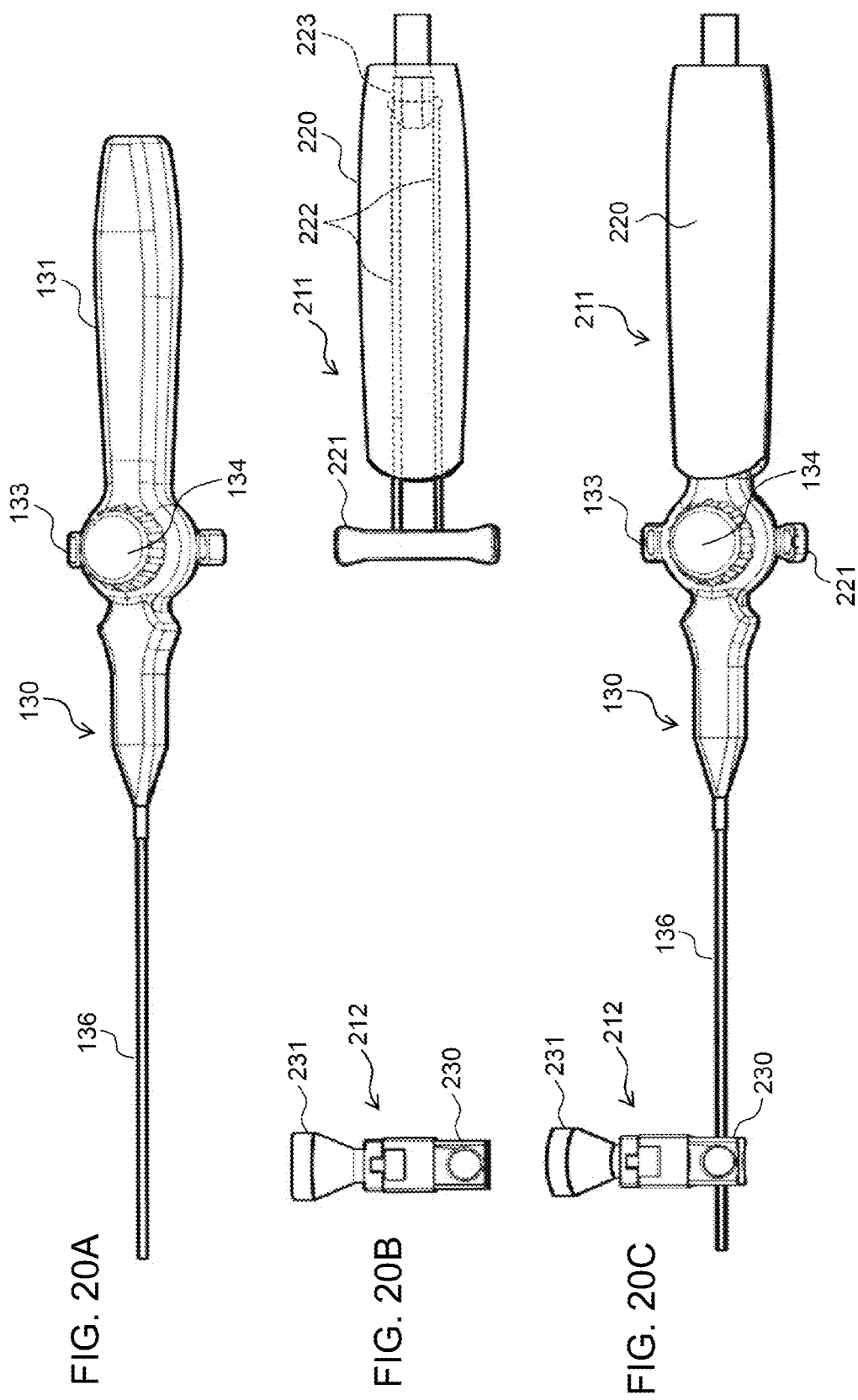

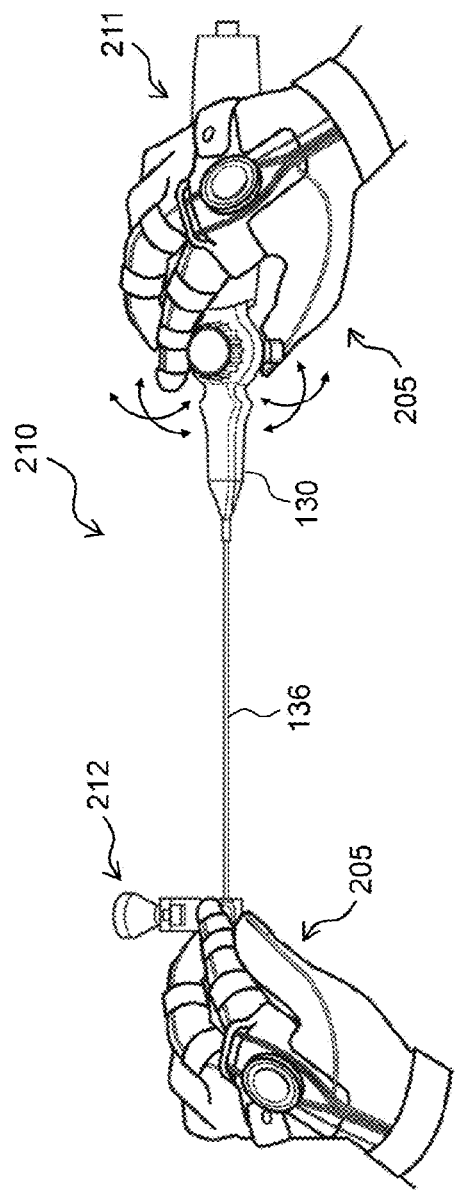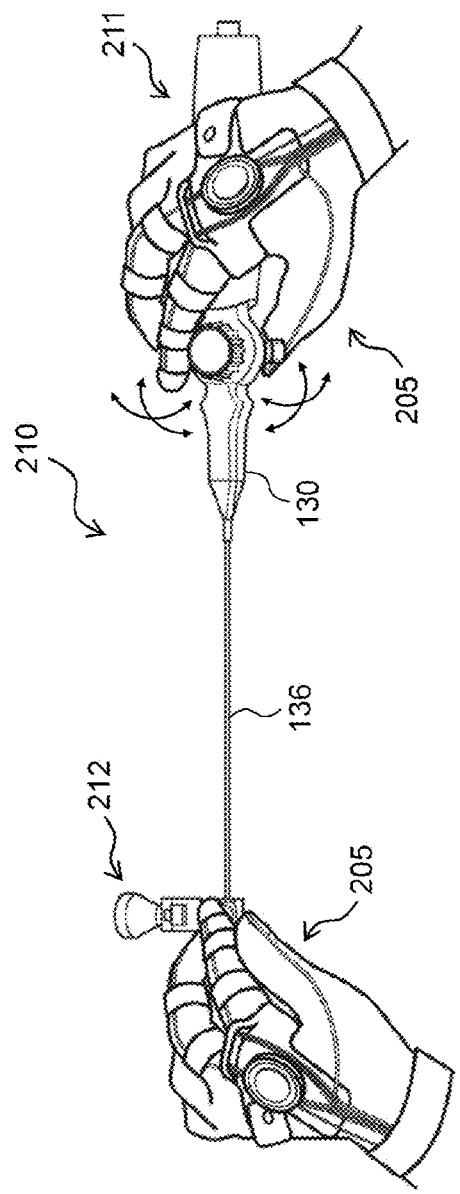
FIG. 23A
FIG. 23B

INTERACTIVE INFORMATION TRANSFER SYSTEM, INTERACTIVE INFORMATION TRANSFER METHOD, AND INFORMATION TRANSFER SYSTEM

TECHNICAL FIELD

The present invention relates to a technology for an expert to instruct an collaborator in their skills regarding specific work while making the expert and the collaborator mutually exchange information via a network.

BACKGROUND ART

Currently, a treatment to perform cauterization by using a catheter at an affected part in an abnormal heart, which causes arrhythmia, to recover a normal rhythm (catheter ablation treatment) is widely performed as an arrhythmia treatment. Particularly at core hospitals, experienced doctors who have proficient skills capable of performing the catheter ablation treatment appropriately and frequently take central role to provide the safe and secure treatment.

This catheter ablation treatment is to insert a catheter, which is a long tube with a diameter of approximately 2 mm, from a vein at a paten's leg joint or neck under local anesthesia through blood vessels into the heart, find a site which caused the arrhythmia while measuring an electrocardiogram via an electrode at a tip end of the catheter, and then cauterize cardiac tissues by applying a high-frequency current from the tip end of the catheter to the site to be treated.

Accordingly, the catheter ablation treatment causes less physical burdens than a surgical operation to the patient; however, in order to perform the catheter ablation treatment speedily and safely, it is necessary for a person who performs the treatment to receive instructions from an experienced doctor(s) about their excellent skills and gain experience by themselves by treating many patients.

However, there are many local hospitals where there is no experienced doctor having the proficient skills; and shortage of the experienced doctor has become a very serious problem for the patients who live in local areas.

In consideration of the above-described circumstances, there has recently started an approach to enable an medical instructor who is an experience doctor to be involved remotely in a surgical operation conducted in a local hospital by connecting a remote location and a core hospital via a dedicated line and giving aural instructions while watching images on a real-time basis. As an example case, an approach regarding a remote treatment support for the catheter ablation treatment via images with the remote location has been started in Ibaraki Prefecture since 2017.

As a conventional technology document, there is proposed a remote work support communication apparatus which gives instructions via video sounds by using a communication terminal when an expert causes a collaborator at a remote location to perform work via a network (see PTL 1).

With this remote work support communication apparatus, the expert can observe the state of the collaborator and a work object in detail by turning a camera in a direction where the expert should see, and at the same time, can give instructions by pointing a laser pointer to the work object to which the expert wants the collaborator to focus their attention.

Furthermore, there is proposed an acupuncture treatment training system designed to store operation content by a trainer as force-tactile sense information and make it possible to perform trainings of an acupuncture treatment to stimulate virtual acupuncture points with a virtual needle body by making use of the force-tactile sense (see PTL 2).

This acupuncture treatment training system can enhance the acupuncture treatment technique by making it possible to judge whether an angle, speed, a degree of strength, and depth of the needle body to be inserted into the acupuncture points are appropriate or not.

Furthermore, the inventor of the present invention has also proposed: a master-slave-type manipulation system for improving operability of the manipulation system by dynamically changing impedance of a robot arm by using a bioelectric potential information signal of an operator (see PTL 3); and, in addition to the above, a master-slave-type manipulation system with improved operability by assisting the operation with visual information (see PTL 4).

CITATION LIST

Patent Literature

PTL 1: Japanese Patent Application Laid-Open (Kokai) Publication No. 2000-125024
PTL 2: Japanese Unexamined Patent Application Publication (Translation of PCT Application) No. 2005-287656
PTL 3: Japanese Patent Application Laid-Open (Kokai) Publication No. 2014-4655
PTL 4: Japanese Patent Application Laid-Open (Kokai) Publication No. 2014-4656

SUMMARY OF THE INVENTION

Problems to be Solved by the Invention

Meanwhile, under the circumstances like the surgical operation for the catheter ablation treatment where rapidity and accuracy are required, there is a demand for a very delicate level of manual skills which are to be transferred from the expert to the collaborator, while it is necessary for the collaborator to feel the manual skills delicately as a force sense on a real-time basis.

Moreover, there is fear that the expert at the remote location may give instructions to the collaborator according to an erroneous judgment of the situation unless the expert perceives not only the collaborator's line-of-sight end, but also the ambient environment as much as possible.

For example, when a site to puncture the catheter into a patient's thigh part is to be accurately identified, the femoral artery branches off at a bone cortex inferior margin level of the caput femoris and, therefore, it is necessary to puncture the catheter by checking the position of the caput femoris under fluoroscopic guidance. Furthermore, regarding the manual puncture skills, there is also a case, as a method for not piercing through a rear wall of a blood vessel, where: the puncture is pushed forward while slightly performing suction with a syringe; a guide wire is inserted at a point where the blood flows back; and then the catheter is secured at a position inside the blood vessel.

In order to transfer such delicate and highly-accurate manual skills from the expert to the collaborator, it is very difficult to sufficiently satisfy the accuracy in transferring the manual skills for practical use merely by combining the technical content described in PTL 1 to PTL 4 above.

Specifically speaking, the expert must perceive not only simply the collaborator's line of sight, but also the collaborator's current work state and its ambient environment with high accuracy in order to instruct the collaborator in their manual skills on a real-time basis. At the same time, the collaborator must have the expert accurately recognize the collaborator's current work state in order to intuitively accurately understand the expert's intention.

Accordingly, even just the treatment support via images and sounds is expected as a useful method for the remote treatment support; however, the transfer and transmission of the skills, that is, how a proficient doctor should handle the catheter and proceed with the treatment are still in an undeveloped state. It is a serious problem that an experienced doctor(s) or a medical instructor(s) cannot perform an appropriate treatment by cooperating with a doctor/medical team at a remote location and instructing the doctor/medical team in their skills such as their manual treatment skills.

The present invention was devised in consideration of the above-described circumstances and proposes an interactive information transfer system, interactive information transfer method, and information transfer system that enable a collaborator, when performing acts of their own manual work, to share realistic sensations with an expert at a remote location and indirectly receive instructions of the expert's manual skills, which are the expert's tacit knowledge, on a real-time basis.

Means to Solve the Problems

In order to solve the above-described problems, provided according to the present invention is an interactive information transfer system for an expert to instruct a collaborator in their skills regarding specific work while making the expert and the collaborator mutually exchange information via a network, wherein an instructing-side information processing apparatus provided on the expert's side includes: an instructing-side communication unit that receives a video, which is mainly targeted at an object handled by the collaborator, via the network; an instructing-side video display unit that displays the video of the object which is received by the instructing-side communication unit; a line-of-sight detection unit that detects a position of a line-of-sight extended end of the expert within a display range of the instructing-side video display unit as line-of-sight position data; and a movement detection unit that detects fingers' action data corresponding to respective three-dimensional directional movements by setting respective fingertips of the expert as endpoints, wherein the instructing-side communication unit transmits the line-of-sight position data and the fingers' action data on a real-time basis via the network; and wherein a collaborating-side information processing apparatus provided on the collaborator's side includes: a collaborating-side communication unit that receives the line-of-sight position data and the fingers' action data which are transmitted from the instructing-side communication unit; an object imaging unit that captures a video mainly targeted at the object; a collaborating-side video display unit that displays the video captured by the object imaging unit and, at the same time, marks and displays the position of the line-of-sight extended end of the expert on the basis of the line-of-sight position data received by the collaborating-side communication unit within a display range; and a force displacement transfer unit that includes end effectors respectively mounted on respective fingertips of the collaborator and gives a force sense to prompt three-dimensional actions to each of the fingers while transferring three-dimensional directional movements based on the fingers' action data received by the collaborating-side communication unit with respect to each of the end effectors, wherein the collaborating-side communication unit transmits the video captured by the object imaging unit and physical feedback information of the respective end effectors, which is a transfer result of the force displacement transfer unit, to the instructing-side communication unit for the instructing-side information processing apparatus via the network.

Accordingly, the expert transfers the position of their line-of-sight end to the collaborator on a real-time basis while visually watching the same video as the video mainly targeted at the object handled by the collaborator; and, at the same time, the expert gives instructions to transfer the three-dimensional directional movements of their own fingertips to the respective fingers of the collaborator as the force sense on a real-time basis, while the transfer result is fed back to the expert.

As a result, when the collaborator performs their own work, the collaborator can indirectly receive the expert's instructions of the manual skills, that is, the expert's tacit knowledge on a real-time basis, while sharing realistic sensations with the expert at the remote location. Furthermore, the expert can perceive gaps between their own instruction content and the collaborator's response content on a real-time basis by perceiving the result of the force sense transfer to the collaborator in the feedback manner.

Moreover, according to the present invention, the movement detection unit for the instructing-side information processing apparatus includes: a three-dimensional imaging unit that captures videos of the respective endpoints of the expert from a plurality of different directions; and an action arithmetic operation unit that detects the fingers' action data according to the three-dimensional directional movements of the respective fingertips of the expert by arithmetically operating three-dimensional coordinates centered at a specified position of a front side of the expert with respect to the respective endpoints from a video capturing result by the three-dimensional imaging unit. As a result, the movements of the expert's fingertips can be detected with high accuracy.

Furthermore, according to the present invention, the force displacement transfer unit for the collaborating-side information processing apparatus includes: a force sense transfer drive unit that drives each end effector to guide the end effector to a direction to expand or bend each relevant finger, a direction to adduct or abduct the finger, and a direction to rotate the finger; a signal transformation unit that breaks down the three-dimensional directional movements of each endpoint of the expert into a position, speed, acceleration, angular velocity, force, and moment of the endpoint on the basis of the fingers' action data received by the collaborating-side communication unit, and transforms each of them to action element data; and a force sense transfer control unit that controls the force sense transfer drive unit so that the position, speed, acceleration, angular velocity, force, and moment of each end effector in the respective directions become in a state based on the action element data obtained from the signal transformation unit.

As a result, by driving the end effector mounted on each finger of the collaborator in conformity with the three-dimensional directional movements of the endpoints which are the expert's respective fingertips, the force sense can be imparted to guide the relevant each finger of the collaborator to the direction to expand or bend the finger, the direction to adduct or abduct the finger, and the direction to rotate the finger.

Furthermore, according to the present invention, the force displacement transfer unit for the collaborating-side information processing apparatus includes a transfer ratio setting unit that variably sets a transfer ratio of the three-dimensional directional movements based on the fingers' action data with respect to each end effector in accordance with operation by the collaborator; and wherein the signal processing unit transforms the fingers' action data to the action element data by adjusting the fingers' action data to the transfer ratio which is set by the transfer ratio setting unit.

As a result, if the collaborator judges that their own work would be negatively affected, it is possible to increase or decrease the level of transferring the three-dimensional directional movements of the expert's respective fingertips by adjusting the transfer ratio by themselves. Specifically speaking, whether the expert should be prioritized or the collaborator should be prioritized can be adjusted by changing the transfer ratio, so that the collaborator can perform the work according to their own proficiency level.

Furthermore, according to the present invention, each end effector includes a fingertip back retaining part which enters into contact with and is retained at a fingertip back part of the collaborator, and a pair of a first linear member and a second linear member which are respectively pulled out of a top, bottom, right, and left of an end of the fingertip back retaining part; wherein the force sense transfer drive unit includes: an expansion/bending drive unit that drives the first linear member to guide the fingertip to a direction to expand or bend the fingertip by moving the first linear member in a direction to push out or pulled in the first linear member; and an adduction/abduction drive unit that drives the second linear member to guide the fingertip in a direction to adduct or abduct the fingertip by moving the second linear member to right and left directions; and wherein the force sense transfer control unit controls the expansion/bending drive unit and the adduction/abduction drive unit so that the expansion/bending drive unit and the adduction/abduction drive unit respectively become in a state based on the action element data.

As a result, regarding the end effector mounted on each finger by the collaborator, the movements of the fingers by the expert's work can be transferred at a delicate level to the collaborator. Moreover, since the end effector to be mounted on the collaborator's each finger is configured to not shield a finger pad of the relevant finger, the collaborator can perform their own work while touching the object directly with their respective fingers.

Furthermore, according to the present invention, each end effector includes a wound rotation unit whose contact face in contact with the finger is wound, in a manner freely rotatable in a rotating direction, with the contact face positioned at a center of the back part of the finger at one or more positions at least one of between the fingertip and a first joint, between the first joint and a second joint, and between the second joint and a third joint; wherein the force sense transfer drive unit includes a rotation drive unit that drives the contact face of the wound rotation unit in contact with the finger to guide the finger in the rotating direction by rotating the contact face of the wound rotation unit according to an electromagnetic force or piezoelectric thrust; and wherein the force sense transfer control unit controls the rotation drive unit so that the rotation drive unit becomes in a state based on the action element data.

As a result, regarding the end effector to be mounted on each finger by the collaborator, if not only the actions in the expanding or bending direction or the adduction or abduction direction, but also a twisting action is performed by using the fingertips, the movements of the fingers by the expert's work can be further transferred at a delicate level to the collaborator by transferring the force sense so as to guide the relevant fingers in the rotating direction. Moreover, since the end effector to be mounted on each finger of the collaborator is configured to not shield a finger pad of the relevant finger, the collaborator can perform their own work while touching the object directly with their respective fingers.

Furthermore, according to the present invention, each end effector includes a single vibrating element or a plurality of vibrating elements which are mounted at a center of the fingertip back part of the collaborator and are capable of vibrating with directivity in three-dimensional directions; wherein the force sense transfer drive unit includes a vibration drive unit that drives the vibrating element or the vibrating elements to guide the vibrating element or the vibrating elements respectively in the direction to expand or bend the finger, the direction to adduct or abduct the finger, and the direction to rotate the finger; and wherein the force sense transfer control unit controls the vibration drive unit so that the vibration drive unit becomes in a state based on the action element data.

As a result, regarding the end effector mounted on each finger by the collaborator, the movements of the fingers by the expert's work can be transferred at a delicate level to the collaborator. Moreover, since the end effector to be mounted on each finger of the collaborator is configured to not shield a finger pad of the relevant finger, the collaborator can perform their own work while touching the object directly with their respective fingers.

Furthermore, according to the present invention, each end effector includes a single light emitter or a plurality of light emitters which are mounted at a center of the fingertip back part of the collaborator and are capable of emitting light with directivity in three-dimensional directions; wherein the force sense transfer drive unit includes a light-emitting drive unit that drives the light emitter or the light emitters in a light-emitting state to guide each light emitter in the direction to expand or bend the finger, the direction to adduct or abduct the finger, and the direction to rotate the finger; and wherein the force sense transfer control unit controls the light-emitting drive unit so that the light-emitting drive unit becomes in a state based on the action element data.

As a result, regarding the end effector mounted on each finger by the collaborator, the movements of the fingers by the expert's work can be transferred at a delicate level to the collaborator. Moreover, since the end effector to be mounted on each finger of the collaborator is configured to not shield a finger pad of the relevant finger, the collaborator can perform their own work while touching the object directly with their respective fingers.

Furthermore, according to the present invention, there is included an end effector having the same configuration as that of each end effector mounted on each fingertip of the expert: and there is included a force displacement transfer unit that gives a force sense to prompt each finger to perform three-dimensional actions while transferring three-dimensional directional movements based on the physical feedback information of each end effector on the collaborating side, which is received by the instructing-side communication unit with respect to the relevant each end effector.

As a result, the expert in the state where the end effector, which has the same configuration as that of the collaborator, is mounted on each finger can perceive the content of the collaborator's work with respect to the finger movements transferred by the expert as the force sense transfer result in a feedback manner through the force displacement transfer unit. Therefore, not only the expert can perceive gaps between their own instruction content and the collaborator's response content on a real-time basis, but also the respective end effectors can operate integrally with the collaborator and fingertips' action information can be transferred to each other interactively.

Furthermore, according to the present invention, the instructing-side information processing apparatus includes: an instructing-side work electronic instrument that is operated by the expert by using their fingertips when performing the works; and an operation data quantitative extraction unit that extracts an adjusted amount by an operation capable of quantification, as instructing-side adjustment data, among operation content of the instructing-side work electronic instrument; wherein the instructing-side communication unit transmits the instructing-side adjustment data to the collaborating-side communication unit for the collaborating-side information processing apparatus via the network; and wherein the collaborating-side information processing apparatus includes: a collaborating-side work electronic instrument that has the same configuration as that of the instructing-side work electronic instrument and is operated by the collaborator by using their fingertips; and an operation data preferentially reflecting unit that preferentially reflects the adjusted amount of the relevant operation content, which is prioritized over the operation by the collaborator, in the operation content of the collaborating-side work electronic instrument on the basis of the instructing-side adjustment data received by the collaborating-side communication unit.

As a result, when the expert and the collaborator use and operate the work electronic instruments having the same configuration, it is possible to prevent the occurrence of errors in the series of actions in the work by prioritizing the adjusted amount of the expert's operation content over the operation by the collaborator and reflecting the adjusted amount of the expert's operation content in the operation content of the work electronic instrument by the collaborator.

Furthermore, according to the present invention, the collaborating-side work electronic instrument includes an operation deviation amount detection unit that detects a deviation amount between the adjusted amount of the operation content based on the instructing-side adjustment data and the adjusted amount of the operation content by the collaborator; wherein the operation deviation amount detection unit transmits the detected deviation amount as operation gap data to the collaborating-side communication unit and the instructing-side communication unit for the instructing-side information processing apparatus via the network if the detected deviation amount is equal to or larger than a predetermined threshold value; and wherein the instructing-side work electronic instrument includes a vibration feedback imparting unit that imparts vibrations according to the deviation amount based on the operation gap data received by the instructing-side communication unit to the fingertips of the expert and causes the fingertips of the expert to perceive the vibrations in a feedback manner.

As a result, when the expert and the collaborator use and operate the work electronic instruments having the same configuration and if the adjusted amount of the expert's operation content is prioritized over the operation by the collaborator and is reflected in the operation content of the work electronic instrument by the collaborator and if a deviation amount from the adjusted amount of the collaborator's operation content is equal to or more than a specified level, the expert can intuitively recognize differences from the collaborator in the operation content on a real-time basis by feeding back the deviation amount to the expert.

Furthermore, according to the present invention, the interactive information transfer system is provided in an freely attachable and detachable manner and separately from the collaborating-side work electronic instrument and the instructing-side work electronic instrument which mutually have the same configuration; and wherein the interactive information transfer system comprising: an instrument attachment including: an adjusted amount measurement unit that measures an adjusted amount by an operational means capable of quantification among a plurality of pieces of operation content; an operational status measurement unit that quantifies and measures an operational status other than the operational means among the plurality of pieces of operation content; and a synchronous data generation unit that generates synchronous data combined with measurement results by the adjusted amount measurement unit and the operational status measurement unit on the basis of the measurement results; wherein the synchronous data generation unit mutually transmits and receives the synchronous data to and from the collaborating-side communication unit for the collaborating-side information processing apparatus and the instructing-side communication unit for the instructing-side information processing apparatus via the network; and wherein the instrument attachment of each of the collaborating side and the instructing side includes: a difference amount detection unit that detects a difference amount of operation content based on a data comparison result of the synchronous data between the collaborating side and the instructing side; and a force sense feedback imparting unit that imparts a force sense according to the difference amount detected by the difference amount detection unit to fingers of the collaborator and the expert and causes the fingers to perceive the force sense in a feedback manner.

Accordingly, by mounting the instrument attachments having the same configuration respectively on the work electronic instruments on the collaborating side and the instructing side, both the collaborator and the expert can operate their work electronic instruments while mutually perceiving the adjusted amount by the operational means and the operational status other than the above-mentioned operational means on the other side as the force sense. Particularly, the manual skills and judgments by delicate work of the fingers, which are the operational status other than the operational means of the work electronic instruments can be also transferred as a quantitative force sense to each other.

Furthermore, according to the present invention, regarding the collaborating-side information processing apparatus: the force displacement transfer unit further includes an ambient temperature measurement unit that measures an ambient temperature of each end effector; and the collaborating-side communication unit transmits the ambient temperature of each end effector, which is calculated by the ambient temperature measurement unit, as ambient temperature data to the instructing-side communication unit for the instructing-side information processing apparatus; and wherein the instructing-side information processing apparatus includes: end sacs that are mounted on the respective fingertips of the expert, and each of which is equipped with a thermoelectric device; and a fingertip temperature adjustment unit that adjusts a temperature equivalent to an ambient temperature based on the ambient temperature data received by the instructing-side communication unit with respect to each thermoelectric device.

As a result, the realistic sensations when handling the object can be enhanced by adjusting each end sac worn by the expert to a temperature equivalent to the temperature which the collaborator feels at each fingertip.

Furthermore, according to the present invention, the interactive information transfer system includes: a collaborating-side data display unit that is provided near the collaborating-side video display unit for the collaborating-side information processing apparatus and displays a list of various types of data related to the object; and an instructing-side data display unit that is provided near the instructing-side video display unit for the instructing-side information processing apparatus and displays the same data group as a data group displayed by the collaborating-side data display unit, wherein the line-of-sight detection unit transmits the position of the line-of-sight extended end of the expert within the display range of the instructing-side data display unit, as line-of-sight position data, to the instructing-side communication unit; and wherein the collaborating-side data display unit that marks and displays the position of the line-of-sight extended end of the expert within its display range and based on the line-of-sight position data received by the collaborating-side communication unit.

As a result, the expert can not only share the video mainly targeted at the object handled by the collaborate and mark and display the position of the line-of-sight extended end in the display range of the same video, but also give instructions on the expert's skills realistically including the timing to move the line of sight by also teaching with the line of sight in the same manner with respect to display content of a data group which is necessary for the current work.

Furthermore, according to the present invention, The interactive information transfer system according to any one of claims 1 to 14, comprising a line-of-sight detection unit that detects a position of a line-of-sight extended end of the collaborator within a display range of the collaborating-side video display unit as line-of-sight position data, wherein the line-of-sight detection unit sends out the line-of-sight position data to the collaborating-side communication unit; and wherein the instructing-side video display unit marks and displays the position of the line-of-sight extended end of the collaborator which is based on the line-of-sight position data received by the instructing-side communication unit within the display range.

As a result, the expert can mark and display the position of their own line-of-sight end within the display range of the collaborating-side video display unit and, at the same time, can mark and display the position of the collaborator's line-of-sight end within the display range of the instructing-side video display unit, so that the collaborator and the expert can work while mutually visually checking the line-of-sight position of the other side on a real-time basis.

Furthermore, according to the present invention, the interactive information transfer system includes: an ambient sound collection unit that is provided in the collaborating-side information processing apparatus and collects sound waves including audible sounds and ultrasonic waves which occur in surroundings of the collaborator in synchronization with video capturing by the object imaging unit; and an ambient sound reproduction unit that that is provided in the instructing-side information processing apparatus and reproduces the audible sounds and the ultrasonic waves which are received by the instructing-side communication unit from the ambient sound collection unit.

As a result, the expert can share the collaborator's ambient environment visually and aurally with high accuracy by aurally perceiving not only the audible sounds, but also the ultrasonic waves regarding the collaborator's ambient environment under the expert's own environment.

Furthermore, according to the present invention, the instructing-side information processing apparatus includes a microphone which collects voices of the expert and the instructing-side communication unit transmits voice data, which is obtained from the microphone, on a real-time basis via the network; and wherein the collaborating-side information processing apparatus includes a speaker which reproduces voices based on the voice data, which is received by the collaborating-side communication unit, on a real-time basis.

As a result, when instructing the collaborator in the expert's own manual skills, the expert can not only transfer the skills to the fingers via the force sense, but also transfer the skills to ears via voices, so that the expert can give the instructions more accurately on a real-time basis.

Furthermore, according to the present invention, the force displacement transfer unit for the collaborating-side information processing apparatus immediately stops or resumes imparting the force sense to the collaborator according to speech content based on the voice data received by the collaborating-side communication unit.

As a result, if it is easier to understand the transferred content by directly using words rather than indirectly transferring the manual skills via the force sense when the expert instructs the collaborator in their skills, it is possible to prioritize aural instructions on a real-time basis.

Furthermore, according to the present invention, the interactive information transfer system is connected via the network to each of the instructing-side communication unit for the instructing-side information processing apparatus and the collaborating-side communication unit for the collaborating-side information processing apparatus; and wherein the interactive information transfer system includes: a work data storage unit that stores a series of action content of the expert and the collaborator regarding the work by mutually associating the series of action content with each other as instructing-side work data and collaborating-side work data; a significant feature extraction unit that sequentially and chronologically extracts significant feature points from each piece of the action content on the basis of the instructing-side work data and the collaborating-side work data which are obtained from the work data storage unit; a skill analysis unit that analyzes whether each of the feature points extracted by the significant feature extraction unit corresponds to an excellent skill for the work or not; and a skill data storage unit that stores the action content including each feature point, which is obtained as an affirmative analysis result by the skill analysis unit, as skill data indicating the excellent skill by the expert.

As a result, it becomes possible to accumulate data of the work content (the series of action content) of the expert and the collaborator, analyze the accumulated data, and provide information for proposing and estimating actions which would be useful to improve the skills.

Furthermore, according to the present invention, the interactive information transfer system includes: a data reading unit that sequentially reads, from the skill data storage unit, the skill data with high relevance with each piece of the action content when the collaborator executes the series of action content with regard to work identical to the work; an action content estimation unit that sequentially estimates whether or not each piece of the action content of the collaborator becomes chronologically increasingly likely to match action content corresponding to the excellent skill based on the skill data; and an action content reflecting unit that instructs the collaborator by reflecting the action content corresponding to the excellent skill based on the skill data in the action content executed by the collaborator on a real-time basis on the basis of an estimation result by the action content estimation unit.

As a result, by accumulating the information relating to the expert's skills, it becomes possible to succeed the skills (or to virtually give the instructions by the expert) even if the expert is absent when the collaborator performs the same work. Furthermore, it is expected that such accumulated information will be also utilized as educational information regarding the skills.

Furthermore, according to the present invention, an interactive information transfer method for an expert to instruct a collaborator in their skills regarding specific work while making the expert and the collaborator mutually exchange information via a network, the interactive information transfer method comprising: on the expert's side, detecting a position of a line-of-sight extended end of the expert within a display range of a video of an object handled by the collaborator as line-of-sight position data while receiving and displaying the video via the network, and at the same time detecting fingers' action data according to three-dimensional directional movements by setting respective fingertips of the expert as endpoints, and then transmitting the line-of-sight position data and the fingers' action data to the collaborator's side via the network on a real-time basis; and on the collaborator's side, marking and displaying the position of the line-of-sight extended end of the expert based on the line-of-sight position data received from the expert's side via the network within the display range of the video while capturing the video mainly targeted at the object, and at the same time imparting a force sense to prompt three-dimensional actions to each finger while transferring three-dimensional directional movements based on the fingers' action data with respect to each end effector mounted on each fingertip of the collaborator, and then transmitting physical feedback information of each end effector, which is a transfer result of the three-dimensional directional movements, together with the video captured and mainly targeted at the object to the expert's side via the network.

Furthermore, according to the present invention, an information transfer system for an expert, when performing specific work, to transfer their skills regarding the work to a collaborating side via a network while operating an instructing-side work electronic instrument by using their own fingertips, the information transfer system comprising: an instructing-side information processing apparatus including: an operation data quantitative extraction unit that extracts an adjusted amount by an operation capable of quantification, as instructing-side adjustment data, among operation content of the instructing-side work electronic instrument; and an instructing-side communication unit that transmits the instructing-side adjustment data; and a collaborating-side instrument attachment robot including: a collaborating-side communication unit that is attached in a freely attachable and detachable manner to a collaborating-side work electronic instrument having the same configuration as that of the instructing-side work electronic instrument and receives the instructing-side adjustment data transmitted from the instructing-side communication unit via the network; and an operation content reflecting unit that reflects an adjusted amount of the relevant operation content in operation content of the collaborating-side work electronic instrument on the basis of the instructing-side adjustment data.

Furthermore, according to the present invention, the information transfer system includes an adjusted amount measurement unit that measures an adjusted amount by an operation capable of quantification among a plurality of pieces of operation content of the collaborating-side work electronic instrument, wherein the operation content reflecting unit calibrates and corrects the adjusted amount of the operation content of the collaborating-side work electronic instrument on the basis of the adjusted amount which is fed back from the adjusted amount measurement unit.

Furthermore, according to the present invention, an information transfer system for an expert, when performing specific work, to transfer their skills regarding the work to a collaborating side via a network while operating an instructing-side work electronic instrument by using their own fingertips, the information transfer system comprising: an instructing-side instrument attachment including: an adjusted amount measurement unit that is attached in a freely attachable and detachable manner to the instructing-side work electronic instrument and measures an adjusted amount by an operational means capable of quantification among a plurality of pieces of operation content; an operational status measurement unit that quantifies and measures an operational status other than the operational means among the plurality of pieces of operation content; and a synchronous data generation unit that generates synchronous data combined with measurement results by the adjusted amount measurement unit and the operational status measurement unit on the basis of the measurement results; and an instructing-side communication unit that transmits the synchronous data; and a collaborating-side instrument attachment robot including: a collaborating-side communication unit that is attached in a freely attachable and detachable manner to a collaborating-side work electronic instrument having the same configuration as that of the instructing-side work electronic instrument and receives the synchronous data transmitted from the instructing-side communication unit via the network; an operation control unit that generates, as a control signal, adjusted amounts of the respective operational means based on the synchronous data and operation timing between the respective operational means; and an operational means drive unit that drives the respective operational means on the basis of the control signal by the operation control unit.

Furthermore, according to the present invention, the information transfer system includes an adjusted amount measurement unit that measures an adjusted amount by an operational means capable of quantification among a plurality of pieces of operation content of the collaborating-side work electronic instrument, wherein the operation control unit calibrates and corrects the adjusted amount of the operational means on the basis of the adjusted amount which is fed back from the adjusted amount feedback measurement unit.

Furthermore, according to the present invention, the information transfer system includes an operational status feedback measurement unit that quantifies and measures an operational status other than the operational means among a plurality of pieces of operation content of the collaborating-side work electronic instrument, wherein the operation control unit generates a measured amount of the operational status other than the operational means based on the synchronous data by including the measured amount in the control signal and transmits the control signal via the collaborating-side communication unit to external equipment which operates in cooperation with the collaborating-side work electronic equipment; and wherein the operation control unit generates calibration data indicating a comparison result between a measured amount of the operational status, which is fed back from the operational status feedback measurement unit via the external equipment and the collaborating-side work electronic instrument, and a measured amount of the operational status of the instructing side.

Advantageous Effects of the Invention

The present invention as described above can implement the interactive information transfer system and the interactive information transfer method which enable the expert who is at a remote location to indirectly instruct the collaborator in their skills which are tacit knowledge about specific work with very high accuracy on a real-time basis while at the same time allowing the expert and the collaborator to mutually exchange information and the expert to share realistic sensations with the collaborator via the network.

BRIEF DESCRIPTION OF DRAWINGS

FIG. 1 is a schematic diagram illustrating an overall configuration of an interactive information transfer system according to this embodiment;

FIGS. 6A to 6D are plan views and sectional views illustrating the appearance configuration of the fingertip back retaining part in FIG. 5;

FIG. 7 is a schematic diagram illustrating the configuration of a driving unit of the end effector in FIG. 4;

FIGS. 8A and 8B are schematic diagrams illustrating an appearance configuration of an end effector according to a second embodiment;

FIG. 9 is a schematic diagram illustrating a state where the end effector in FIG. 8 is mounted;

FIGS. 10A and 10B are plan views illustrating the configuration of an electrode catheter according to this embodiment;

FIGS. 20A to 20C are front views illustrating the configuration of the electrode catheter and the instrument attachment which are illustrated in FIG. 19;

FIGS. 23A and 23B are schematic diagrams for explaining an operational status of the electrode catheter via the instrument attachment in a state where force displacement transfer units on the collaborating side and the instructing side are mounted according to another embodiment;

DESCRIPTION OF EMBODIMENTS

An embodiment of the present invention will be described below in detail with reference to the drawings.

Figure 2:
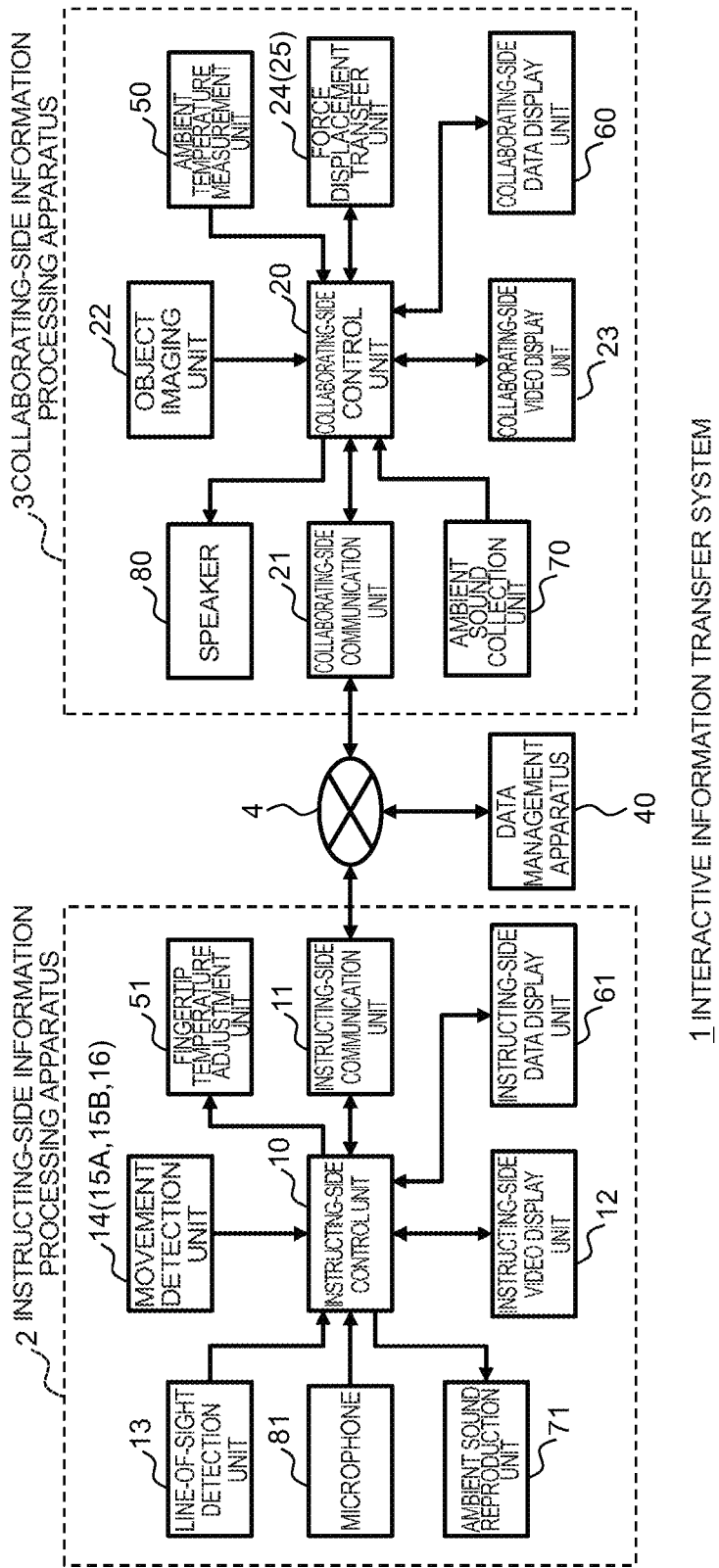
FIG. 2 is a block diagram illustrating a circuit structure of the interactive information transfer system illustrated in FIG. 1.

(1) Configuration of Interactive Information Transfer System According to this Embodiment FIG. 1 and FIG. 2 illustrate an interactive information transfer system 1 according to this embodiment as a whole; and an instructing-side information processing apparatus 2 provided on an expert's side and a collaborating-side information processing apparatus 3 provided on a collaborator's side are communicably connected via a network 4, so that the expert can instruct the collaborator in their skills regarding specific work while the expert and the collaborator mutually exchange information.

The instructing-side information processing apparatus 2 includes an instructing-side communication unit 11, an instructing-side video display unit 12, a line-of-sight detection unit 13, and a movement detection unit 14 under integrated control of an instructing-side control unit 10. The instructing-side communication unit 11 transmits fingers' action data D1, which is obtained from the movement detection unit 14 via a wireless LAN, a near field communication, or the like, on a real-time basis via the network 4.

The instructing-side video display unit 12 includes a video display and a speaker and displays a video received by the instructing-side communication unit 11 via the network 4 through the wireless LAN, the near field communication, or the like.

The line-of-sight detection unit 13 detects the position of the expert's line-of-sight extended end within a display range of the video, which is displayed by the instructing-side video display unit 12, as line-of-sight position data D2. Specifically speaking, the line-of-sight detection unit 13 recognizes movements of the collaborator's eyeballs through videos, detects the collaborator's line of sight, and calculates the position of the line of sight within the display range of the video displayed by the instructing-side video display unit 12. The configuration and method of the line-of-sight detection unit 13 are not particularly limited; however, besides the video capturing method, methods such as a method using infrared differential images or a light-of-sight specifying method using a spectacle-type sensor equipped with a half mirror may also be applied.

For example, the method using the infrared differential images is to make use of the fact that strong reflected images can be obtained from eyes when a light source is placed along the line of sight; and it is a method of irradiating the collaborator's eyes with two infrared rays having different wavelengths, extracting reflected images of iris parts from differences in the respective reflected images, and specifying the collaborator's line of sight from these reflected images.

The movement detection unit 14 includes a plurality of imaging cameras (three-dimensional imaging units) 15A, 15B (there are two imaging cameras in this embodiment, but there may be three or more imaging cameras) for capturing videos of the inside of a practical skill range mainly targeted at an area around the expert's hands from three-dimensional directions; and in a state where the expert is made to wear gloves 16 on which a specified pattern is formed at the expert's fingers, videos of the gloves 16 are captured from the plurality of directions and the instructing-side control unit (action arithmetic operation unit) 10 arithmetically operates three-dimensional coordinates whose origin is the collaborator's line-of-sight extended end, thereby detecting the fingers' action data D1 according to three-dimensional directional movements by setting the expert's respective fingertips as endpoints.

With this instructing-side information processing apparatus 2, the instructing-side communication unit 11 transmits the line-of-sight position data D2 obtained from the line-of-sight detection unit 13 and the fingertips' action data D1 obtained from the movement detection unit 14 to the collaborating-side information processing apparatus 3 on a real-time basis via the network 4.

Moreover, the collaborating-side information processing apparatus 3 includes a collaborating-side communication unit 21, an object imaging unit 22, a collaborating-side video display unit 23, and a force displacement transfer unit 24 under integrated control of a collaborating-side control unit 20. The collaborating-side communication unit 21 receives the line-of-sight position data D2 and the fingers' action data D1, which are transmitted from the instructing-side communication unit 11 via the network 4, through the wireless LAN, the near field communication, or the like. The object imaging unit 22 is composed of an imaging camera and captures videos mainly targeted at an object when the collaborator performs work.

The collaborating-side video display unit 23 displays the video captured by the object imaging unit 22 and, at the same time, marks and displays the position of the expert's line-of-sight extended end based on the line-of-sight position data D2 received by the collaborating-side communication unit 21 within the display range. Specifically speaking, if a two-dimensional coordinate system is set to the display range of the instructing-side video display unit 12, a specified mark M1 is displayed on a real-time basis within the display range of the collaborating-side video display unit 23 at a coordinate position which matches a coordinate position based on the line-of-sight position data D2.

The force displacement transfer unit 24 includes end effectors 25 which are respectively mounted on the collaborator's respective fingertips and impart a force sense to each finger to prompt three-dimensional actions while transferring the three-dimensional directional movements based on the fingertips' action data D1 received by the collaborating-side communication unit 21 with respect to the relevant each end effector 25.

The collaborating-side communication unit 21 transmits the video captured by the object imaging unit 22 and physical feedback information D3 of each end effector 25, which is a transfer result of the force displacement transfer unit 24, to the instructing-side communication unit 11 for the instructing-side information processing apparatus 2 via the network 4.

Consequently, with the interactive information transfer system 1 according to the invention, the expert: transfers the position of their own line-of-sight end to the collaborator on a real-time basis while visually checking the same video as the video mainly targeted at the object handled by the collaborator; and, at the same time, feeds back the transfer result to expert while giving instructions to transfer the three-dimensional directional movements of their own fingertips as the force sense to the collaborator's respective fingers on a real-time basis.

As a result, the collaborator can indirectly receive the instructions from the expert about the expert's manual skills, which are the expert's tacit knowledge, on a real-time basis while sharing the realistic sensations with the expert at the remote location when performing their work. Furthermore, the expert can perceive gaps between their own instruction content and the collaborator's response content on a real-time basis by perceiving the transfer result of the force sense to the collaborator in a feedback manner.

The interactive information transfer system 1 according to this embodiment is designed as described later so that various information including a series of action content of the expert and the collaborator with the instructing-side information processing apparatus 2 and the collaborating-side information processing apparatus 3 is recorded in a server for the data management apparatus 40 via the network 4.

Incidentally, with the instructing-side information processing apparatus 2 and the collaborating-side information processing apparatus 3, there are equipped with the following under control of the instructing-side control unit 10 and the collaborating-side control unit 20 according to embodiments described later: an ambient temperature measurement unit 50 on the collaborator's side and a fingertip temperature adjustment unit 51 on the expert's side for sharing an ambient temperature; a collaborating-side data display unit 60 on the collaborator's side and an instructing-side data display unit 61 on the expert's side for sharing various data group videos; an ambient sound collection unit 70 on the collaborator's side and an ambient sound reproduction unit 71 on the expert's side for sharing ambient sounds on the collaborating side; and a speaker 80 on the collaborator's side and a microphone 81 on the expert's side for voice instructions from the expert's side to the collaborator's side.

Figure 3:
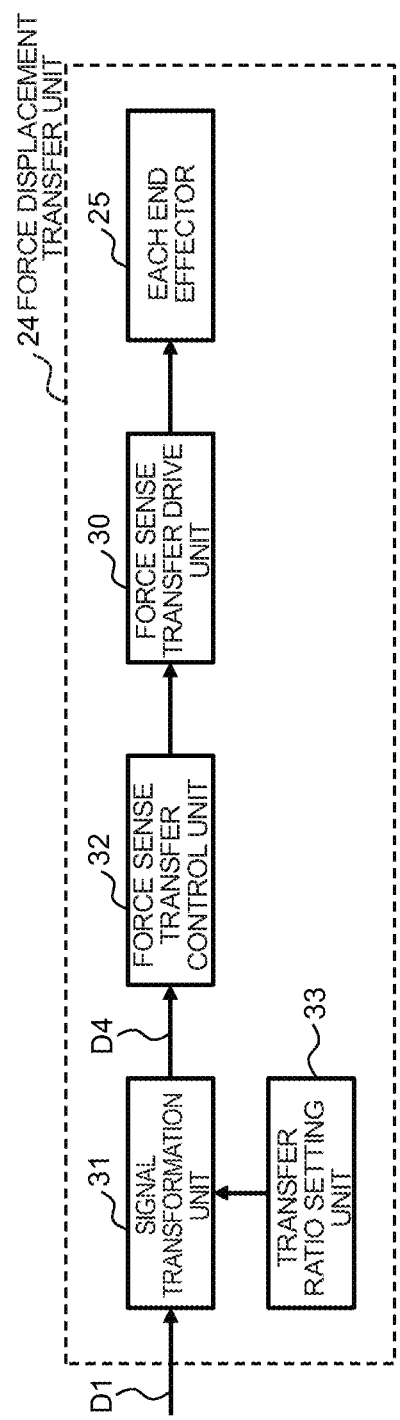
FIG. 3 is a block diagram illustrating an inner configuration of a force displacement transfer unit.

(2) Configuration of Force Displacement Transfer Unit According to this Embodiment The detailed configuration of the force displacement transfer unit 24 for the collaborating-side information processing apparatus 3 will be described later as a plurality of examples; however, as illustrated in FIG. 3, the force displacement transfer unit 24 includes end effectors 25 which are mounted on the respective fingertips including at least a thumb, an index finger, and a middle finger of the collaborator, a force sense transfer drive unit 30, a signal transformation unit 31, and a force sense transfer control unit 32. Incidentally, in this embodiment, the signal transformation unit 31 and the force sense transfer control unit 32 are designed so that they can be executed as partial functions of the collaborating-side control unit 20.

The force sense transfer drive unit 30 drives each end effector 25 to guide it in a direction to expand or bend the finger, a direction to adduct or abduct the finger, and a direction to rotate the finger.

The signal transformation unit 31 breaks down the three-dimensional directional movements of each endpoint of the expert into the position, speed, acceleration, angular velocity, force, and moment of the relevant endpoint and transforms each of them to action element data D4 on the basis of the fingers' action data D1 received by the collaborating-side communication unit 21.

The force sense transfer control unit 32 controls the force sense transfer drive unit 30 so that the position, speed, acceleration, angular velocity, force, and moment in the respective directions of each end effector 25 become in a state based on the action element data D4 obtained from the signal transformation unit.

As a result, by driving the end effectors 25 mounted on the respective fingers of the collaborator in conformity with the three-dimensional directional movements of the endpoints which are the expert's respective fingertips, it is possible to impart the force sense to each finger of the collaborator to guide the relevant finger in the direction to expand or bend the finger, the direction to adduct or abduct the finger, and the direction to rotate the finger.

Furthermore, the force displacement transfer unit 24 for the collaborating-side information processing apparatus 3: includes a transfer ratio setting unit 33 which changes the setting content according to external operations; and variably sets a transfer ratio of the three-dimensional directional movements based on the fingers' action data D1 with respect to each end effector 25 in accordance with the operations by the collaborator. The signal processing unit 31 adjusts the fingers' action data D1, which is action content of the expert's respective endpoints, to the transfer ratio which is set by the transfer ratio setting unit 33, and transforms it to the action element data D4 which is the three-dimensional directional movements of each end effector 25.

As a result, if the collaborator judges that their work would be negatively affected, they can increase or decrease a degree of transfer of the three-dimensional directional movements of the expert's respective fingertips by adjusting the transfer ratio by themselves.

For example, if the transfer ratio is 1, information related to the movements of the expert's fingertips (the force, speed, and displacement) become equivalent to the performance of the work (catheter ablation treatment surgical operation) remotely by the expert themselves. The expert can perform the work (remote treatment) while perceiving the fingertip information (information such as the force, speed, and displacement, as well as a reaction force configured of such information, and viscous friction) upon remote actions (catheter operations).

On the other hand, if the transfer ratio is 0, the collaborator's work (medical treatment) at the remote location will not be interrupted and the collaborator can implement the action content for the relevant work on their own will. Accordingly, it becomes possible to adjust whether the expert should be prioritized or the collaborator should be prioritized, by making it possible to interactively change the transfer ratio of the three-dimensional directional movements based on the fingers' action data D1.

(3) Configuration of End Effector According to this Embodiment

This embodiment will describe a case where the end effector(s) 25 illustrated in the following first embodiment is applied; however, the present invention is not limited to this example and end effectors illustrated in a second embodiment to a fourth embodiment may be applied and all or some of the end effectors according to these first to fourths embodiments may be combined and applied.

(3-1) First Embodiment of End Effector

Figure 4:
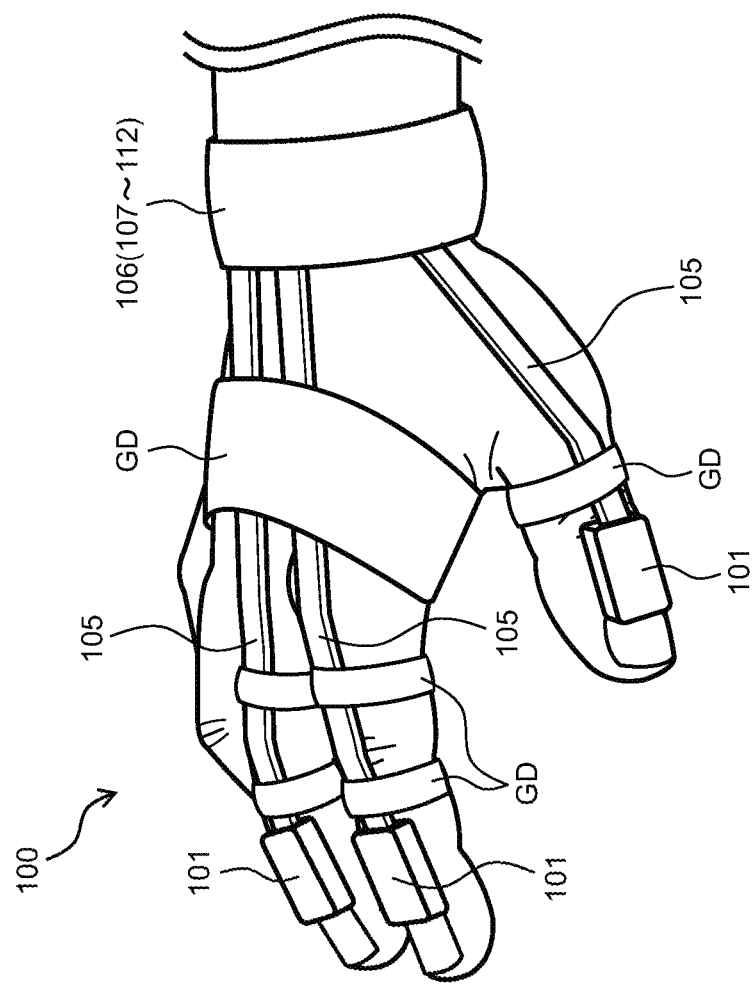
FIG. 4 is a schematic diagram illustrating an appearance configuration of an end effector according to a first embodiment.

Referring to FIG. 4, an end effector 100 which is mounted on the collaborator's respective fingertips includes: a fingertip back retaining part 101 that is retained in contact with a fingertip back part; and first linear members 102 and second linear members 103 which are pulled out in a paired state from above and below, and from the right and left sides of, an end 101A of the fingertip back retaining part 101. Referring to FIG. 4, all four linear members, that is, a pair of first linear members 102 and a pair of second linear members 103 are covered with a linear cover part 105, pass through each guide part GD mounted at each of areas between finger joints and at the back of the hand, and are pulled to a driving unit 106 which is wound around a wrist.

Figure 5:
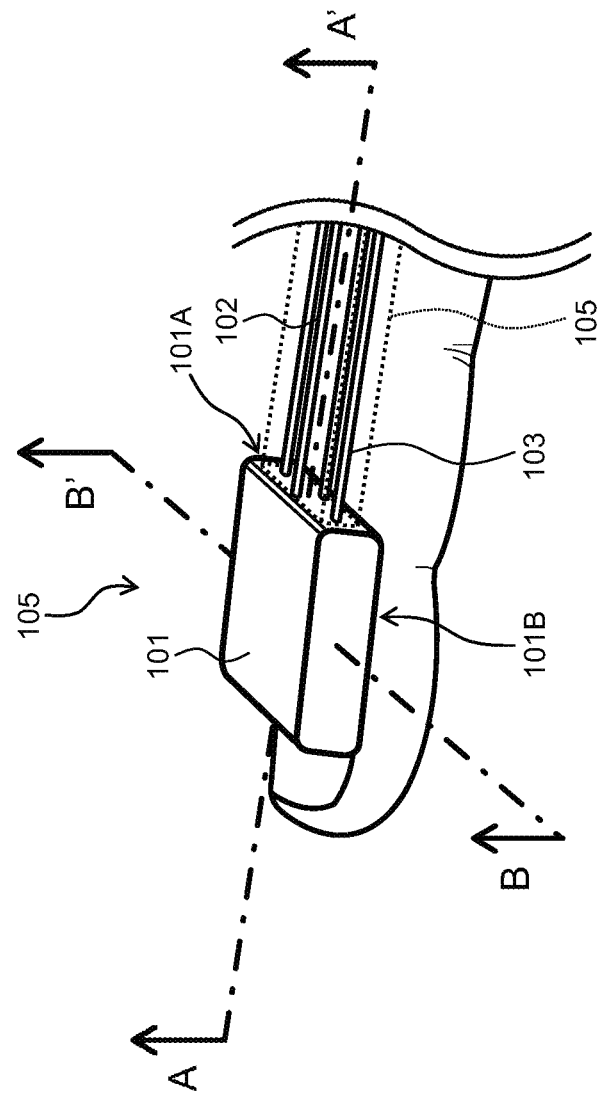
FIG. 5 is a schematic diagram illustrating the configuration of a fingertip back retaining part of the end effector in FIG. 4.

The fingertip back retaining part 101 is a chip-like member which is made of a resin material and is firmly fixed to a back part of the fingertip from the base of a nail to a first joint (hereinafter referred to as a "fingertip back part") as illustrated in FIG. 5; and four through holes 101HA to 101HD (FIG. 6A and FIG. 6B) are formed inside the fingertip back retaining part 101 from its end face on the finger base side to its contact face to be in contact with the fingertip. Referring FIG. 5, a sectional view of the fingertip back retaining part 101 as taken along arrows A-A' is illustrated in FIG. 6C and a sectional view of the fingertip back retaining part 101 as taken along arrows B-B' is illustrated in FIG. 6D.

Each through hole 101HA to 101HD formed in the fingertip back retaining part 101 is formed with a specified diameter from a specified positions in any one of upper, lower, right-side, and left-side portions of the end face to a specified position in any one of front-side, rear-side, right-side, and left-side portions of the contact face.

Referring to FIG. 5, one end of each of the pair of the first linear members 102 and the second linear members 103 is secured to any one of the specified positions in the front-side, rear-side, right-side, and left-side portions of the contact face of the fingertip back retaining part 101; and the other end of each of the first linear members 102 and the second linear members 103 is pulled out of any one of the specified positions in the upper, lower, right-side, and left-side portions of the end face 101A through each through hole 101HA to 101HD and engages with the expansion/bending drive unit 107 and the adduction/abduction drive unit 108 for the driving unit 106, respectively.

Referring to FIG. 7, the expansion/bending drive unit 107: includes a servo motor 110, an output shaft of which is made to engage with a pulley 109 with a diameter of approximately 10 mm; and is designed to retain the fingertip back retaining part 101 via the first linear member 102, which is stretched over the relevant pulley 109, and urge the fingertip back retaining part 101 in a forward or backward direction.

The first linear member 102 is made of a metallic wire with high tensile strength; and one end and the other end of the first linear member 102 are secured respectively at the specified positions in the front and rear portions of the contact face 101B of the fingertip back retaining part 101 and also are secured and connected to the pulley 109.

The expansion/bending drive unit 107 rotates the output shaft of the servo motor 110 in a rotating direction and at a rotating speed as controlled by the force sense transfer control unit 32 and thereby transfers its rotary force as a linear motion to the first linear member 102 via the pulley 109. The fingertip back retaining part 101 is slightly pressed against the fingertip back part in either the forward or backward direction of the contact face 101B on the basis of a current rotation angle of the pulley 109.

The adduction/abduction drive unit 108: includes a servo motor 112, an output shaft of which is made to engage with a pulley 111 with a diameter of approximately 10 mm; and is designed to retain the fingertip back retaining part 101 via the second linear member 103, which is stretched over the relevant pulley 111, and urge the fingertip back retaining part 101 in a right or left direction.

The second linear member 103 is made of a metallic wire with high tensile strength; and one end and the other end of the second linear member 103 are secured respectively at the specified positions in the right and left portions of the contact face 101B of the fingertip back retaining part 101 and also are secured and connected to the pulley 111.

The adduction/abduction drive unit 108 rotates the output shaft of the servo motor 112 in a rotating direction and at a rotating speed as controlled by the force sense transfer control unit 32 and thereby transfers its rotary force as a linear motion to the second linear member 103 via the pulley 111. The fingertip back retaining part 101 is slightly pressed against the fingertip back part in either the right or left direction of the contact face 101B on the basis of a current rotation angle of the pulley 111.

Consequently, the force sense transfer control unit 32 controls the expansion/bending drive unit 107 and the adduction/abduction drive unit 108 for the driving unit 106, respectively, so that they become in a state based on the action element data D4, thereby moving the first linear member 102 in the pushing or pulling direction, imparting a pressing force sense according to that direction to the fingertip back part, and guiding the fingertip in the direction to expand or bend the fingertip, and also moving the second linear member 103 in the right or left direction, imparting the pressing force sense according to that direction to the fingertip back part, and guiding the fingertip in the direction to adduct or abduct the fingertip.

As a result, regarding the end effector 100 mounted on each finger of the collaborator, the expert's finger movements through the work can be transferred to the collaborator at a delicate level. Moreover, since the end effector 100 mounted on each finger of the collaborator is configured to not shield a finger pad of the finger, the collaborator can perform their work while directly touching the object with their respective fingers.

(3-2) Second Embodiment of End Effector

An end effector 120 which is mounted on the collaborator's respective fingertips includes, as illustrated in FIG. 8A and FIG. 8B, a substantially C-shaped ring unit (wound rotation unit) 121 which is a partly open ring. The ring unit 121 is configured so that an inner ring 123 which is attached in a freely rotatable manner to an outer ring 122 as a frame performs reciprocating motions as driven by an actuator (rotation drive unit) 124.

Specifically, this actuator 124 applies an electric current to an exciting coil, generates a magnetic flux by exciting a magnetic circuit configured from the outer ring which is a stator and the inner ring 123 which is a mover, and causes the inner ring to perform the reciprocating motions with the generated electromagnetic force.

Incidentally, the actuator 124 as the rotation drive unit may be configured to cause the inner ring to perform the reciprocating motions relative to the outer ring by piezoelectric thrust other than the electromagnetic force. For example, the actuator 124 may be configured so that a displacement of a piezoelectric actuator causes its displacement direction and a displacement amount to be transformed to a reciprocating displacement direction and a reciprocating displacement amount of the inner ring relative to the outer ring.

Referring to FIG. 9, when a driving unit 125 which is wound around the wrist receives a control command signal to become in a state based on the action element data D4 by the force sense transfer control unit 32, it drives and controls each actuator 124 via a communication means (which is not illustrated in the drawing) such as a near field communication.

This ring unit 121 is wound around and fixed to the relevant finger at any one or more positions of an area between the fingertip to a first joint, an area between the first joint and a second joint, and an area between the second joint and a third joint by placing the ring unit 121 at the center of the back part of the relevant finger in such a manner that the contact face in contact with the finger can freely rotate in a rotating direction.

Consequently, by controlling the actuator (rotation drive unit) 124 so that it becomes in the state based on the action element data D4, the force sense transfer control unit 32 rotates the contact face of the ring unit 121 in contact with the finger according to the electromagnetic force or the piezoelectric thrust and guides the finger in the rotating direction.

As a result, when the collaborator performs not only actions in the expanding or bending direction or the adduction or abduction direction, but also a twisting action by using the fingertips with respect to the end effector 120 mounted on each finger, the expert's finger movements through the work can be transferred to the collaborator at a delicate level by transferring the force sense to also guide the relevant finger in the rotating direction. Moreover, since the end effector 120 mounted on the collaborator's each finger is structured to not shield the finger pad of the finger, the collaborator can perform their work while directly touching the object with their hands.

(3-3) Third Embodiment of End Effector

An end effector (which is not illustrated in drawings) to be mounted on the collaborator's each fingertip includes a vibration actuator (vibration drive unit) that drives a single vibrating element or a plurality of vibrating elements which are mounted by placing the relevant vibrating element(s) at the center of the collaborator's fingertip back part. For example, the vibration actuator which uses ultrasonic wave vibrations applies an AC voltage to a single piezoelectric element or a plurality of piezoelectric elements (vibrating elements) to cause elliptic motions or progressive waves to occur on a surface of a stator, and causes a mover to press-contact the stator, thereby causing the mover to perform motions with directivity in three-dimensional directions via a frictional force between the stator and the mover.

Consequently, by controlling the vibration drive unit so that it becomes in the state based on the action element data D4, the force sense transfer control unit 32 guides the single vibrating element or each of the plurality of vibrating elements in the direction to expand or bend the finger, the direction to adduct or abduct the finger, and the direction to rotate the finger, respectively.

As a result, regarding the end effector mounted on each finger by the collaborator, the movements of the fingers by the expert's work can be transferred at a delicate level to the collaborator. Moreover, since the end effector to be mounted on each finger of the collaborator is configured to not shield a finger pad of the relevant finger, the collaborator can perform their own work while touching the object directly with their respective fingers.

(3-4) Fourth Embodiment of End Effector

An end effector (which is not illustrated in drawings) to be mounted on the collaborator's each fingertip includes a light-emitting drive unit that drives a single light emitter or a plurality of light emitters (such as a small LED(s)) which are mounted by placing the relevant light emitter(s) at the center of the collaborator's fingertip back part. The light-emitting drive unit drives the single light emitter or the plurality of light emitters to cause them to emit light in a lighting pattern or a blinking pattern with directivity in the three-dimensional directions.

Consequently, by controlling the light-emitting drive unit so that it becomes in the state based on the action element data D4, the force sense transfer control unit 32 guides the single light emitter or each of the plurality of light emitters in the direction to expand or bend the finger, the direction to adduct or abduct the finger, and the direction to rotate the finger, respectively.

As a result, regarding the end effector mounted on each finger by the collaborator, the movements of the fingers by the expert's work can be transferred at a delicate level to the collaborator. Moreover, since the end effector to be mounted on each finger of the collaborator is configured to not shield a finger pad of the relevant finger, the collaborator can perform their own work while touching the object directly with their respective fingers.

(4) Configuration of Work Electronic Instrument According to this Embodiment

An explanation will be provided about a case where the interactive information transfer system 1 according to this embodiment is applied to the collaborator's environment which is the inside of an operating room of a medical institution. For example, an explanation will be provided about a case where the collaborator performs a surgical operation for the catheter ablation treatment for a patient who suffers from tachyarrhythmia.

In this curative operation, the collaborator inserts an electrode catheter, whose top end is deflectable and bends in two directions, from a vein at the patient's leg joint or neck under the local anesthesia through blood vessels into their heart, finds a site which caused the arrhythmia while measuring an electrocardiogram via an electrode at the tip end of the catheter, and causes cauterization of cardiac tissues by applying a high-frequency current from the tip end of the catheter to the site to be treated.

Incidentally, this electrode catheter is used in combination with a dedicated high-frequency output generating apparatus (which is not illustrated in drawings) when performing the cardiac muscle burning treatment (ablation) and is also used while checking that the placed site is appropriate via radioscopy and intracardiac potential recording.

This electrode catheter 130 is configured, as illustrated in FIG. 10A and FIG. 10B, a handle part 131 to be held with a hand; a connector 132 which is formed at an end of the handle part 131 and is to be electrically connected with the high-frequency output generating apparatus; a lever 133 and a tension knob 134 which are provided at a tip end of the handle part 131; a shaft 136 which is a microtubule with a chip electrode 135 attached to its top end.

Figure 11:
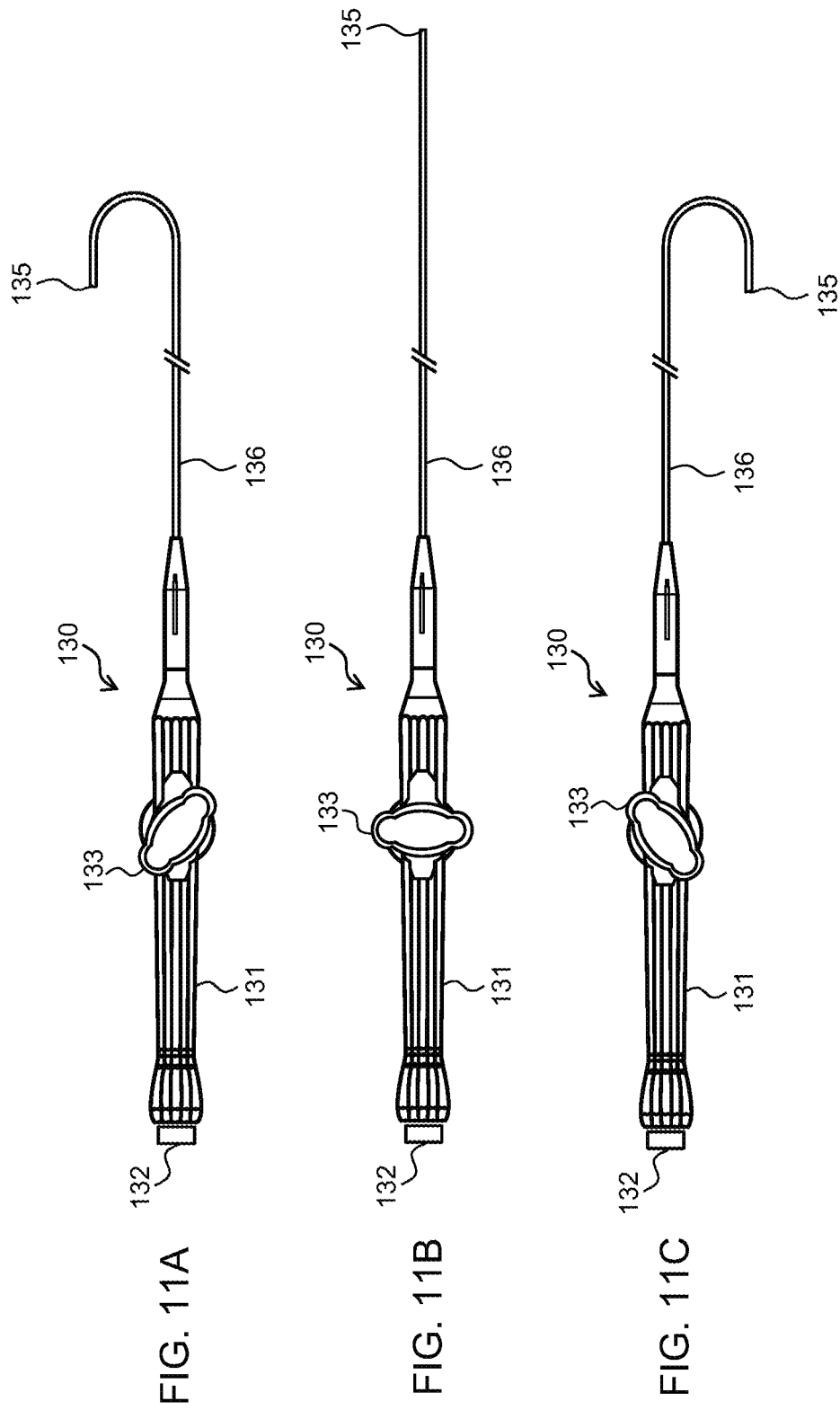
FIGS. 11A to 11C are plan views illustrating movable states of the electrode catheter in FIG. 10.

The collaborator can bend the top end of the shaft 136 at a desired curvature in a state of holding the handle part 131 of the electrode catheter 130 by rotating the lever 133 with the other hand (FIG. 11A to FIG. 11C). The bending size of the shaft 136 is designed to be proportional to the degree of rotations of the lever 133. Moreover, it is possible to increase or decrease frictions in a bending function by rotating the tension knob 134 provided on the opposite side of the lever 133. Then, at a point in time when it is confirmed that the chip electrode 135 is stably in contact with the target site, high-frequency energization is implemented by the high-frequency output generating apparatus via the connector 132 by stepping on a pedal (which is not illustrated in drawings) under their foot.

Figure 12:
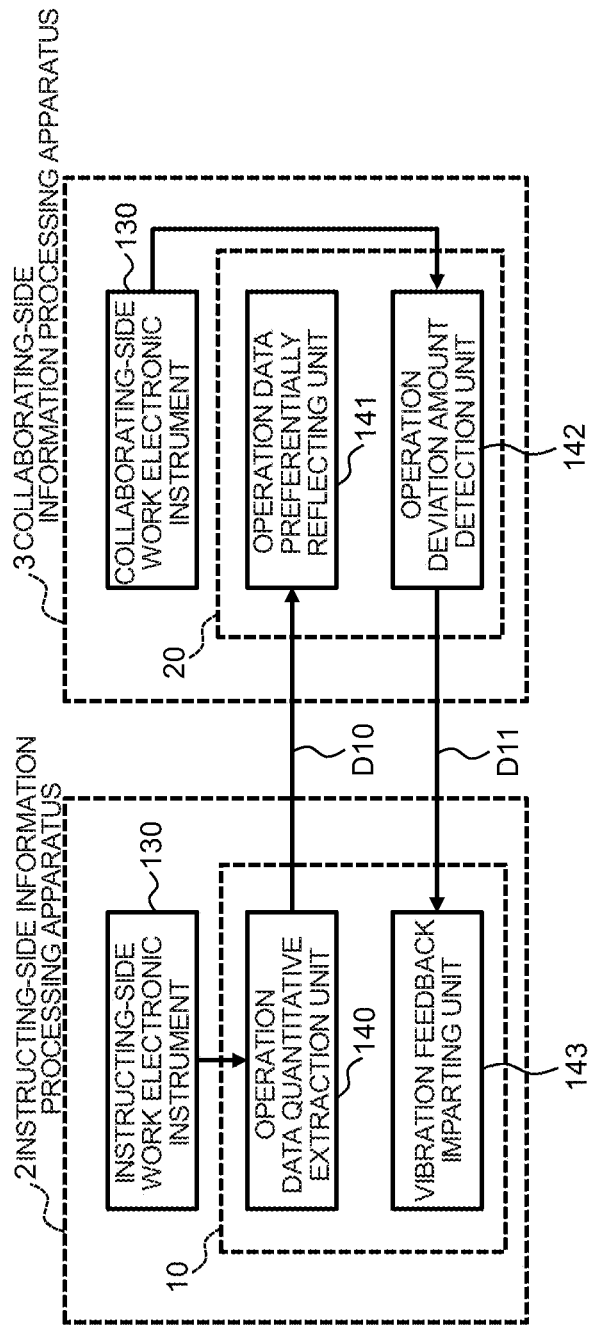
FIG. 12 is a block diagram for explaining information transfer on the expert's side and the collaborator's side regarding the operation of the electrode catheter according to this embodiment.

In this embodiment as illustrated in FIG. 12, the instructing-side information processing apparatus 2 is provided with: an electrode catheter (instructing-side work electronic instrument) 130 to be operated by the expert when performing work by using their own fingertips; and an operation data quantitative extraction unit 140 that extracts an adjusted amount by an operation capable of quantification among operation content of the electrode catheter 130.

The operation data quantitative extraction unit 140 extracts the degree of rotations of each of the lever 133 and the tension knob 134 for the electrode catheter 130 on a minute angle basis (for example, a one-degree basis with reference to 360 degrees) as an adjusted amount and transmits the adjusted amount as instructing-side adjustment data D10 to the collaborating-side communication unit 21 for the collaborating-side information processing apparatus 3 via the network 4 (which is not illustrated in FIG. 12).

The collaborating-side information processing apparatus 3 is provided with: an electrode catheter (collaborating-side work electronic instrument) 130 which has the same configuration as that of the electrode catheter that is the instructing-side work electronic instrument, and which is to be used by the collaborator by using their own fingertips; and an the operation data preferentially reflecting unit 141 which causes the adjusted amount of the relevant operation content to be reflected in the operation content of the electrode catheter (collaborating-side work electronic instrument) 130, on the basis of the instructing-side adjustment data D10 received by the collaborating-side communication unit 21, by prioritizing the adjusted amount of the relevant operation content over the operation by the collaborator.

As a result, when the expert and the collaborator use and operate the electrode catheters (work electronic instruments) 130 having the same configuration, it is possible to avoid the occurrence of errors in the series of actions for the work by prioritizing the adjusted amount of the expert's operation content over the operation by the collaborator and reflecting such adjusted amount in the operation content of the electrode catheter 130 by the collaborator. Specifically speaking, if the collaborator at the remote location places their fingertips at the lever 133 and the tension knob 134 of the electrode catheter 130, the collaborator can perceive the expert's manual skills as learned actions.

Furthermore, the electrode catheter 130 which is the collaborating-side work electronic instrument is provided with an operation deviation amount detection unit 142 that detects a deviation amount between the adjusted amount of the operation content of the lever 133 and the tension knob 134 based on the instructing-side adjustment data D10 and the adjusted amount of the operation content of the lever 133 and the tension knob 134 by the collaborator.

If the detected deviation amount is equal to or larger than a predetermined threshold value, the operation deviation amount detection unit 142 transmits it as operation gap data D11 to the collaborating-side communication unit 21 and via the network 4 to the instructing-side communication unit 11 for the instructing-side information processing apparatus 2. The level of this threshold value can be adjusted and may be adjusted to increase according to a skill level of the collaborator; and whether the expert should be prioritized or the collaborator should be prioritized may be adjusted by making the transfer ratio interactively variable as explained earlier.

The electrode catheter 130 which is the instructing-side work electronic instrument is provided with a vibration feedback imparting unit 143 that imparts vibrations according to the deviation amount based on the operation gap data D11, which is received by the instructing-side communication unit 11, to the expert's fingertips and make them perceive the vibrations in a feedback manner.

The vibration feedback imparting unit 143: includes, for example, a vibration actuator which uses ultrasonic wave vibrations; and feeds back the force sense to the expert's fingertips and makes them perceive the force sense by driving a piezoelectric element(s) with the strength according to the deviation amount based on the operation gap data D11.

As a result, when the expert and the collaborator use and operate the electrode catheters (work electronic instruments) 130 having the same configuration, the adjusted amount of the expert's operation content is prioritized over the operation by the collaborator and is reflected in the operation content of the electrode catheter (work electronic instruments) 130 of the collaborator; however, if the deviation amount from the adjusted amount of the collaborator's operation content is equal to or more than a specified level, the expert can intuitively recognize different parts from the collaborator's operation content by feeding back the deviation amount to the expert.

(5) Configuration Regarding Shared Ambient Environment According to this Embodiment (5-1) When Ambient Temperature is Shared The force displacement transfer unit 24 for the collaborating-side information processing apparatus 3 is provided with an ambient temperature measurement unit 50 (FIG. 2) which is a radiation thermometer (a thermometer for measuring a temperature of an object by measuring the strength of infrared rays or visible rays emitted from the object) at each end effector 25 and is designed to measure an ambient temperature of each end effector 25 contactlessly.

The collaborating-side communication unit 21 transmits the ambient temperature of each end effector 25, which is measured by the ambient temperature measurement unit 50, as ambient temperature data to the instructing-side communication unit 11 for the instructing-side information processing apparatus 2. Regarding the instructing-side information processing apparatus 2, an end sac equipped with a thermoelectric device is mounted on each of the expert's fingertips and the fingertip temperature adjustment unit 51 (FIG. 2) adjusts each thermoelectric device at a temperature equivalent to a temperature based on the ambient temperature data received by the instructing-side communication unit 11.

As a result, it is possible to improve the realistic sensations when handling the object by adjusting each end sac worn by the expert at the temperature equivalent to the temperature perceived by the collaborator's each fingertip.

(5-2) When Display of a Plurality of Videos is Shared

The interactive information transfer system 1 is provided with: a collaborating-side data display unit 60 (FIG. 2) which displays a list of various types of data related to the object, near the collaborating-side video display unit 23 for the collaborating-side information processing apparatus 3; and an instructing-side data display unit 61 (FIG. 2) which displays the same data group as a data group displayed by the collaborating-side data display unit 60, near the instructing-side video display unit 12 for the instructing-side information processing apparatus 2.

For example, when the collaborator performs a surgical operation for the catheter ablation treatment, a video (X-ray transmission video) mainly targeted at an object such as the inside of the patient's heart is displayed on the collaborating-side video display unit 23 and, at the same time, a similar video is displayed on the instructing-side video display unit 12. Besides this, if intracardiac electrical potential recording data is to be displayed on another display monitor, display monitors (a collaborating-side data display unit and an instructing-side data display unit) 60, 61 which are common on the collaborator's side and the expert's side are made to respectively display the same data content.

With the instructing-side information processing apparatus 2, the instructing-side communication unit 11 transmits the line-of-sight position data D2, which is obtained from the line-of-sight detection unit 13, on a real-time basis to the collaborating-side information processing apparatus 3 via the network 4. The collaborating-side data display unit 60 marks and displays the position of the expert's line-of-sight extended end based on the line-of-sight position data D2 received by the collaborating-side communication unit 21 within the display range. Specifically speaking, if a two dimensional coordinate system is set to the display range of the instructing-side data display unit 61, a specified mark is displayed on a real-time basis within the display range of the collaborating-side data display unit 60 at a coordinate position which matches a coordinate position based on the line-of-sight position data D2.

As a result, the expert can instruct the expert's skills including the timing to move the line of sight more realistically by not only sharing the video mainly targeted at the object handled by the collaborator and marking and displaying the position of the line-of-sight extended end within the display range of the same vide, but also similarly teaching, with the line of sight, the display content of a data group which is necessary for the current work.

(5-3) When Ambient Sounds are Shared

With the interactive information transfer system 1, the ambient sound collection unit 70 (FIG. 2) provided in the collaborating-side information processing apparatus 3: is composed of a broadband microphone which is relatively highly sensitive; and collects sounds of sound waves including the audible sounds and the ultrasonic waves, which occur in the surroundings of the collaborator, in synchronization with video capturing by the object imaging unit 22.

The ambient sound reproduction unit 71 (FIG. 2) provided in the instructing-side information processing apparatus 2 is composed of an ultrasonic wave speaker capable of reproducing not only sound waves of an audiofrequency band, but also sound waves of a high frequency band and reproduces the audible sounds and the ultrasonic waves which are received by the instructing-side communication unit 11 from the ambient sound collection unit 70.

As a result, the expert can share the collaborator's ambient environment visually and aurally with high accuracy by perceiving, with the auditory sense under the expert's own environment, not only the audible sounds, but also the ultrasonic waves regarding the collaborator's ambient environment.

(5-4) Voice Instructions from the Expert's Side to the Collaborator's Side

With the interactive information transfer system 1, the microphone 81 (FIG. 2) provided in the instructing-side information processing apparatus 2 transmits voice data, which is obtained by collecting the expert's voices, via the instructing-side communication unit 11 and then the network 4 on a real-time basis. The speaker 80 (FIG. 2) provided in the collaborating-side information processing apparatus 3 reproduces the voices based on the voice data received by the collaborating-side communication unit 21 on a real-time basis.

As a result, when the expert instructs the collaborator in their own manual skills, it is possible to perform not only the transfer to the fingers via the force sense, but also the transfer to the ears via the voices at the same time and give much more accurate instructions on a real-time basis.

Furthermore, the force displacement transfer unit 24 for the collaborating-side information processing apparatus 3 immediately stops or resumes imparting the force sense to the collaborator in response to speech content based on the voice data received by the collaborating-side communication unit 21. As a result, if it is easier to understand the transferred content by directly using words rather than indirectly transferring the manual skills via the force sense when the expert instructs the collaborator in their skills, it is possible to prioritize aural instructions on a real-time basis.

(6) Accumulated Data Management and Utilization Method

Figure 13:
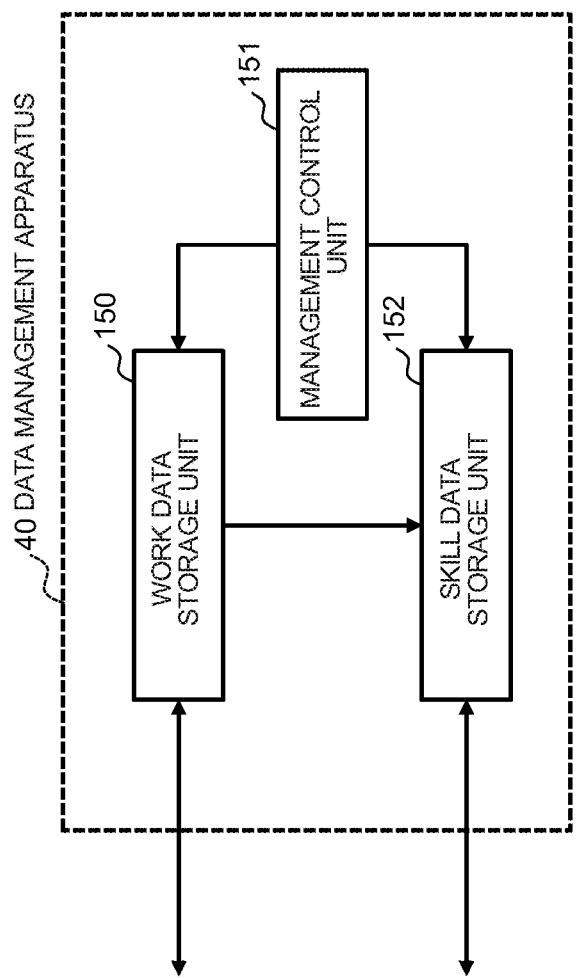
FIG. 13 is a block diagram illustrating an inner configuration of a data management apparatus according to this embodiment.

With the interactive information transfer system 1, the data management apparatus 40 is connected to each of the instructing-side communication unit 11 for the instructing-side information processing apparatus 2 and the collaborating-side communication unit 21 for the collaborating-side information processing apparatus 3 via the network 4 (FIG. 2). This data management apparatus 40 includes a work data storage unit 150 having a server configuration as illustrated in FIG. 13 and a series of action content of the expert and a series of action content of the collaborator regarding the work are associated with each other as instructing-side work data and collaborating-side work data and are stored in the work data storage unit 150.

The data management apparatus 40: includes a management control unit (a significant feature extraction unit and a skill analysis unit) 151; and chronologically sequentially extracts significant feature points (actions of the expert's manual skills with relatively large differences from the collaborator) among the respective pieces of the action content on the basis of the instructing-side work data and the collaborating-side work data which are read from the work data storage unit 150, and then analyzes whether each of the extracted feature points corresponds to an excellent skill for the work or not.

Subsequently, the management control unit 151 stores the action content including each feature point, which is obtained as an affirmative analysis result, as skill data indicating the excellent skill by the expert in a skill data storage unit 152 having a server configuration. This embodiment has described a case where the work data storage unit 150 and the skill data storage unit 152 are separate server configurations; however, they may be integrated to either one of the servers.

As a result, it becomes possible to accumulate the work content (the series of action content) of the expert and the collaborator in the work data storage unit 150, analyze the accumulated data, store information for proposing and estimating actions which are useful to improve the skills in the skill data storage unit 152, and provide such information.

Furthermore, with the data management apparatus 40, when the collaborator executes the series of action content with regard to work which is the same as the work, the management control unit (a data reading unit and an action content estimation unit) 151 sequentially reads the skill data having high relevance with the relevant each piece of the action content from the skill data storage unit 152 and then sequentially estimates whether or not it becomes chronologically increasingly likely that each piece of the action content of the collaborator matches the action content corresponding to the excellent skill based on the skill data.

Specifically speaking, in order for the collaborator to execute the series of action content, which is the current work, and receive the instructions on the action content which is the expert's skills on a real-time basis, it is necessary to make estimation from the immediately preceding action content. It is desirable to estimate the action content corresponding to the excellent skill on a real-time basis on the basis of how high the correlation between before and after the action content.

Subsequently, the management control unit (action content reflecting unit) 151 instructs the collaborator by causing the action content corresponding to the excellent skill based on the skill data to be reflected in the action content to be executed by the collaborator on a real-time basis on the basis of the estimation result.

As a result, it becomes possible to succeed the skills (or virtually give the instructions from the expert) even if the expert is absent when the collaborator executes the same work, by accumulating the information about the skills by the expert. Furthermore, it is expected that such information can be utilized as educational information regarding the skills.

(7) Actions and Advantageous Effects of this Embodiment

Figure 14:
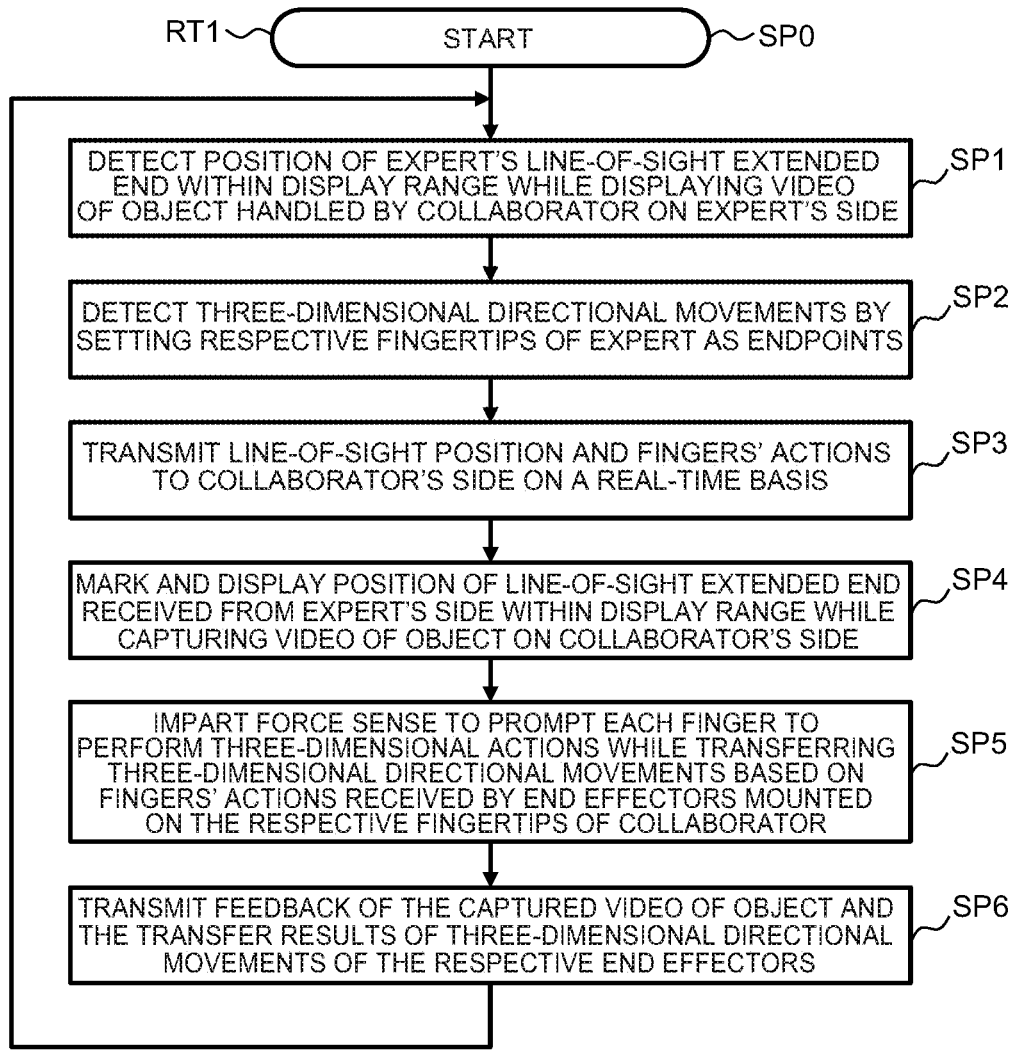
FIG. 14 is a flowchart for explaining interactive information transfer processing according to this embodiment.

According to the above-described configuration, when the expert instructs the collaborator in their skills regarding the specific work while the expert and the collaborator mutually exchange the information via the network 4, the interactive information transfer system 1 starts an interactive information transfer processing sequence RT1 illustrated in FIG. 14 from step SP0.

Firstly, on the expert's side, while receiving and displaying a video of the object handled by the collaborator via the network 4, the position of the expert's line-of-sight extended end within the display range of the video is detected as the line-of-sight position data (step SP1).

At the same time, the expert's respective fingertips are set as endpoints and the fingers' action data according to their respective three-dimensional directional movements is detected (step SP2); and then the line-of-sight position data and the fingers' action data are transmitted to the collaborator's side on a real-time basis via the network (step SP3).

Subsequently, on the collaborator's side, while capturing a video mainly targeted at an object, the position of the expert's line-of-sight extended end based on the line-of-sight position data received from the expert's side via the network is marked and displayed within the display range of the above-captured video (step SP4).

At the same time, while transferring the three-dimensional directional movements based on the fingers' action data with respect to the end effector mounted on the collaborator's each fingertip, the force sense is imparted to the relevant each finger to prompt it to perform three-dimensional actions (step SP5); and then, physical feedback information of each end effector, which is a transfer result of the three-dimensional directional movements, together with the video captured and mainly targeted at the object, is transmitted via the network to the expert's side (step SP6). Subsequently, the processing returns to step SP1 again and processing similar to the above-described processing is repeated.

Accordingly, the expert: transfers the position of their own line-of-sight end on a real-time basis to the collaborator while visually checking the same video as the video mainly targeted at the object handled by the collaborator; and, at the same time, feeds back the transfer result to the expert while giving instructions to transfer the three-dimensional directional movements of their own fingertips to the collaborator's respective fingers as the force sense on a real-time basis.

As a result, when the collaborator performs their own work, the collaborator can indirectly receive the instructions on the expert's manual skills, which are the expert's tacit knowledge, on a real-time basis while sharing the realistic sensations with the expert at the remote location. Furthermore, the expert can perceive gaps between their own instruction content and the collaborator's response content on a real-time basis by perceiving the transfer result of the force sense to the collaborator in a feedback manner.

According to the above-described configuration, it is possible to implement the interactive information transfer system that enables the expert at the remote location and the collaborator to mutually exchange the information while sharing the realistic sensations via the network and, at the same time, enables the expert to indirectly instruct the collaborator in their skills, which are their tacit knowledge, regarding the specific work with very high accuracy on a real-time.

(8) Other Embodiments

Incidentally, this embodiment has described the interactive information transfer system 1 that enables the expert to instruct the collaborator in their skills regarding the surgical operation for the catheter ablation treatment while the expert and the collaborator mutually exchange the information via the network; however, the present invention is not limited to this example and can be applied to a wide variety of work, which leads to succession of craftmanship skills such as traditional craftwork and cooking other than curative operations as long as the work is work of the expert to instruct the collaborator in the expert's manual skills as the skills.

Moreover, this embodiment has described the case where the position of the expert's line-of-sight extended end within the display range of the video displayed on the instructing-side video display unit 12 is detected by using the line-of-sight detection unit 13 for the instructing-side information processing apparatus 2 and the position of the expert's line-of-sight extended end, which is the detection result, is marked and displayed within the display range of the collaborating-side video display unit 23 for the collaborating-side information processing apparatus 3; however, the present invention is not limited to this example and the position of the collaborator's line-of-sight extended end within the display range of the collaborating-side video display unit 23 may be detected and the mark may be displayed on the instructing-side video display unit 12.

Figure 15:
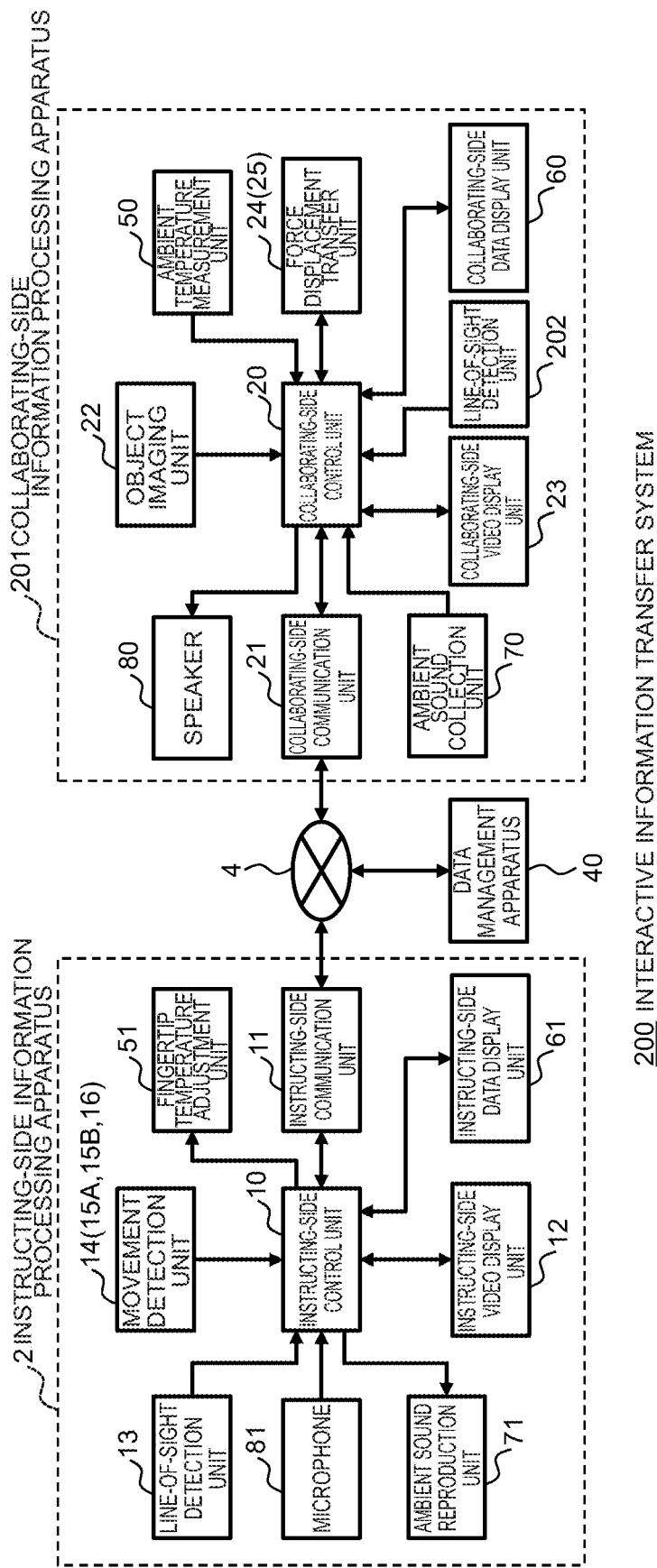
FIG. 15 is a block diagram illustrating a circuit structure of an interactive information transfer system according to another embodiment.

Specifically speaking, as illustrated in FIG. 15 in which the same reference numerals as those in FIG. 2 are assigned to parts corresponding to those in FIG. 2, with a collaborating-side information processing apparatus 201 for an interactive information transfer system 200, a line-of-sight detection unit 202 have the configuration similar to that of the line-of-sight detection unit 13 illustrated in FIG. 2 and is designed to detect the position of the collaborator's line-of-sight extended end within the display range of the collaborating-side video display unit 23 as line-of-sight position data.

The line-of-sight detection unit 202 sends out the line-of-sight position data to the collaborating-side communication unit 21 and the instructing-side video display unit 23 marks and displays the position of the collaborator's line-of-sight extended end based on the line-of-sight position data received by the instructing-side communication unit 11 within the display range.

Figure 16:
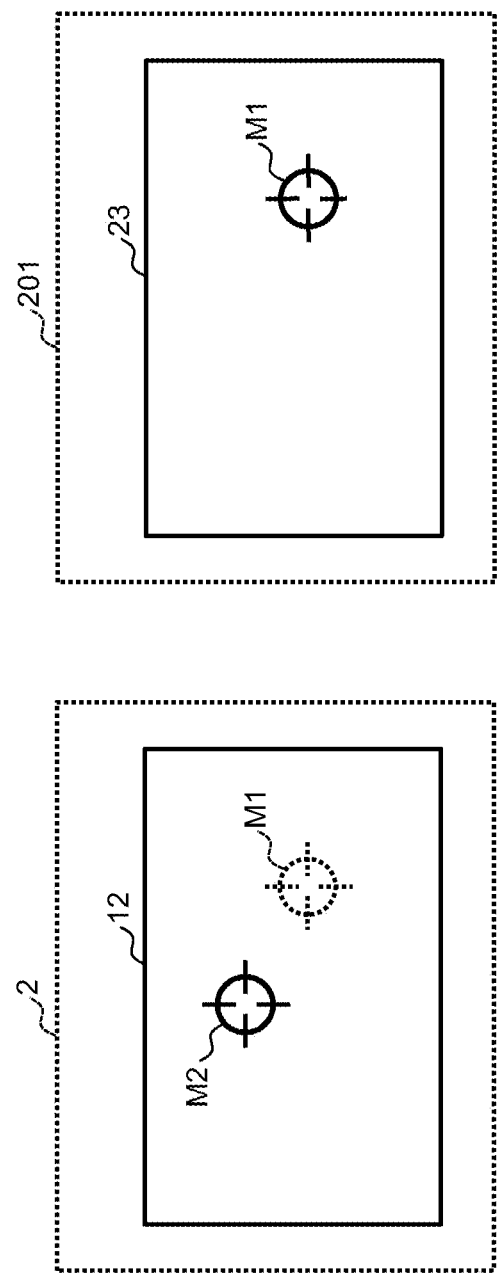
FIG. 16 is a schematic diagram for explaining mutual displaying of line-of-sight positions by video display units on a collaborating side and an instructing side according to another embodiment.

As a result, as illustrated in FIG. 16, the expert can mark and display the position of the expert's own line-of-sight end (M1) within the display range of the collaborating-side video display unit 23 and, at the same time, mark and display the position of the collaborator's line-of-sight end (M2) within the display range of the instructing-side video display unit 12, so that the collaborator and the expert can work while mutually visually checking the other party's line-of-sight position on a real-time basis.

Moreover, this embodiment has described the case where the expert instructs the collaborator in their skills as the expert's side detects the movements of the respective fingertips as the endpoints and, at the same time, the end effector 25 is mounted on the respective fingertips on the collaborator's side; however, the present invention is not limited to this example and the expert may wear endpoints, which have the same configuration (equivalent functions and structure) as that of the collaborator, on their respective fingertips so that the end effector on the collaborator's side at the remote location and the end effector on the expert's side may operate integrally. Under this circumstance, whether the expert should be prioritized or the collaborator should be prioritized can be adjusted by making it possible to interactively change the transfer ratio of the three-dimensional directional movements based on the fingers' action data D1.

Figure 17:
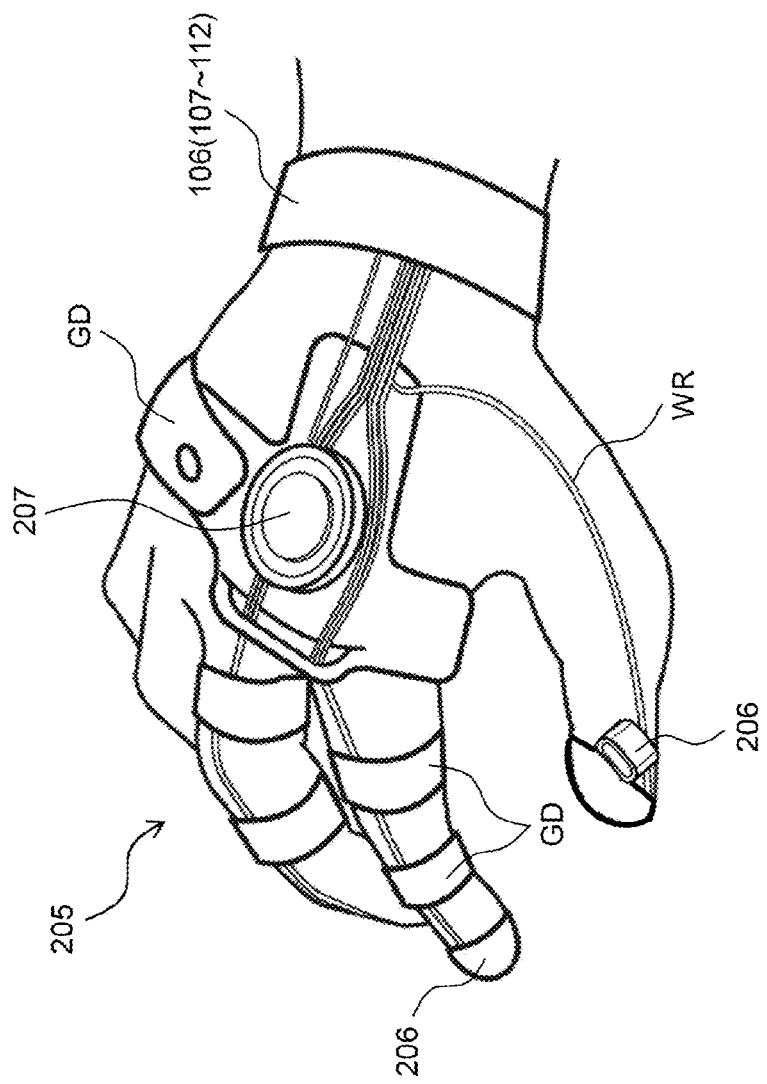
FIG. 17 is a schematic diagram illustrating the configuration of a force displacement transfer unit according to another embodiment.

An explanation will be provided about the case where force displacement transfer units having the same configuration are mounted on the expert's fingers and the collaborator's fingers, respectively. This force displacement transfer unit 205 includes an end effector 206 having a structure such that wires WR which are driven with the degree of freedom upwards, downwards, to the right, and to the left as illustrated in FIG. 17 are placed along three fingers (a thumb, an index finger, and a middle finger), thereby making it possible to guide actions of the fingertips. This end effector 206 has substantially the same structure as that of the end effector 101 configured from the linear members described earlier and illustrated in FIG. 4.

A ring-shaped light-emitting unit 207 which lights up or blinks on and off according to usage conditions is attached to a guide part GD which is wound around the back of a hand. This ring-shaped light-emitting unit 207 enables a person who is wearing it to recognize whether the expert is prioritized or the collaborator is prioritized, by making it emit the light in a light-emitting status (an luminescent color and a lighting or blinking pattern) according to the transfer ratio of interactive movements of the expert and the collaborator, or a force of the other party (the collaborator for the expert or the expert for the collaborator), or the size of displacement.

The expert can perceive the force sense to prompt each finger to perform three-dimensional actions while transferring three-dimensional directional movements based on physical feedback information of each end effector 206 on the collaborating side, which is received by the instructing-side communication unit 11 with respect to each end effector 206. Specifically speaking, the expert can perceive the collaborator's work content in response to the finger movements transferred by the expert themselves, as a force sense transfer result in the state of wearing the end effector 206, which has the same configuration as that of the collaborator, on each finger through the force displacement transfer unit 205 in a feedback manner.

Therefore, not only the expert can perceive gaps between their own instruction content and the collaborator's response content on a real-time basis, but also the respective end effectors 206 can operate integrally with the collaborator and information of the fingertips' actions can be mutually transferred interactively. It becomes possible for the expert and the collaborator to perform the same work while mutually checking how the fingertips are moved.

Figure 18A:
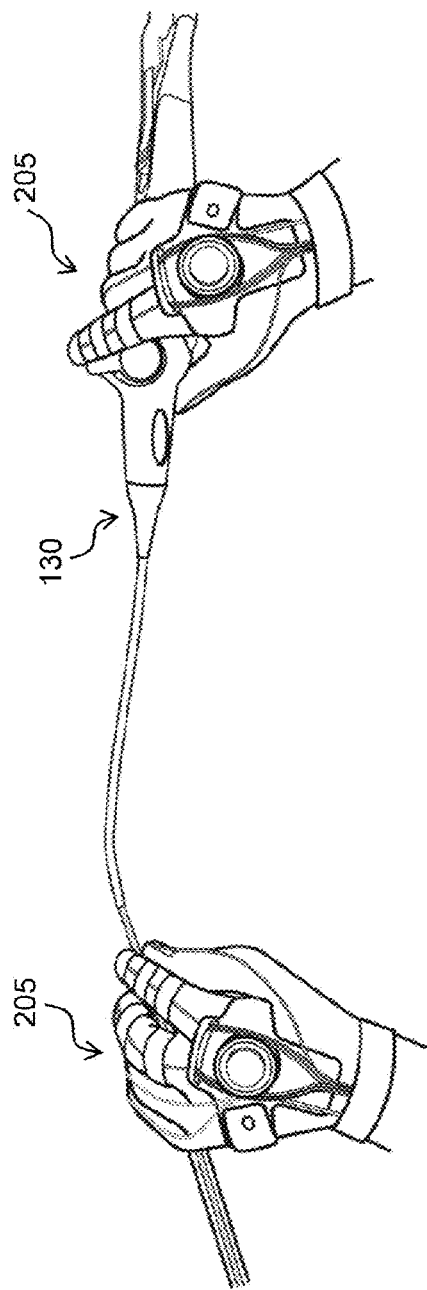
FIGS. 18A and 18B are schematic diagrams for explaining an operational status of the force displacement transfer unit in its mounted state on the collaborating side and the instructing side according to another embodiment.
Figure 18B:
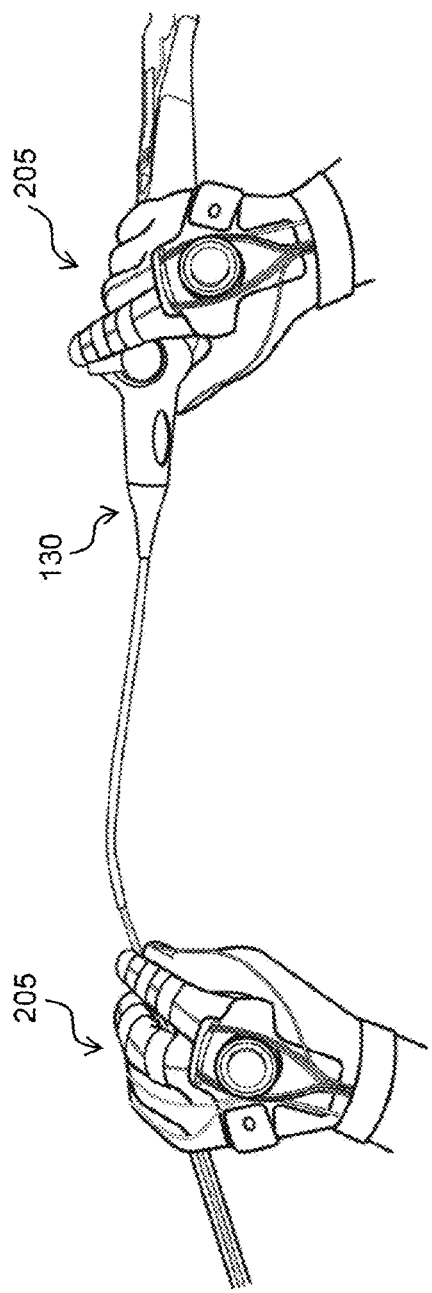

FIG. 18A and FIG. 18B illustrate a case where the expert and the collaborator perform the catheter ablation treatment while retaining the electrode catheters 130 having the same configuration in the state where they actually respectively wear the force displacement transfer unit 205 (mainly the end effectors 206) on their both hands. As a medical instructor's side (FIG. 18B) instructs a collaborating doctor's side (FIG. 18A) at a remote location, who actually gives the treatment at an actual treatment site, by operating the electrode catheter 130, it becomes possible to realize pseudo performance of "Helping Hands" (where the expert joins the collaborator and participates in the treatment) as if the expert's hands are placed over the collaborator's hands.

Furthermore, this embodiment has described the case where the expert and the collaborator use and operate the electrode catheters (work electronic instruments) 130 having the same configuration, and the case where the adjusted amount of the expert's operation content is prioritized over the operation by the collaborator and is reflected in the operation content of the electrode catheter 130; however the present invention is not limited to this example and an dedicated instrument attachment may be attached to the work electronic instrument (electrode catheter) and a plurality of pieces of operation content with the work electronic instrument may thereby be quantitatively measured via the instrument attachment.

Figure 19:
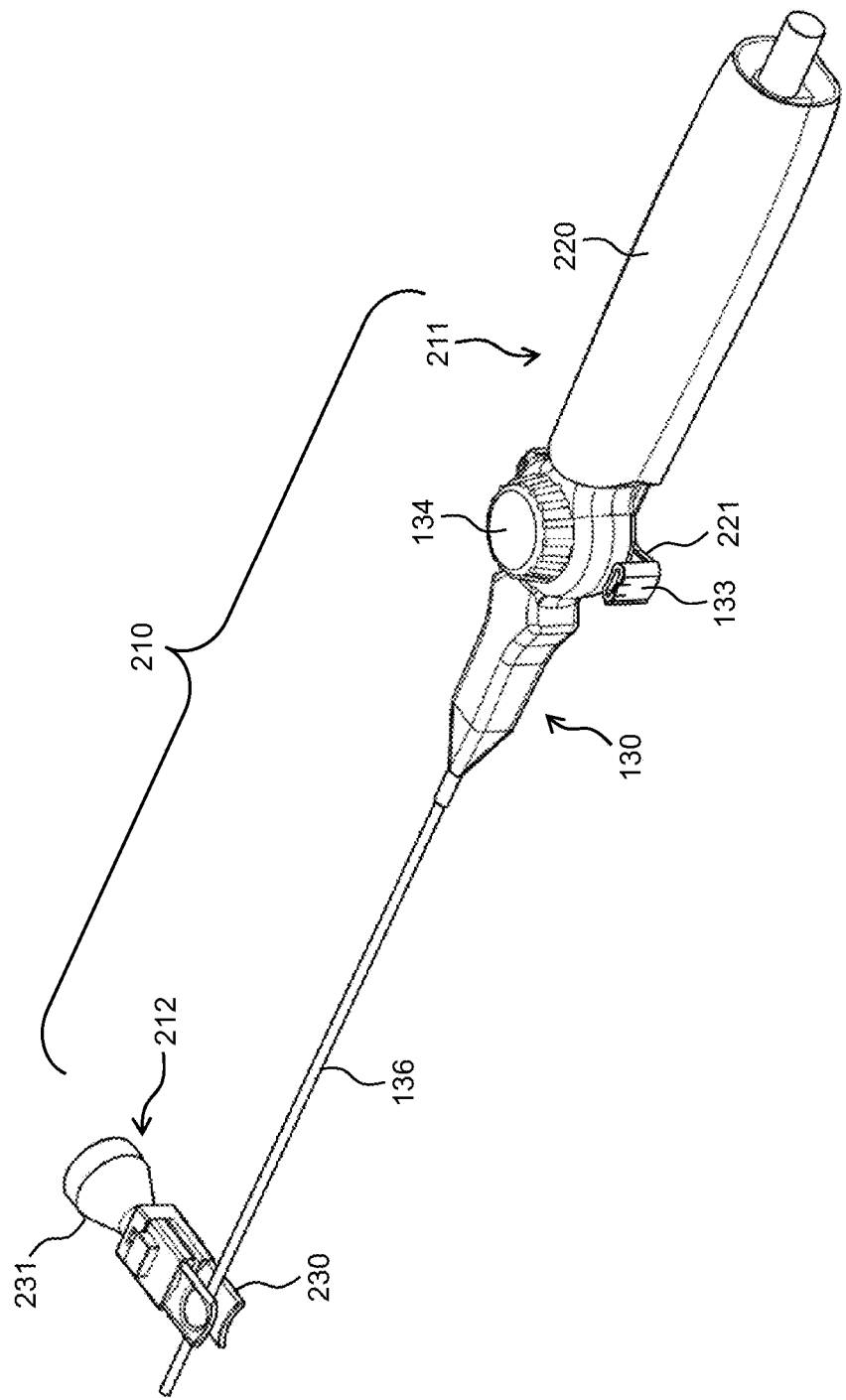
FIG. 19 is a schematic diagram illustrating a state where an instrument attachment is mounted on an electrode catheter according to another embodiment.

Specifically speaking, as illustrated in FIG. 19, an instrument attachment 210 is attached to the electrode catheter 130 in such a manner that the instrument attachment 210 is separate from the electrode catheter 130 and can be freely attached to, or detached from, the electrode catheter 130. This instrument attachment 210 includes: a handle retaining part 211 which covers the handle part 131 of the electrode catheter 130; and a shaft holding part 212 to hold the shaft 136 of the electrode catheter 130 with the fingers from above and below the shaft 136.

The handle retaining part 211 includes, as illustrated in FIG. 20B: a shell housing 220 to cover the handle part 131 of the electrode catheter 130; a lever retaining part 221 which is secured, in a freely movable manner, integrally with the lever 131 of the electrode catheter 130; a pair of wires 222 which are pulled out from both sides of the lever retaining part 221 by holding a lever rotation shaft of the lever retaining part 221 with the fingers; and a wire drive unit 223 which drives the wires 222 so as to push out or pull in only either one of the wires 222.

The shaft holding part 212 is designed as illustrated in FIG. 19 and FIG. 20B so that protruding sides of a pair of curved contact parts 230 are held with the fingers from above and below the shaft 136 to hold the shaft 136 and the force to hold the pair of curved contact parts 230 with the fingers is adjusted by the holding force adjustment unit 231.

Accordingly, by attaching the handle retaining part 211 (FIG. 20B) to the electrode catheter 130 (FIG. 20A), they can act as an integrated apparatus as illustrated in FIG. 19 and FIG. 20C, adjust the lever 133 of the electrode catheter 130, and perform specified operations involved with the shaft 136.

Figures 21A, 21B:
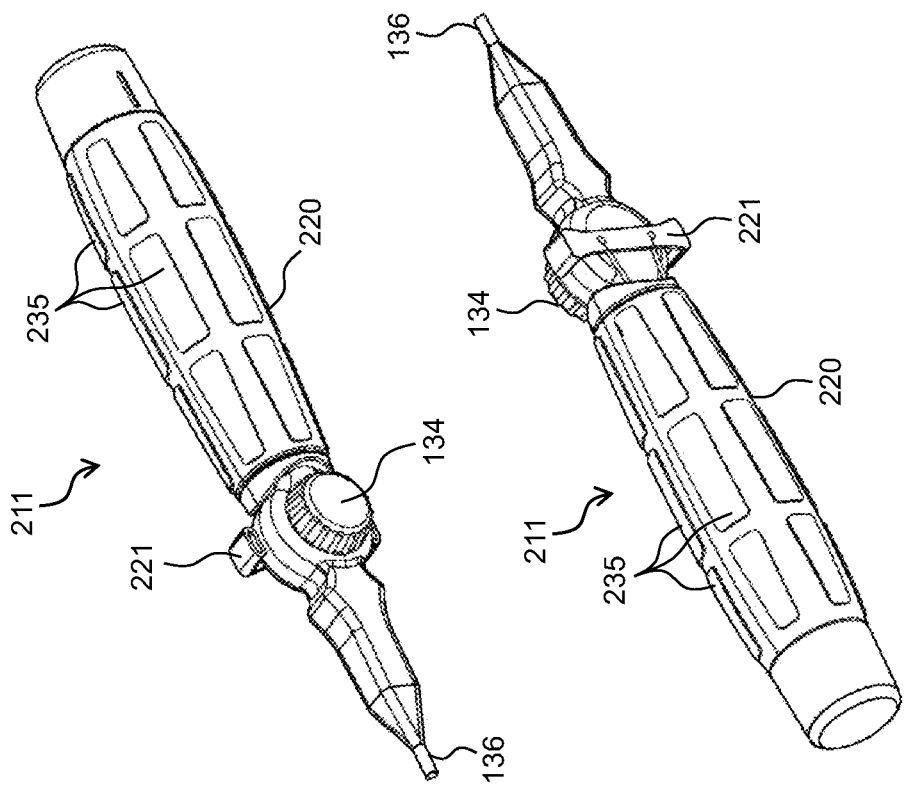
FIGS. 21A and 21B are schematic diagrams illustrating an appearance configuration of a handle retaining part of the instrument attachment illustrated in FIG. 19.

A force sense feedback imparting unit 235 is provided over the entire outer peripheral surface of the shell housing 220 of the handle retaining part 211 in this instrument attachment 210 as illustrated in FIG. 21A and FIG. 21B, so that a palm of the expert's hand or the collaborator's hand which holds the handle retaining part 211 can be made to perceive a physical force sense.

Figure 22:
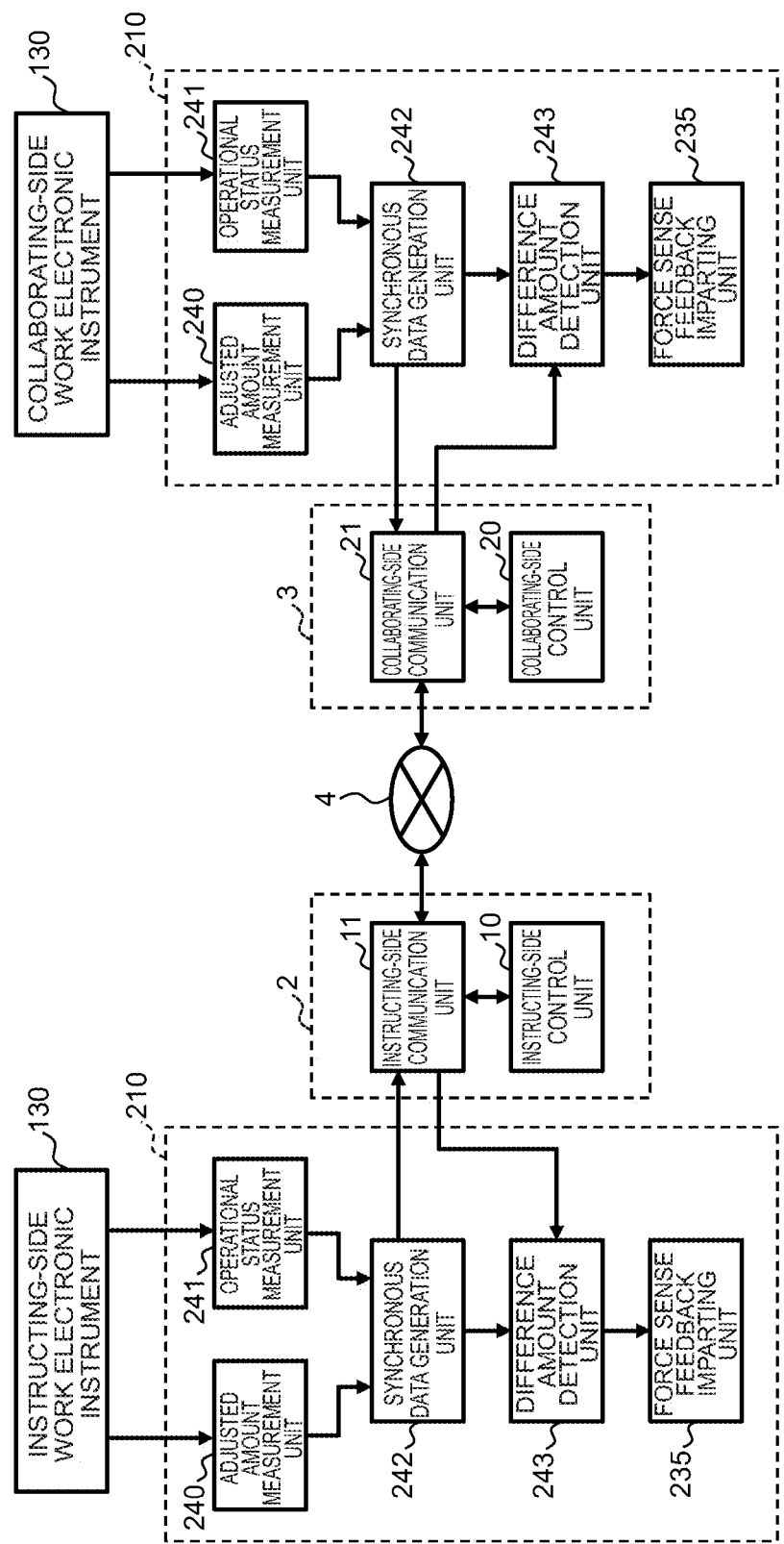
FIG. 22 is a block diagram illustrating a circuit structure of the instrument attachment.

FIG. 22 illustrates a circuit structure of the instrument attachment 210. The instrument attachment 210 includes: an adjusted amount measurement unit 240 which measures an adjusted amount by operational means capable of quantification (the lever 133, the tension knob 134, and the pair of curved contact parts 230) among the plurality of pieces of operation content; an operational status measurement unit 241 which quantifies and measures an operational status other than the operational means among the plurality of pieces of operation content; and a synchronous data generation unit 242 which generates synchronous data combined with measurement results by the adjusted amount measurement unit 240 and the operational status measurement unit 241 on the basis of that measurement results.

The operational status measurement unit 241 has an acceleration sensor and a gyro sensor (an angular velocity sensor) and is designed to dynamically measures a three-dimensional posture of the instrument attachment 210. Incidentally, the operational status measurement unit 241 may be equipped with not only inertial sensors such as the acceleration sensor and the gyro sensor, but also various sensors (physical sensors such as a photoelectronic sensor, an ultrasonic sensor, an image distinguishing sensor, a laser sensor, and a magnetic sensor) as necessary.

The synchronous data generation unit 242 mutually transmits/receives the synchronous data to/from the collaborating-side communication unit 21 for the collaborating-side information processing apparatus 3 and the instructing-side communication unit 11 for the instructing-side information processing apparatus 2 via the network 4 under control of the collaborating-side control unit 20 and the instructing-side control unit 10.

Each instrument attachment 210 of the collaborating side and the instructing side includes: a difference amount detection unit 243 that detects a difference amount of the operation content based on a data comparison result of the synchronous data between the collaborating side and the instructing side; and a force sense feedback imparting unit 235 (FIG. 21) that imparts a force sense according to the difference amount detected by the difference amount detection unit to the collaborator's hands and the expert's hands, respectively, and causes their hands to perceive the force sense in a feedback manner.

Accordingly, by mounting the instrument attachments 210 having the same configuration on the work electronic instruments (the electrode catheters 130) on the collaborating side and the instructing side, respectively, as illustrated in FIG. 23A and FIG. 23B, both the collaborator and the expert can operate the work electronic instruments while mutually perceiving the adjusted amount by the operational means and the operational status other than the above-mentioned operational means on the other side as the force sense. Particularly, the manual skills and judgments by delicate work of the fingers, which are the operational status other than the operational means of the work electronic instruments, can be also transferred as a quantitative force sense to each other.

Now, an explanation will be provided about a case as illustrated in FIG. 23A and FIG. 23B where the expert and the collaborator operate the handle retaining part 211 and the shaft holding part 212 of the instrument attachment 210 with their right and left hands, each of which is wearing the force displacement transfer unit 205. The expert uses their right hand to hold the handle retaining part 211 of the instrument attachment 210 and uses their left hand to hold the shaft holding part 212 of the instrument attachment 210.

The expert operates the lever 133 of the electrode catheter 130 via the lever retaining part 212 by holding the handle retaining part 211 with their right hand and, at the same time, holds the shaft 136 of the electrode catheter 130 via each curved contact part 230 while holding the pair of curved contact parts 230 of the shaft holding part 212 of the instrument attachment 210 with the fingertips of their left hand from above and below the pair of curved contact parts 230.

Figure 24:
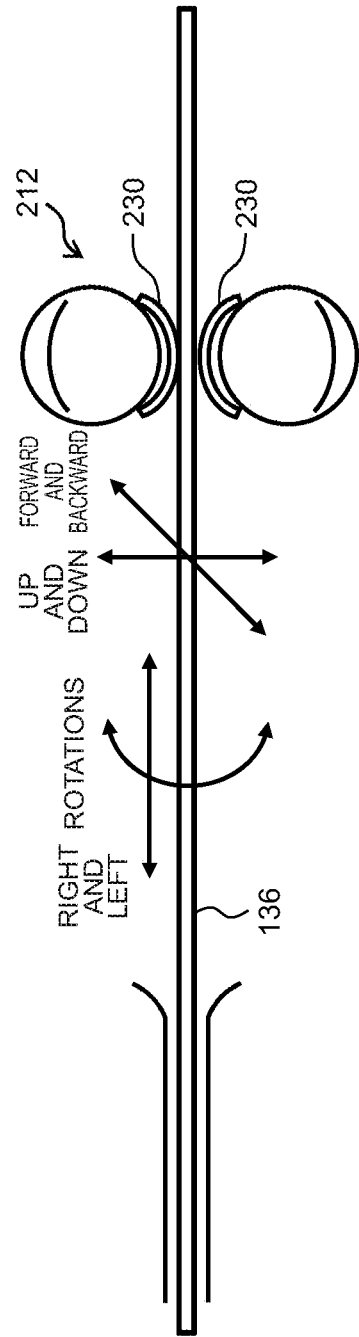
FIG. 24 is a schematic diagram for explaining movable states of a shaft by a shaft holding part of the instrument attachment according to another embodiment.

As the expert adjusts the force to hold the shaft holding part 212 with their left hand while twisting the handle retaining part 211 with their right hand around a lengthwise direction of the shaft 136 as the center of rotation and, at the same time, moving it in the lengthwise direction or a direction opposite thereto, thereby it is possible to adjust a bending state of the top end to a very fine level while making fine adjustments of the degree of twisting the shaft 136 (FIG. 24).

Such manual skills are skills which are difficult to transfer from only the end effector 206 of the force displacement transfer unit 205, so that the operation content can be quantified by using the instrument attachment 210 which is specific to the work electronic instrument (the electrode catheter 130).

Furthermore, the aforementioned embodiment has described the case where the wire drive type of the handle retaining part 211 of the instrument attachment 210 as illustrated in FIG. 20B is applied; however, the present invention is not limited to this example and various drive types may be applied if only the actuator output can be transferred to the lever 133 of the electrode catheter 130 and rotate it.

Figure 25A:
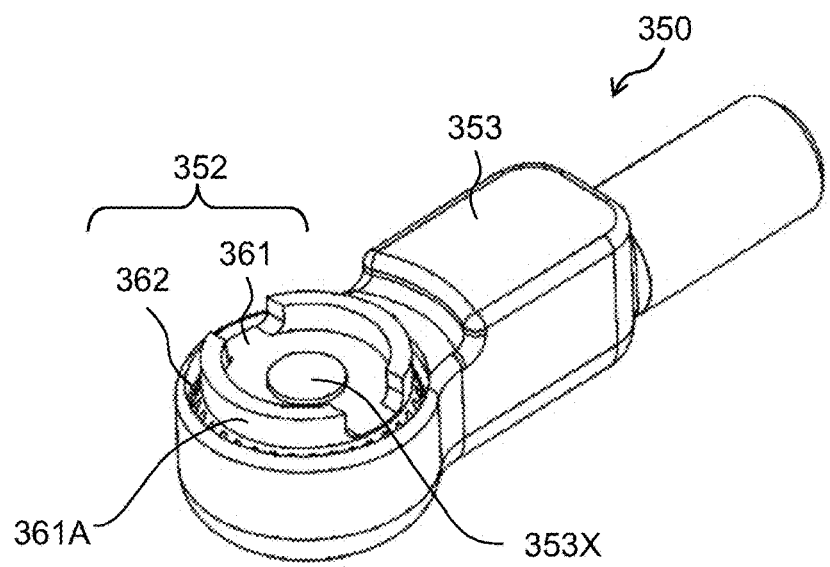
FIGS. 25A to 25C are perspective views and inner configuration diagrams illustrating the configuration of a handle retaining part according to another embodiment.
Figure 25B:
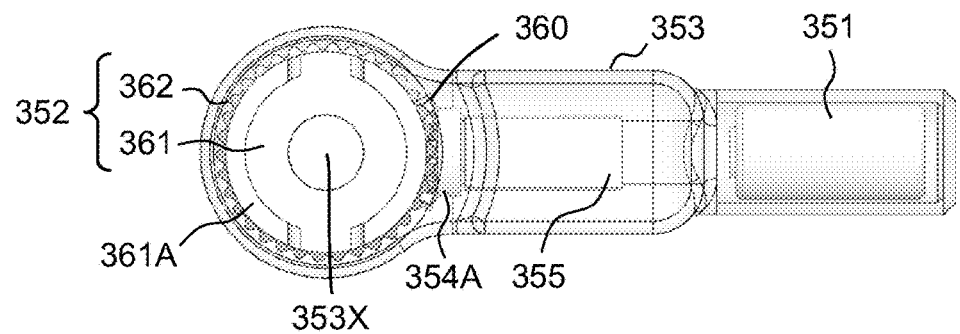
Figure 25C:
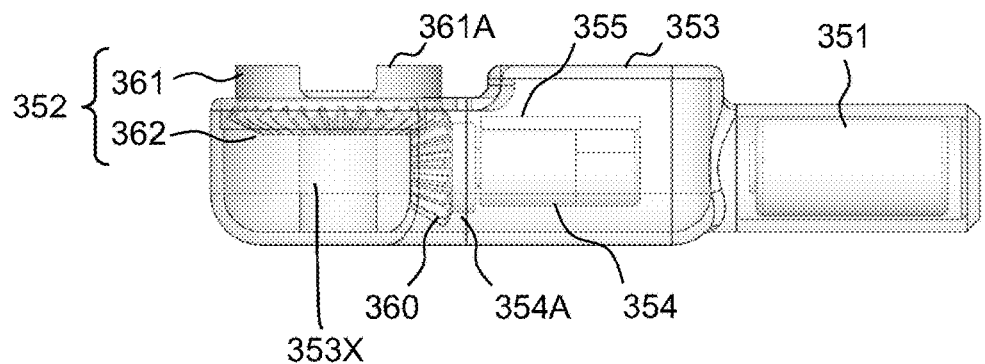

For example, a handle retaining part 350 illustrated in FIG. 25A to FIG. 25C is of a portable unit type and includes a battery 351, which is built in its one end, and a unit housing 353 from which a lever retaining part 352 is exposed in a freely rotatable manner in the other end. The unit housing 353 includes an actuator 354 which is built therein and to which a driving electric power is supplied from the battery 351; and a first bevel gear 360 which serves as the center of an output shaft 354A of the actuator 354 is secured to the output shaft 354A.

A drive unit 355 equipped with a radio communication function is connected to the actuator 354 and the drive unit 355 is designed to be capable of causing the actuator 354 to generate a driving force according to the operation content by the collaborator and the expert under control of the collaborating-side control unit 20 and the instructing-side control unit 10.

The lever retaining part 352 is configured such that a disc member 361 on which a pair of arc-shaped protrusions 361A for engaging with, and retaining, the lever 133 of the electrode catheter 130 is formed, and a second bevel gear 362 which is firmly fixed to the disc member 361 are attached to a fixed axle 353X of the unit housing 353 in a freely rotatable manner. The first bevel gear 360 and the second bevel gear 362 of the lever retaining part 352 engage with each other in such a manner that their rotation axes orthogonally intersect with each other, so that the output of the actuator 354 is transferred via the first bevel gear 360 and the second bevel gear 362 to the disc member 361.

Figure 26A:
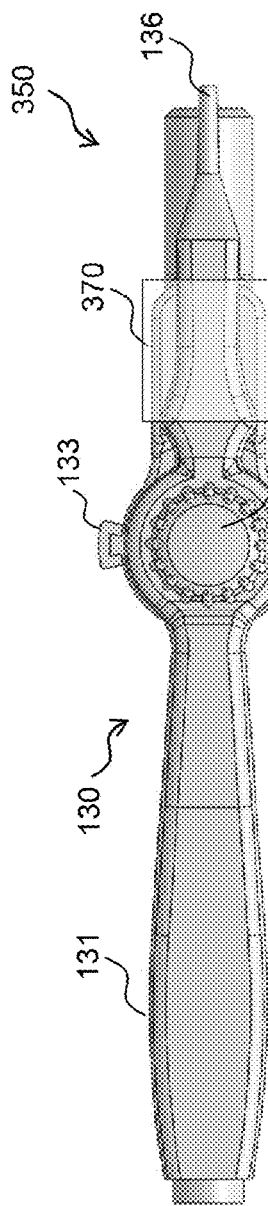
FIGS. 26A to 26C are front views and a side views illustrating a state where the handle retaining part illustrated in FIG. 25 is mounted on the electrode catheter.
Figure 26B:
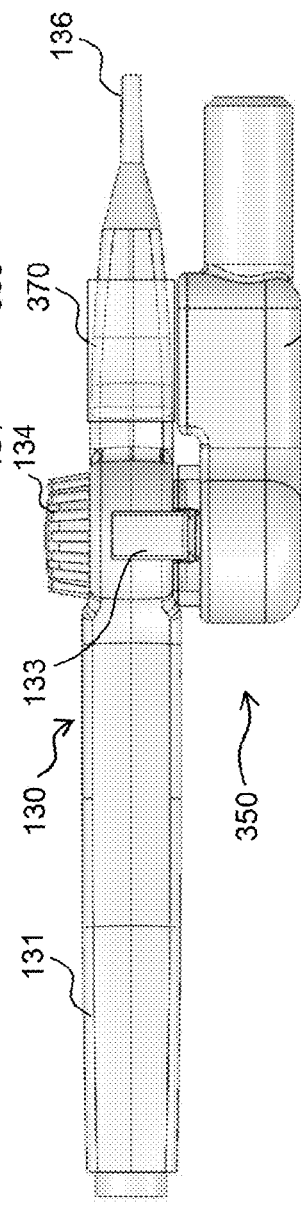
Figure 26C:
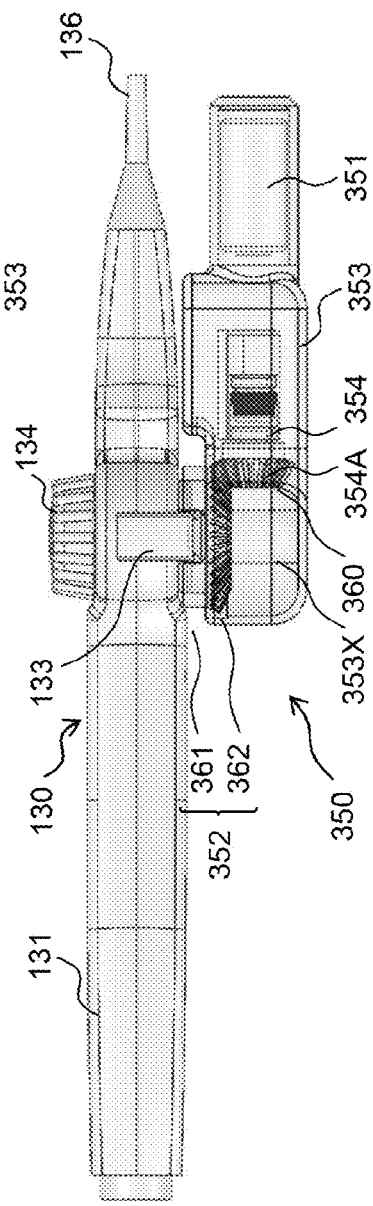

Referring to FIG. 26A to FIG. 26C, a belt-shaped holder 370 is used to attach the handle retaining part 350 to the lever 133 of the electrode catheter 130 and it is thereby possible to adjust the lever 133 of the electrode catheter 130 as an integrated apparatus.

Figure 27A:
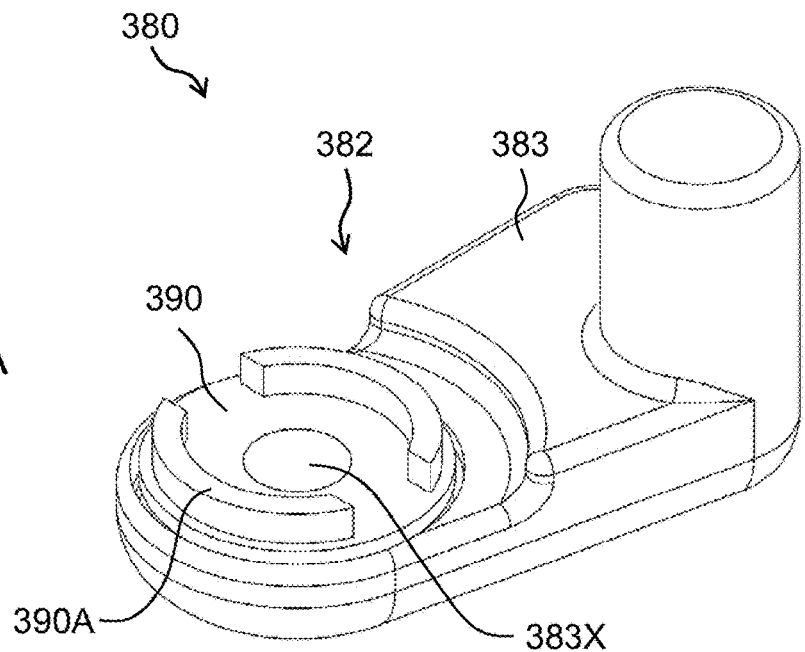
FIGS. 27A and 27B are perspective views and inner configuration diagrams illustrating the configuration of a handle retaining part according to another embodiment.
Figure 27B:
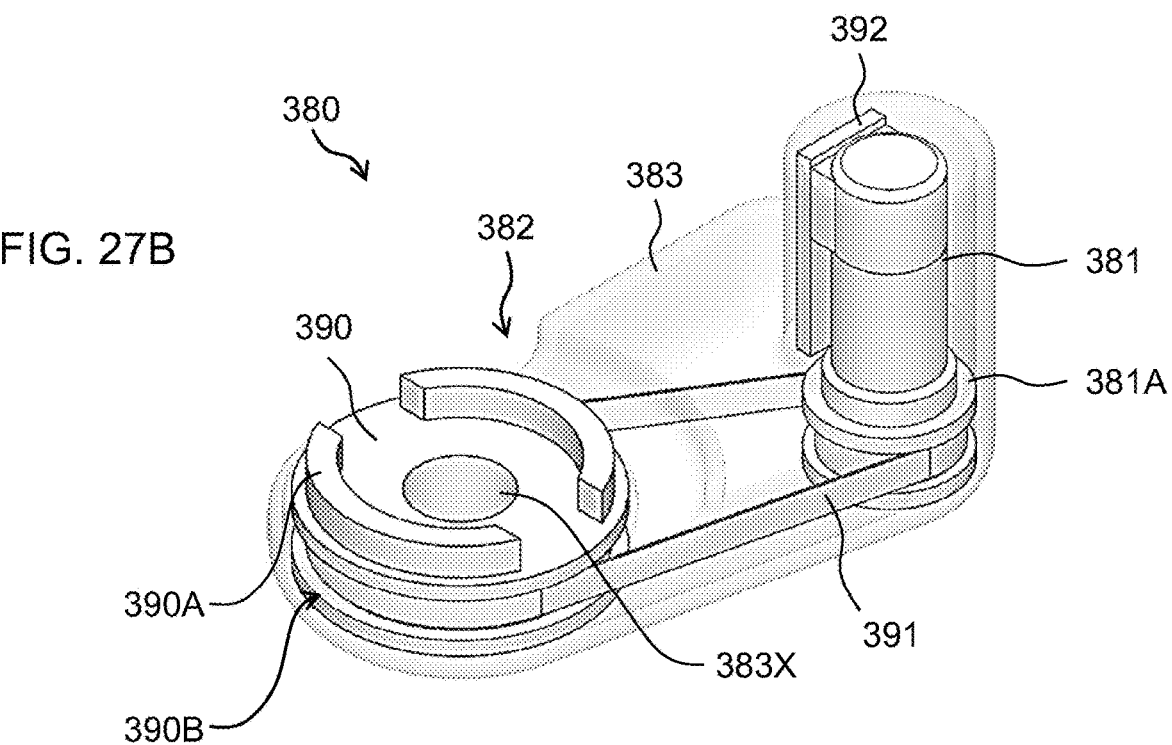

Furthermore, for example, a handle retaining part 380 illustrated in FIG. 27A and FIG. 27B is of a portable unit type and includes an actuator 381, which is built in its one end, and a unit housing 383 from which a lever retaining part 382 is exposed in a freely rotatable manner in the other end.

The lever retaining part 382 is configured such that a pair of arc-shaped protrusions 390A are formed to engage with, and retain, the lever 133 of the electrode catheter 130 and a disc member 390, which has a groove 390B with a specified width formed along its outer periphery, is attached to a fixed axle 383X of the unit housing 383.

A driving belt 391 is wound around an output shaft 381A of the actuator 381 and the groove 390B around the outer periphery of the disc member 390; and the output shaft 381A of the actuator 381 is transferred to the disc member 390 via the driving belt 391.

A drive unit 392 equipped with a radio communication function is connected to the actuator 381 and the drive unit 392 is designed to be capable of causing the actuator 381 to generate a driving force according to the operation content by the collaborator and the expert under control of the collaborating-side control unit 20 and the instructing-side control unit 10.

Figure 28A:
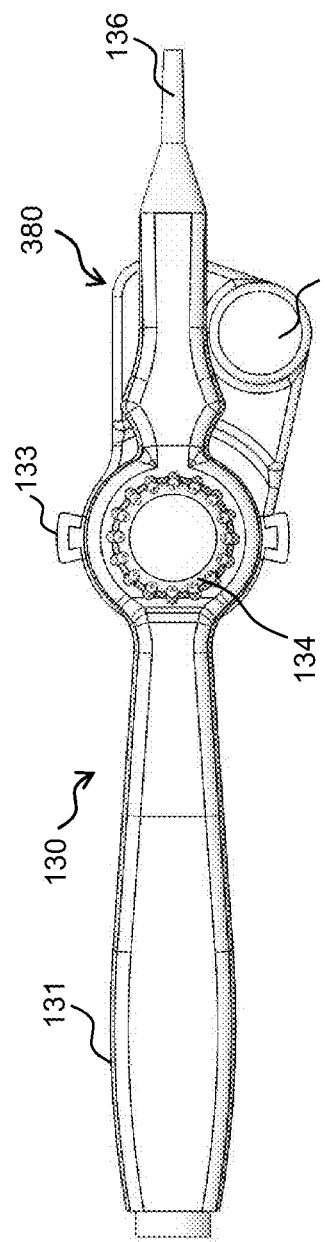
FIGS. 28A to 28C are front views and side views illustrating a state where the handle retaining part illustrated in FIG. 27 is mounted on the electrode catheter.
Figure 28B:
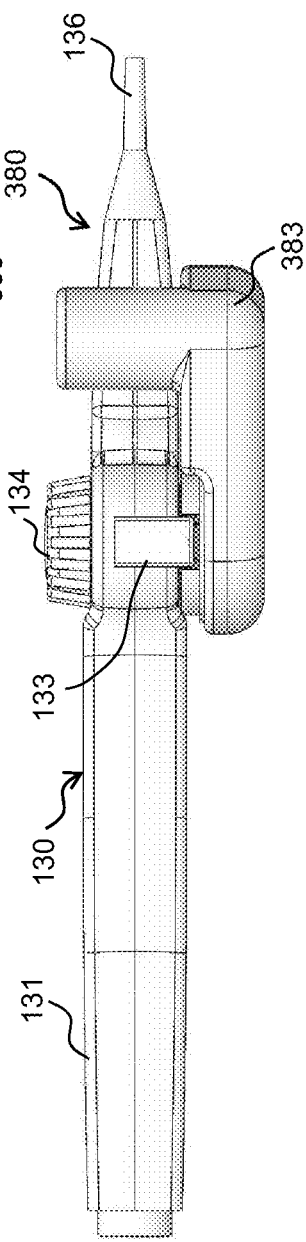
Figure 28C:
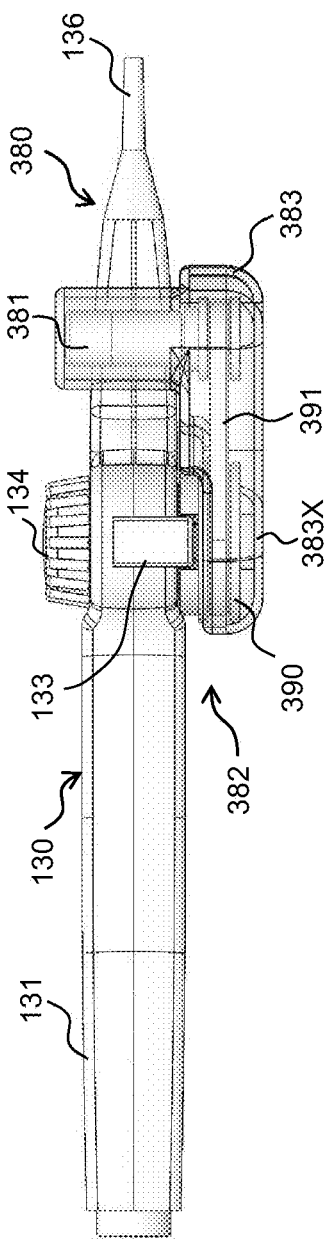

Referring to FIG. 28A to FIG. 28C, the handle retaining part 380 is attached to the lever 133 of the electrode catheter 130 and it is thereby possible to adjust the lever 133 of the electrode catheter 130 as an integrated apparatus.

Furthermore, this embodiment has described the case where the data management apparatus 40 associates the series of action content of the expert and the series of action content of the collaborator regarding the work with each other as the instructing-side work data and the collaborating-side work data and stores them in the work data storage unit 150; however, the present invention is not limited to this example and various kinds of information associated with the work (the surgical operation for the catheter ablation treatment), that is, various recordable information regarding the expert's manual skills and instructions and a subject (patient) during the work (treatment) (for example, videos and images of the surroundings and working conditions associated with time axis information, and information regarding sounds, a physical state, a treatment state, and a body), information associated with the collaborator's work (implementation of the treatment), and environmental information including temperatures and acoustics may also be stored in the work data storage unit 150.

Moreover, with the data management apparatus 40, all pieces of information obtained from the expert can be also utilized as information for promoting deep learning by artificial intelligence. Furthermore, even when the expert is absent, the collaborator practices by repetitions to enhance their own skills on work (treatment) by reproducing the results of work (treatment) conducted in the past as many times as possible on the basis of various information recorded in the data management apparatus 40, so that it can be also utilized as a system capable of training to develop experts.

Furthermore, this embodiment has described the case where the expert and the collaborator use the electrode catheters (the work electronic instruments) 130 having the same configuration and quantitatively measure the plurality of pieces of operation content with the work electronic instruments via the aforementioned instrument attachments; however, the present invention is not limited to this example and the collaborating-side instrument attachment itself may be robotized to be operable independently of the collaborator's operations and the operation content of the instructing-side instrument attachment may be directly transferred as the operation content of the collaborating-side instrument attachment.

A. When Expert Operates Work Electronic Instrument as it is

Figure 29:
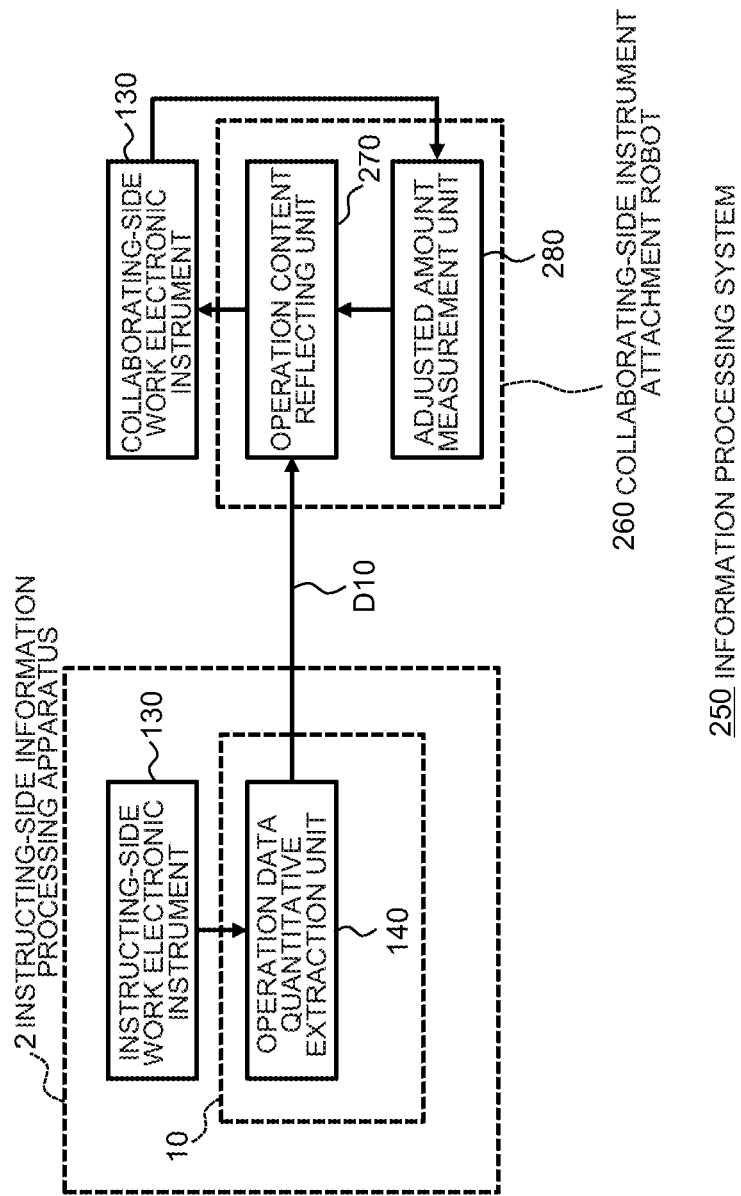
FIG. 29 is a block diagram for explaining information transfer on the expert's side and the collaborator's side regarding the operation of an electrode catheter according to another embodiment.

Referring to FIG. 29 in which the same reference numerals as those in FIG. 12 are assigned to parts corresponding to those in FIG. 12, this information transfer system 250 is designed so that when the expert performs specific work, the expert transfers their skills regarding the work to the collaborating side via the network 4 while operating the instructing-side work electronic instrument 130 with their own fingertips. The collaborating side wears a collaborating-side instrument attachment robot 260 which has functionally substantially the same configuration as that of the aforementioned instrument attachment 210, but it has a different circuit structure of a signal processing system as that of the instrument attachment 210.

The instructing-side information processing apparatus 2 includes: the operation data quantitative extraction unit 140 that extracts an adjusted amount by an operation capable of quantification, as instructing-side adjustment data D10, among the operation content of the instructing-side work electronic instrument 130 under integrated control of the instructing-side control unit 10; and the instructing-side communication unit 11 (which is omitted in FIG. 29) that transmits the instructing-side adjustment data D10.

The collaborating-side instrument attachment robot 260 includes: the collaborating-side communication unit 21 (which is omitted in FIG. 29) which is attached in a freely attachable/detachable manner to the collaborating-side work electronic instrument 130 having the same configuration as that of the instructing-side work electronic instrument 130 and receives the instructing-side adjustment data D10 transmitted from the instructing-side communication unit 11 via the network 4; and an operation content reflecting unit 270 which causes an adjusted amount of the relevant operation content to be reflected in the operation content of the collaborating-side work electronic instrument 130 on the basis of the instructing-side adjustment data D10.

Moreover, the collaborating-side instrument attachment robot 260 includes an adjusted amount measurement unit 280 which measures an adjusted amount by an operation capable of quantification among the plurality of pieces of operation content with the collaborating-side work electronic instrument 130. The operation content reflecting unit 270 calibrates and corrects the adjusted amount of the relevant operation content with the collaborating-side work electronic instrument 130 on the basis of the adjusted amount which is fed back from the adjusted amount measurement unit 280.

Accordingly, with the information transfer system 250, the collaborating-side instrument attachment robot 260 can execute actions of the same operation content as the relevant operation content with respect to the collaborating-side work electronic instrument 130 on a real-time basis in synchronization with the timing when the operation content of the instructing-side work electronic instrument 130 by the expert is transferred.

As a result, the collaborating-side instrument attachment robot 260 can indirectly reproduce the expert's skills which are the tacit knowledge regarding the operation content of the instructing-side work electronic instrument 130 by the expert with very high accuracy on a real-time without having the operations performed with the collaborator's fingers on the collaborating side.

Figure 30:
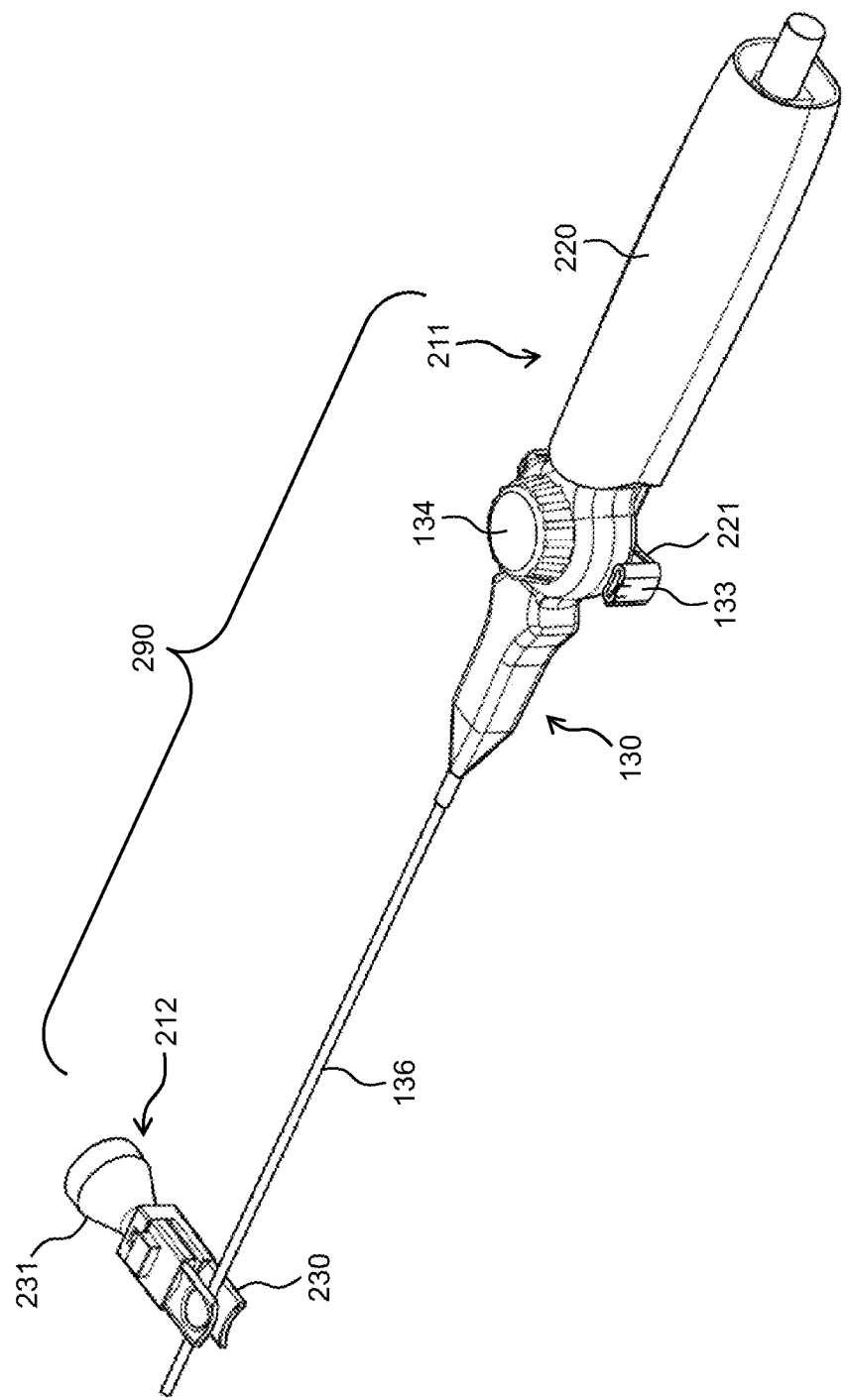
FIG. 30 is a schematic diagram illustrating a state where an instrument attachment is mounted on an electrode catheter according to another embodiment.

B. When Expert Operates Work Electronic Instrument in Instrument-Attachment-Mounted State Referring to FIG. 30 in which the same reference numerals as those in FIG. 19 are assigned to parts corresponding to those in FIG. 19, the collaborating-side instrument attachment robot 290 has functionally substantially the same configuration as that of the aforementioned instrument attachment 210, except that the force sense feedback imparting unit 235 is excluded and a circuit of a signal processing system is different.

This information transfer system 300 (described later regarding FIG. 31) is designed so that when the expert performs specific work, the expert transfers their skills regarding the work to the collaborating side via the network 4 while operating the instructing-side work electronic instrument 130 with their own fingertips.

The collaborating-side instrument attachment robot 290 includes: a handle retaining part 211 which is separate from, and can be attached in a freely attachable/detachable manner to, the aforementioned electrode catheter (the instructing-side work electronic instrument) 130 (FIG. 20A) and covers the handle part 131 of the electrode catheter 130; and a shaft holding part 212 to hold the shaft 136 of the electrode catheter 130 with the fingers from above and below the shaft 136.

The handle retaining part 211 includes: a shell housing 220 to cover the handle part 131 of the electrode catheter 130; a lever retaining part 221 which is secured, in a freely movable manner, integrally with the lever 131 of the electrode catheter 130; a pair of wires 222 which are pulled out from both sides of the lever retaining part 221 by holding a lever rotation shaft of the lever retaining part 221 with the fingers; and a wire drive unit 223 which drives the wires 222 so as to push out or pull in only either one of the wires 222.

The shaft holding part 212 is designed so that protruding sides of a pair of curved contact parts 230 are held with the fingers from above and below the shaft 136 to hold the shaft 136 and the force to hold the pair of curved contact parts 230 with the fingers is adjusted by the holding force adjustment unit 231.

Accordingly, by attaching the collaborating-side instrument attachment robot 290 to the electrode catheter 130, they can act as an integrated apparatus, automatically operate the lever 133 of the electrode catheter 130, and perform specified operations involved with the shaft 136.

Furthermore, with the collaborating-side instrument attachment robot 290, each of the handle retaining part 211 and the shaft holding part 212 may be equipped with various physical sensors (physical sensors such as a photoelectronic sensor, an ultrasonic sensor, an image distinguishing sensor, a laser sensor, and a magnetic sensor) including an acceleration sensor and a gyro sensor (angular velocity sensor). In this embodiment, for example, a 6-axis motion sensor which is composed of a 3-axis acceleration sensor and a 3-axis angular velocity sensor (gyro sensor) is mounted as a physical sensor.

Figure 31:
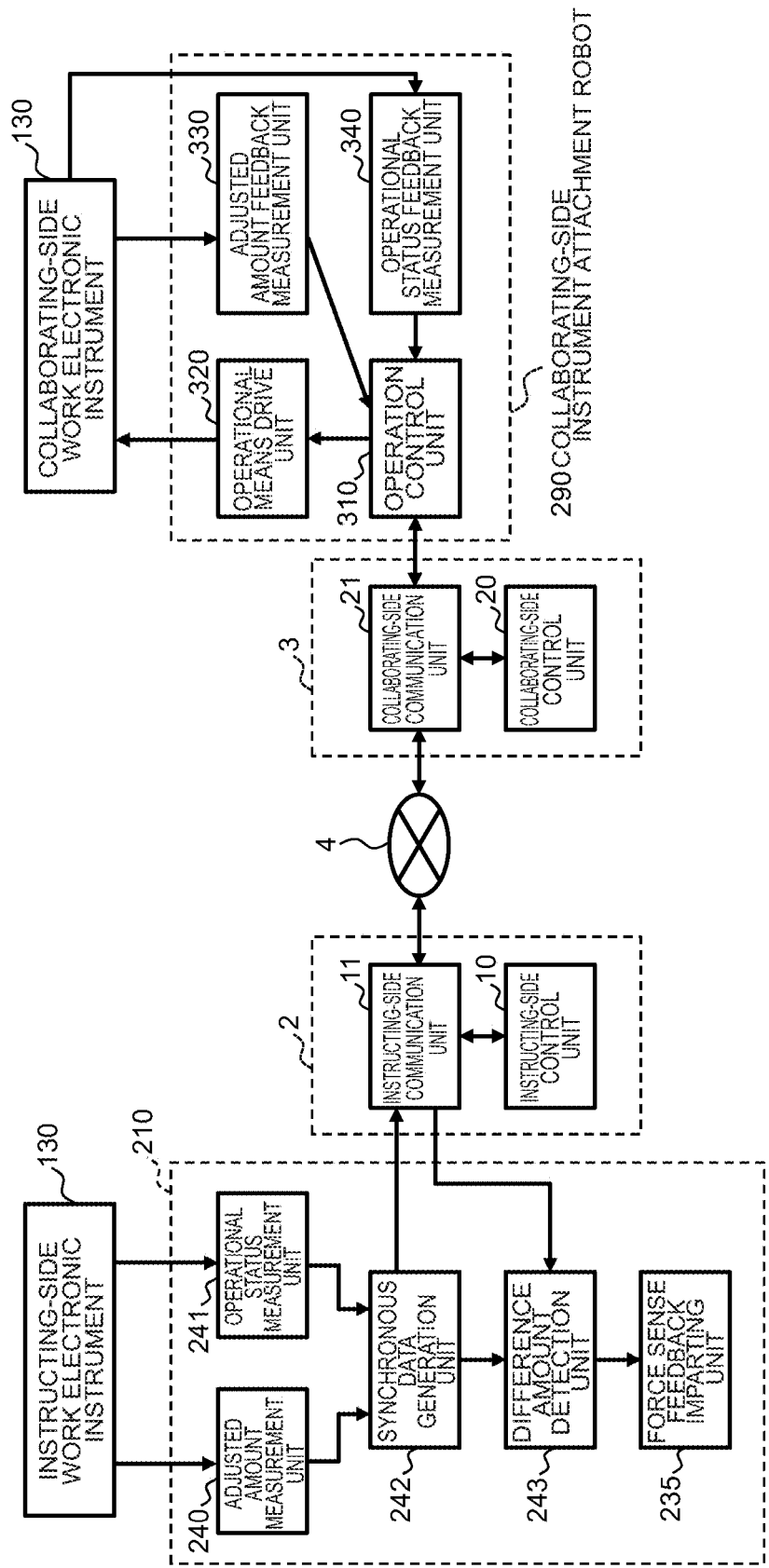
FIG. 31 is a block diagram illustrating a circuit structure of a collaborating-side instrument attachment robot.

Referring to FIG. 31 in which the same reference numerals as those in FIG. 22 are assigned to parts corresponding to those in FIG. 22, the instructing-side instrument attachment 210 includes: the adjusted amount measurement unit 240 which is attached in a freely attachable/detachable manner to the instructing-side work electronic instrument 130 and measures an adjusted amount by operational means capable of quantification among the plurality of pieces of operation content; the operational status measurement unit 241 which quantifies and measures an operational status other than the operational means among the plurality of pieces of operation content; the synchronous data generation unit 242 which generates synchronous data combined with measurement results by the adjusted amount measurement unit 240 and the operational status measurement unit 241 on the basis of that measurement results; and the instructing-side communication unit 11 which transmits the synchronous data.

The collaborating-side instrument attachment robot 290 includes: the collaborating-side communication unit 21 which is attached in a freely attachable/detachable manner to the collaborating-side work electronic instrument 130 having the same configuration as that of the instructing-side work electronic instrument 130 and receives the synchronous data transmitted from the instructing-side communication unit 11 via the network 4; an operation control unit 310 which generates, as a control signal, the adjusted amount of each operational means based on the synchronous data and the operation timing of these operational means; and an operational means drive unit 320 which drives each operational means on the basis of the control signal by the operation control unit 310.

The operation control unit 310 extracts the adjusted amount with respect to the operational means capable of quantification (the lever 133, the tension knob 134, and the pair of curved contact parts 230) among the plurality of pieces of operation content, and the operation timing of these operational means from the synchronous data and sends them as the control signal to the operational means drive unit 320.

The operational means drive unit 320 is composed of the wire drive unit 223 for the handle retaining part 211 and the holding force adjustment unit 231 for the shaft holding part 212 and drives the corresponding operational means on the basis of the control signal from the operation control unit 310.

Moreover, the collaborating-side instrument attachment robot 290 includes an adjusted amount feedback measurement unit 330 which measures the adjusted amount by the operational means capable of quantification among the plurality of pieces of operation content with the collaborating-side work electronic instrument 130. The operation control unit 320 calibrates and corrects the adjusted amount of the operational means on the basis of the adjusted amount which is fed back from the adjusted amount feedback measurement unit 330.

Furthermore, the collaborating-side instrument attachment robot 290 includes an operational status feedback measurement unit 340 which quantifies and measures the operational status other than the operational means among the plurality of pieces of operation content with the collaborating-side work electronic instrument 130.

Also with this collaborating-side instrument attachment robot 290, each of the handle retaining part 211 and the shaft holding part 212 is equipped with various physical sensors (physical sensors such as a photoelectronic sensor, an ultrasonic sensor, an image distinguishing sensor, a laser sensor, and a magnetic sensor) including an acceleration sensor and a gyro sensor (angular velocity sensor). In this embodiment, for example, a 6-axis motion sensor which is composed of a 3-axis acceleration sensor and a 3-axis angular velocity sensor (gyro sensor) is mounted as a physical sensor.

Under this circumstance, an example of the operational status other than the operational means among the plurality of pieces of operation content can be, as illustrated in FIG. 24 described earlier, the operational status where the expert adjusts the force to hold the shaft holding part 212 with their left hand while twisting the handle retaining part 211 with their right hand around a lengthwise direction of the shaft 136 as the center of rotation and, at the same time, moving it in the lengthwise direction or a direction opposite thereto, thereby adjusting a bending state of the top end to a very fine level while making fine adjustments of the degree of twisting the shaft 136.

Accordingly, the manual skills and judgments by the delicate work with the fingers, which are the operational status other than the operational means of the work electronic instrument, are also quantified on the basis of the detection results of the physical sensors by associating the mutual operational status between the operational means with each other on a real-time basis.

The operation control unit 310 generates a measured amount (the detection results of the physical sensors) of the operational status other than the operational means based on the synchronous data by including the measured amount in a control signal and transmits the control signal to external equipment (which is not illustrated in drawings) which operates in cooperation with the collaborating-side work electronic equipment 130, via the collaborating-side communication unit 21.

The operation control unit 320 generates calibration data indicating a result of comparison between the measured amount of the operational status which is fed back from the operational status feedback measurement unit 340 via the external equipment and the collaborating-side work electronic instrument 130, and the measured amount of the operational status of the instructing side.

This external equipment is composed of a robot arm (which is not illustrated in drawings) which retains the handle retaining part 211 and the shaft holding part 212, respectively, and is designed to detect a three-dimensional posture state by associating the mutual action status of the wire drive unit 223 for the handle retaining part 211 and the holding force adjustment unit 231 for the shaft holding part 212 on a real-time basis.

The action status of these operational means can be calibrated and corrected by the external equipment by transmitting the calibration data from the collaborating-side instrument attachment robot 290 to this external equipment.

As the external equipment, equipment other than the robot arm, which has the structure other than that of the robot arm, may be applied as long as it can detect the mutual three-dimensional action status between the operational means with the collaborating-side instrument attachment robot 290 precisely and with high accuracy.

Accordingly, with the information transfer system 300, the collaborating-side instrument attachment robot 290 can execute actions of the same operation content as that of the instructing-side work electronic instrument 130 by the expert on the collaborating-side work electronic instrument 130 on a real-time basis in synchronization with the timing when the operation content of the instructing-side work electronic instrument 130 by the expert is transferred via the instrument attachment 210.

Under this circumstance, the collaborating-side instrument attachment robot 290 can detect not only the operational status by the operational means capable of quantification, but also the operational status other than the operational means (mutual three-dimensional action status between the operational means) by the external equipment precisely and with high accuracy on a real-time basis.

As a result, the collaborating-side instrument attachment robot 290 can indirectly reproduce the expert's skills which are the tacit knowledge regarding the operation content of the instructing-side work electronic instrument 130 by the expert with very high accuracy on a real-time basis without having the operations performed with the collaborator's fingers on the collaborating side. Furthermore, all pieces of information regarding the operation content which can be obtained from the expert can be also utilized as information for promoting learning of artificial intelligence and be also expanded as a robotized next generation treatment system.

Figures 32A, 32B:
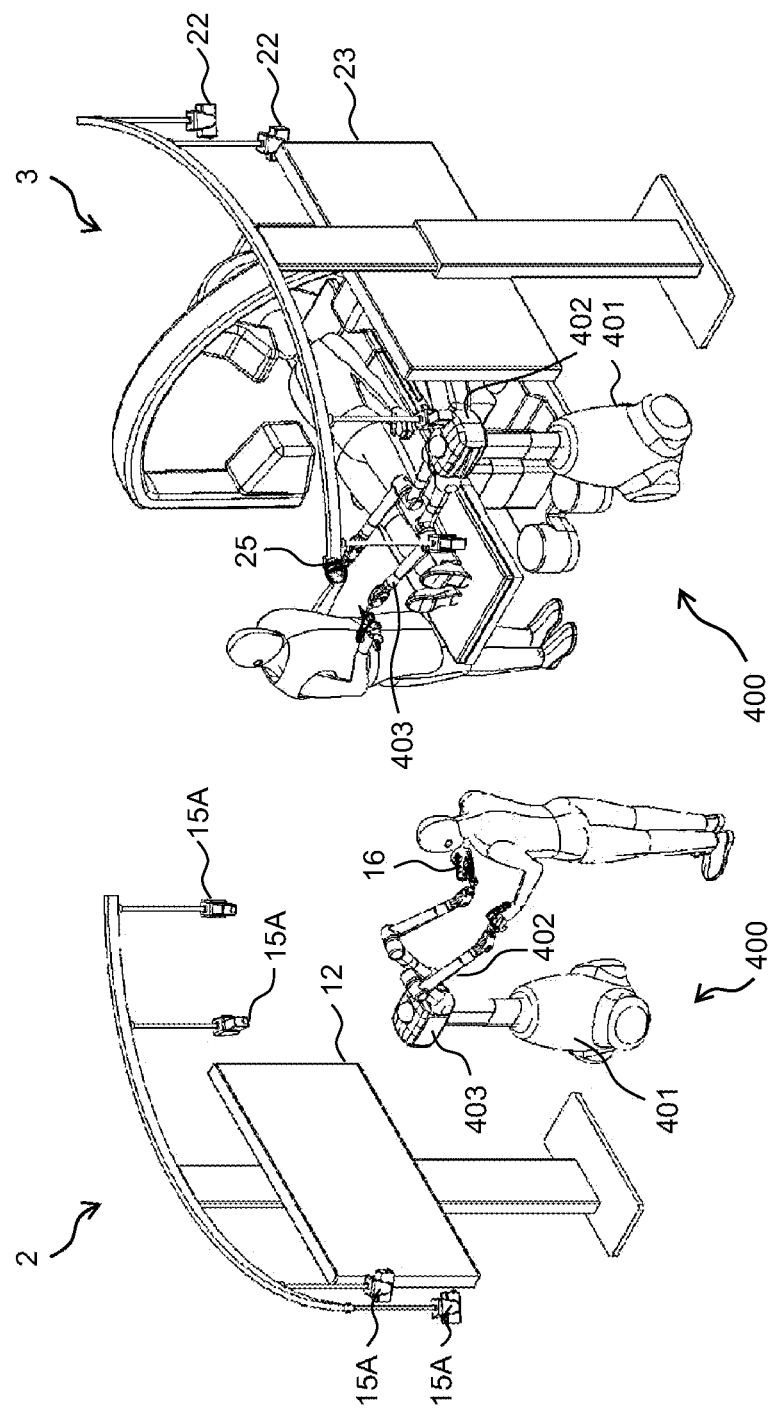
FIGS. 32A and 32B are schematic diagrams illustrating a state where self-propelled robots are located on the expert's side and the collaborator's side.

Incidentally, as the external equipment which operates in cooperation with the aforementioned collaborating-side work electronic equipment 130, for example, a self-propelled robot 400, as illustrated in FIG. 32A and FIG. 32B in which the same reference numerals as those in FIG. 1 are assigned to parts corresponding to those in FIG. 1, may be located on each of the expert's side (the instructing-side information processing apparatus 2) and the collaborator's side (the collaborating-side information processing apparatus 3).

This self-propelled robot 400 is a two-wheel-drive type mobile body which runs on a floor face autonomously or according to external operations and includes: a running base 401 which causes the robot body to run in a desired direction by rotationally driving a plurality of driving wheels simultaneously or independently; an arm support 403 which supports an end of an arm unit 402 having at least one (for example, two) articulated mechanism and is coupled to an upper part of the running base 401 in a freely rotatable manner relative to the running base and is integrated with the arm unit 402 with a vertical direction as the center of rotation.

Regarding the self-propelled robot 400, the inventor of the present application has filed a patent application (Japanese Patent Application No. 2019-29203) as an autonomously movable self-propelled robot, so that an explanation of its detailed configuration is omitted.

On the expert's side, the handle retaining part 211 and the shaft holding part 212 of the instrument attachment 210 are respectively coupled to two arm units 402 of the self-propelled robot 400 (FIG. 32A). As the expert operates the instructing-side work electronic equipment 130 by using their own fingertips, a top end of the arm unit 402 can be moved in conformity with movements of the expert's fingertips.

On the collaborating side, the handle retaining part 211 and the shaft holding part 212 of the collaborating-side instrument attachment robot 260, 290 are respectively coupled to the two arm units 402 of the self-propelled robot 400 (FIG. 32B). With the self-propelled robot 400 on the collaborator's side, the two arm units 402 respectively execute the same three-dimensional actions as those of the corresponding arm unit(s) 402 of the self-propelled robot 400 on the expert's side.

As a result, the self-propelled robot 400 on the collaborator's side can cause the operational status by the expert's fingertips to be reflected in the self-propelled robot 400 on the expert's side precisely and with high accuracy on a real-time basis.

Figure 33:
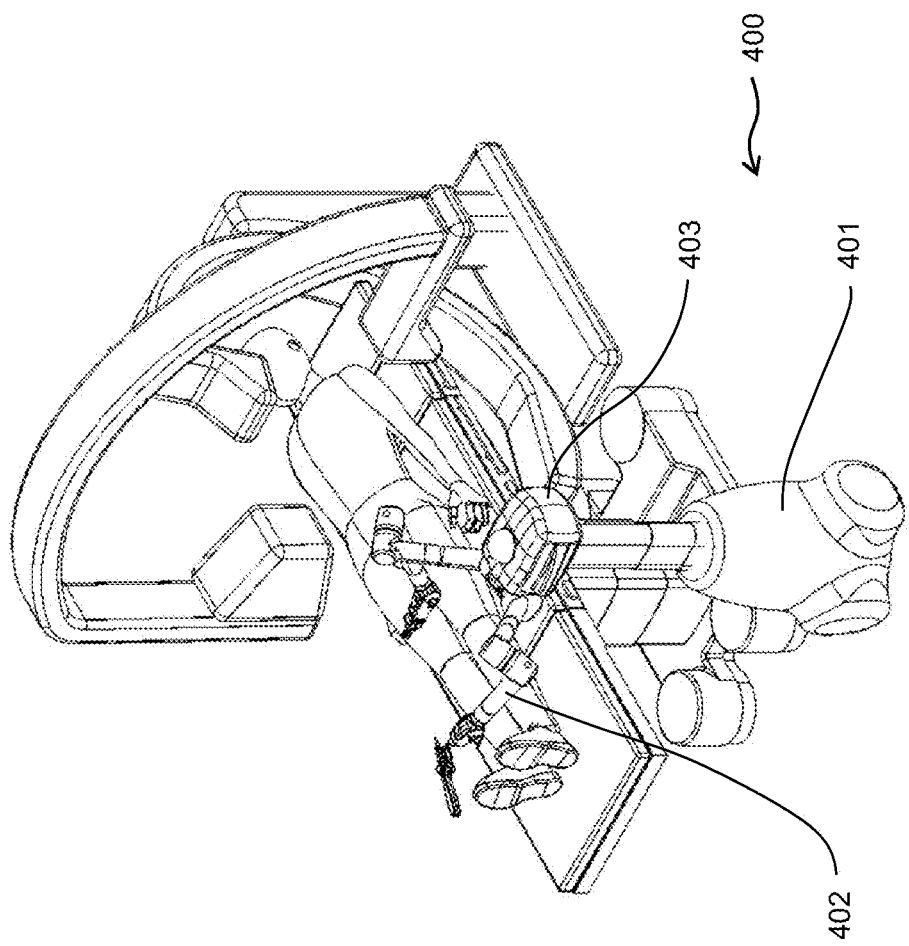
FIG. 33 is a schematic diagram for explaining an operational status of the self-propelled robot.

Furthermore, if the collaborator themselves is absent on the collaborator's side as illustrated in FIG. 33, the self-propelled robot 400 in place of the collaborator can execute actions of the same operation content as the operation content by the expert on a real-time basis.

Figure 34:
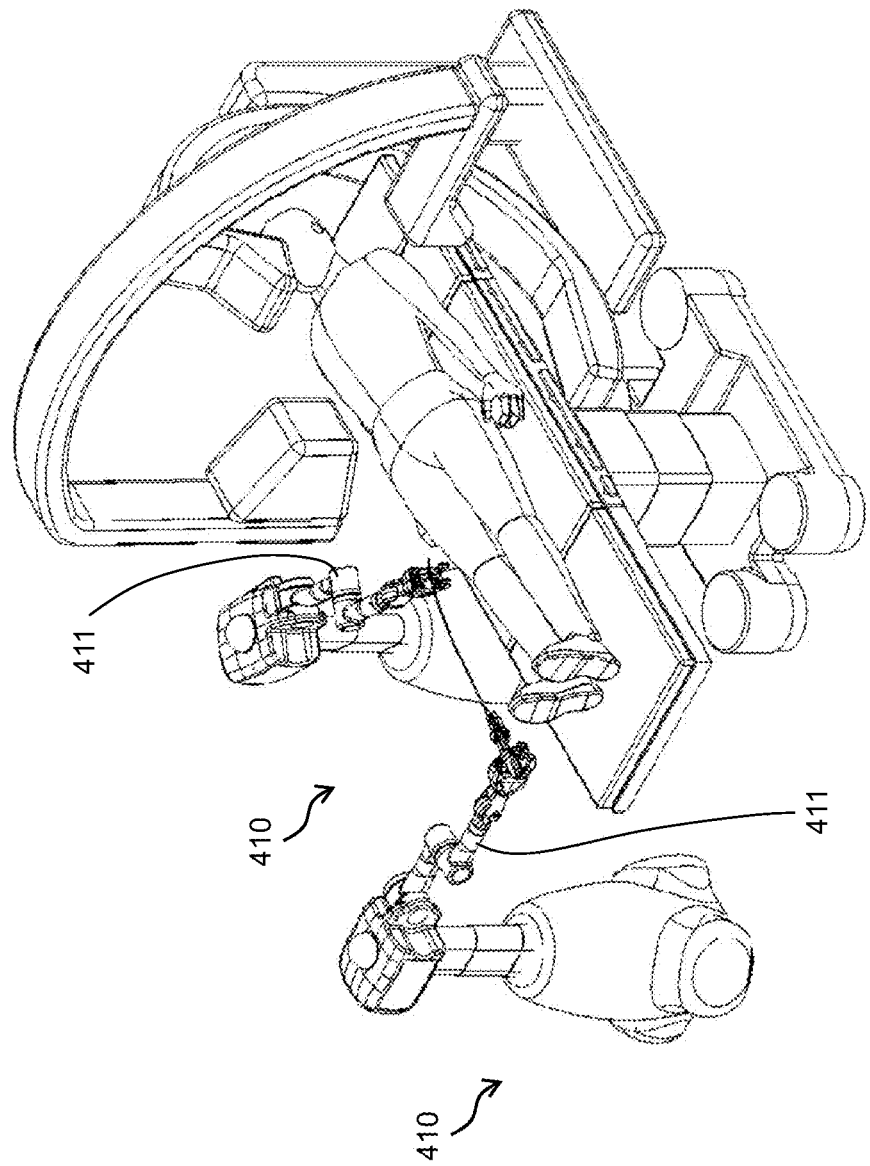
FIG. 34 is a schematic diagram illustrating a state where a self-propelled robot having a single arm unit according to another embodiment is located.

Moreover, as illustrated in FIG. 34, a self-propelled robot 410 having an arm unit 411 which is configured of a single articulated structure may be located for each piece of operation content. Regarding the self-propelled robot 410 having the single arm unit 411, each corresponding arm unit 411 may be caused to execute actions of the operational means according to the expert's operation content on a real-time basis. This self-propelled robot 410 has the same internal structure as that of the aforementioned self-propelled robot 400, except that there is a single arm unit 411.

Figure 35:
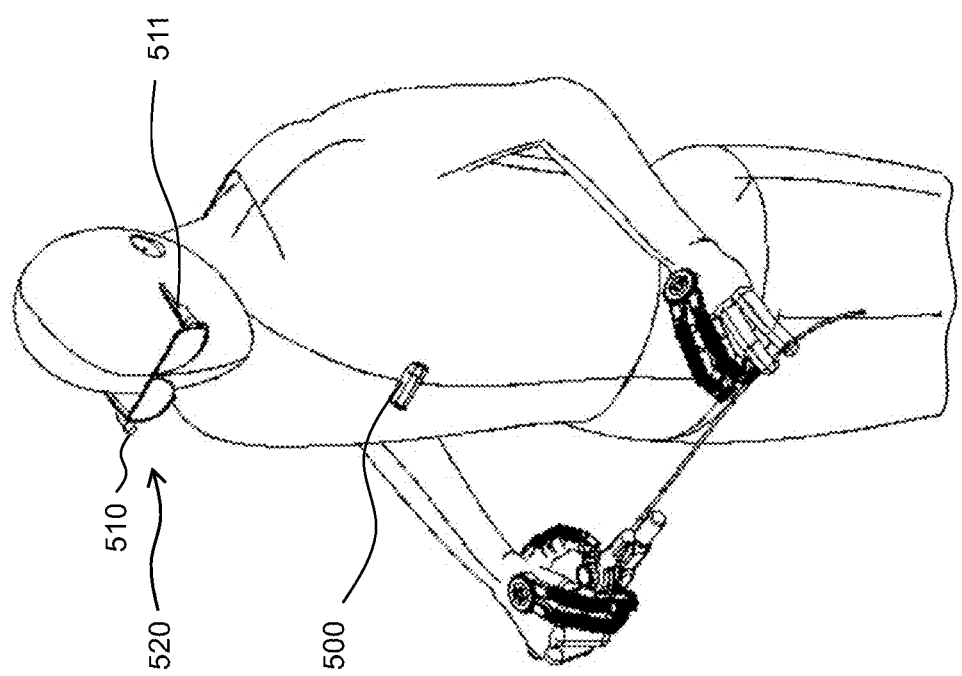
FIG. 35 is a schematic diagram for explaining a wide-angle imaging camera and a spectacle-type sensor which are worn by the expert.

Furthermore, the aforementioned embodiment has described the case where regarding the movement detection unit 14 for the instructing-side information processing apparatus 2 of the interactive information transfer system 1, the plurality of imaging cameras 15A, 15B are installed near the expert as illustrated in FIG. 1; however, the present invention is not limited to this example and a wide-angle imaging camera 500 which is provided at the expert's chest may be used as illustrated in FIG. 35. This wide-angle imaging camera 500 is designed so that it can capture videos of an area around the expert's both hands in a wide range by capturing the videos diagonally downwards from the expert's chest (for example, at 45 degrees downwards relative to the vertical direction).

Moreover, FIG. 1 does not illustrate a specific configuration of the line-of-sight detection unit 13 for the instructing-side information processing apparatus 2, but the visual field detection unit 13 may be configured from a spectacle-type sensor 520 equipped with two imaging sensors 510, 511 as illustrated in FIG. 35. This spectacle-type sensor 520 is located so that one imaging sensor 510 captures videos of the expert's line-of-sight extended end and, at the same time, the other imaging sensor 511 follows the expert's line of sight.

As a result, the expert can always capture a video of the area around their both hands in a wide range and also captures a video of, and follows, their own line-of-sight extended end, so that the collaborator can recognize the expert's operation intervals much better.

REFERENCE SIGNS LIST 1, 200: interactive information transfer system
2: instructing-side information processing apparatus
3, 201: collaborating-side information processing apparatus
4: network
10: instructing-side control unit
11: instructing-side communication unit
12: instructing-side video display unit
13, 202: line-of-sight detection unit
14: movement detection unit
21: collaborating-side communication unit
22: object imaging unit
23: collaborating-side video display unit
24, 205: force displacement transfer unit
25, 100, 120, 206: end effector
30: force sense transfer drive unit
31: signal transformation unit
32: force sense transfer control unit
33: transfer ratio setting unit
40: data management apparatus
50: ambient temperature measurement unit
51: fingertip temperature adjustment unit
60: collaborating-side data display unit
61: instructing-side data display unit
70: ambient sound collection unit
71: ambient sound reproduction unit
80: speaker
81: microphone
101: fingertip back retaining part
102: first linear member
103: second linear member
107: expansion/bending drive unit
108: adduction/abduction drive unit
106, 125: driving unit
121: ring unit
122: inner ring
123: outer ring
124, 354, 381: actuator
130: electrode catheter
140: operation data quantitative extraction unit
141: operation data preferentially reflecting unit
142: operation deviation amount detection unit
143: operation feedback imparting unit
207: ring-shaped light-emitting unit
210: instrument attachment
211, 350, 380: handle retaining part
212: shaft holding part
220: shell housing
221, 352, 382: lever retaining part
222: wire
223: wire drive unit
230: curved contact part
231: holding force adjustment unit
235: force sense feedback imparting unit
240, 280: adjusted amount measurement unit
241: operational status measurement unit
242: synchronous data generation unit
243: difference amount detection unit
250, 300: information transfer system
260, 290: collaborating-side instrument attachment robot
270: operation content reflecting unit
310: operation control unit
320: operational means drive unit
330: adjusted amount feedback measurement unit
340: operational status feedback measurement unit
400, 410: self-propelled robot
500: wide-angle imaging camera
520: spectacle-type sensor
RT: interactive information transfer processing sequence

The invention claimed is:

1. An interactive information transfer method for an instructor to instruct a collaborator in skills regarding specific work while making the instructor and the collaborator mutually exchange information via a network, the interactive information transfer method comprising:
performing on an instructor side,
receiving a video, which includes an object handled by the collaborator, via the network,
displaying the video of the object,
detecting, via a sensor, a position of a line-of-sight of the instructor as line-of-sight position data,
obtaining finger action data corresponding to three-dimensional directional movements of each fingertip of the instructor by setting respective instructor fingertips of the instructor as endpoints,
transmitting the line-of-sight position data and the finger action data on a real-time basis via the network,
performing on a collaborator side,
receiving, via the network, the line-of-sight position data and the finger action data,
capturing the video,
displaying the video and, at a same time, marking and displaying the position of the line-of-sight of the instructor using the line-of-sight position data, and
controlling a wearable device that includes a plurality of end effectors each having an actuator,
wherein the plurality of end effectors are respectively mounted on at least respective collaborator fingertips of the collaborator, and each of the plurality of end effectors includes a wound rotation unit, whose contact face in contact with a collaborator finger, of a respective collaborator fingertip, is wound, in a manner freely rotatable in a rotating direction, with the contact face positioned at a center of a back part of the collaborator finger at any one or more positions between the collaborator fingertip and a first joint, between the first joint and a second joint, and between the second joint and a third joint,
wherein the controlling the wearable device includes:
sending a force, via the plurality of end effectors, to prompt three-dimensional actions to each of a plurality of collaborator fingers while transferring the three-dimensional directional movements based on the finger action data received with respect to each of the plurality of end effectors, respectively driving, via the actuator, each of the plurality of end effectors to guide a respective collaborator finger in a first direction to expand or bend the respective collaborator finger, a second direction to adduct or abduct the respective collaborator finger, and a third direction to rotate the respective collaborator finger, driving, via the actuator, the contact face of the wound rotation unit in contact with the collaborator finger to guide the collaborator finger in the rotating direction by rotating the contact face of the wound rotation unit according to an electromagnetic force or piezoelectric thrust, breaking down the three-dimensional directional movements of each of the endpoints of the instructor into features including a position, speed, acceleration, angular velocity, force, and moment based on the finger action data received, transforming each of the features into action element data, and controlling, based on the action element data, the force sent by the actuator, and transmitting, via the network, the video and physical feedback information of the plurality of end effectors to the instructor side, and the physical feedback information is a transfer result of the wearable device.

2. The interactive information transfer method according to claim 1, further comprising:

capturing videos, via a three-dimensional imaging unit on the instructor side, of the respective endpoints of the instructor from a plurality of different directions; and detecting a pair of gloves with a pattern worn by the instructor, and wherein obtaining the finger action data according to the three-dimensional directional movements of the respective instructor fingertips includes detecting three-dimensional coordinates with respect to the respective endpoints of the instructor from the videos, and the three-dimensional coordinates are centered at a predetermined position located on a front side of the instructor.

3. The interactive information transfer method according to claim 1 further comprises:

variably setting a transfer ratio of the three-dimensional directional movements based on the finger action data with respect to each of the plurality of end effectors in accordance with operations by the collaborator, and transforming the finger action data to the action element data by adjusting the finger action data to the transfer ratio.

4. The interactive information transfer method according to claim 1, wherein each of the plurality of end effectors include a fingertip back retaining part which enters into contact with and is retained at a fingertip back part of the collaborator, and a pair of a first linear member and a second linear member which are respectively pulled out of a top, bottom, right, and left of an end of the fingertip back retaining part;

wherein the method further includes:

driving, via the actuator, the first linear member to guide the respective fingertip to the first direction by moving the first linear member in a direction to push out or pull in the first linear member;

driving, via the actuator, the second linear member to guide the respective fingertip in the second direction by moving the second linear member to right and left directions; and controlling, via the actuator, the first linear member and the second linear member to respectively drive the plurality of end effectors based on the action element data.

5. The interactive information transfer method according to claim 1 further comprising:

vibrating with directivity in three-dimensional directions, via a single vibrating element or a plurality of vibrating elements included in each of the plurality of end effectors which are mounted at a center of a fingertip back part of the collaborator;

driving the vibrating element or the vibrating elements for guiding the vibrating element or the vibrating elements respectively in at least one of the first direction, the second direction, and the third direction; and controlling the vibrating element or the vibrating elements based on the action element data.

6. The interactive information transfer method according to claim 1 further comprises:

emitting light with directivity in three-dimensional directions including at least the first direction, the second direction, or the third direction via a single light emitter or a plurality of light emitters included in each of the plurality of end effectors and which are mounted at a center of a fingertip back part of the collaborator; and controlling the single light emitter or the plurality of light emitters based on the action element data.

7. The interactive information transfer method according to claim 1 further comprising:

extracting adjusted amount data from an operation from among operations performed by an instructing-side work electronic instrument, as instructing-side adjustment data, and the instructing-side work electronic instrument is operated by the instructor by using the respective instructor fingertips when performing the work;

transmitting the instructing-side adjustment data to the instructing-side work electronic instrument via the network; and determining prioritization of the instructing-side adjustment data or collaborator adjusted amount data from a collaborator operation performed by a collaborating-side work electronic instrument based on the instructing-side adjustment data, and wherein the collaborating-side work electronic instrument is operated by the collaborator using the respective collaborator fingertips and has a same configuration as the instructing-side work electronic instrument.

8. The interactive information transfer method according to claim 7, detecting a deviation amount between the instructing-side adjustment data and the collaborator adjusted amount data and on a condition the deviation amount is equal to or larger than a predetermined threshold value, transmitting the deviation amount as operation gap data to the instructing-side work electronic instrument, via the network; and vibrating the instructing-side work electronic instrument according to the deviation amount based on the operation gap data.

9. The interactive information transfer method according to claim 7 further comprising
measuring, via at least an acceleration sensor and a gyro sensor, a three-dimensional posture of an instrument attachment including at least the acceleration sensor and the gyro sensor and being connected to the instructing-side work electronic instrument.

10. The interactive information transfer method according to claim 1 further comprising
measuring an ambient temperature of each of the plurality of end effectors, via an ambient temperature measurement unit included in the wearable device;
transmitting the ambient temperature of each of the plurality of end effectors, as ambient temperature data to the instructor side; and
adjusting a plurality of thermoelectric devices to the ambient temperature using the ambient temperature data, wherein each of the plurality of thermoelectric devices are included in each of a plurality of end sacs that are mounted on each of the respective instructor fingertip of gloves worn by the instructor.

11. The interactive information transfer method according to claim 1, further comprising:
displaying on the collaborator side a list of various types of data related to the object and the position of the line-of-sight of the instructor based on the line-of-sight position data received; and
displaying on the instructor side the list of the various types of data, as a data group.

12. The interactive information transfer method according to claim 1 further comprising:
capturing a position of a collaborator line-of-sight of the collaborator, as collaborator line-of-sight position data;
sending the collaborator line-of-sight position data to the instructor side; and
displaying the position of the collaborator line-of-sight based on the collaborator line-of-sight position data.

13. The interactive information transfer method according to claim 1 further comprising:
collecting, on the collaborator side, sound waves including audible sounds and ultrasonic waves which occur in surroundings of the collaborator in synchronization with capturing the video; and
reproducing the audible sounds and the ultrasonic waves on the instructor side.

14. The interactive information transfer method according to claim 1 further comprising:
collecting, via a microphone, voices of the instructor and transmitting voice data, which is obtained from the microphone, on a real-time basis via the network; and
reproducing, via a speaker on the collaborator side, voices based on the voice data, on a real-time basis.

15. The interactive information transfer method according to claim 14 further comprising:
immediately stopping or resuming the sending of the force to the collaborator, via the plurality of end effectors, according to speech content based on the voice data.

16. The interactive information transfer method according to claim 1 further comprising:
storing a series of action content of the instructor and the collaborator regarding the work by mutually associating the series of action content with each other as instructing-side work data and collaborating-side work data;
sequentially and chronologically extracting feature points from each piece of the action content based on the instructing-side work data and the collaborating-side work data;
analyzing whether each of the feature points extracted corresponds to a skill threshold for the work;
storing the action content including each of the feature points; and
on a condition the skill threshold for the work is met, storing an affirmative analysis result, as skill data.

17. An interactive information transfer method for an instructor to instruct a collaborator in their skills regarding specific work while making the instructor and the collaborator mutually exchange information via a network, the interactive information transfer method comprising:
on a side of the instructor:
detecting a position of a line-of-sight of the instructor within a video of an object handled by the collaborator as line-of-sight position data while receiving and displaying the video via the network, and at a same time detecting finger action data according to three-dimensional directional movements of each fingertip of the instructor by setting respective fingertips of the instructor as endpoints, and
then transmitting the line-of-sight position data and the finger action data to a side of the collaborator via the network on a real-time basis; and
on the side of the collaborator:
marking and displaying the position of the line-of-sight of the instructor based on the line-of-sight position data received while capturing the video, and at a same time imparting a force to prompt three-dimensional actions to each collaborator finger of the collaborator while transferring the three-dimensional directional movements based on the finger action data with respect to each of a plurality of end effectors mounted on each collaborator fingertip of the collaborator, and each of the plurality of end effectors has an actuator,
then transmitting physical feedback information of each of the plurality of end effectors, which is a transfer result of the three-dimensional directional movements, together with the video to the side of the instructor via the network,
breaking down the three-dimensional directional movements of each of the endpoints of the instructor into features including a position, speed, acceleration, angular velocity, force, and moment based on the finger action data received,
transforming each of the features into action element data, and
controlling, based on the action element data, a force sent to the actuators, so as to guide each of the plurality of end effectors in a first direction to expand or bend a respective collaborator finger, a second direction to adduct or abduct the respective collaborator finger, and a third direction to rotate the respective collaborator finger.

18. The interactive information transfer method according to claim 17, wherein on the side of the instructor,
detecting the finger action data, according to the three-dimensional directional movements of the respective fingertips of the instructor, further includes detecting three-dimensional coordinates with respect to respective endpoints of the instructor from a video capturing result of videos of the instructor captured from a plurality of different directions, and the three-dimensional coordinates are centered at a predetermined position located on a front side of the instructor.

19. The interactive information transfer method according to claim 17,
wherein on the side of the collaborator, setting a transfer ratio of the three-dimensional directional movements based on the finger action data with respect to each of the plurality of end effectors in accordance with an operation performed by the collaborator and transforming the finger action data to the action element data by adjusting the finger action data to the transfer ratio.

20. The interactive information transfer method according to claim 17,
wherein on the side of the collaborator, an ambient temperature of each of the plurality of end effectors is measured as ambient temperature data is transmitted to the side of the instructor via the network; and
wherein on the side of the instructor, a thermoelectric device mounted on each of a plurality of end sacs attached to gloves on the respective fingertips of the instructor is adjusted to the ambient temperature using the ambient temperature data.

21. The interactive information transfer method according to claim 17,
wherein a list of various types of data related to the object is displayed near the video on the side of the collaborator and, at a same time on the side of the instructor, the list of the various types of data, as a data group, are displayed; and
wherein the position of the line-of-sight of the instructor based on the line-of-sight position data received is displayed on the side of the collaborator.

22. The interactive information transfer method according to claim 17,
wherein a position of a collaborator line-of-sight of the collaborator, is detected as collaborator line-of-sight position data and the collaborator line-of-sight position data is sent to the side of the instructors; and
the position of the collaborator line-of-sight based on the collaborator line-of-sight position data received is displayed on the side of the instructor.

23. The interactive information transfer method according to claim 17,
wherein on the side of the collaborator, sound waves including audible sounds and ultrasonic waves which occur in surroundings of the collaborator are collected in synchronization with capturing of the video and are transmitted to the side of the instructor; and
wherein on the side of the instructor, the audible sounds and the ultrasonic waves are reproduced.

24. The interactive information transfer method according to claim 17,
wherein on the side of the instructor, voice data obtained by collecting voices of the instructor is transmitted on a real-time basis to the side of the collaborator via the network; and
wherein on the side of the collaborator, the voices based on the voice data received are reproduced on a real-time basis.

25. The interactive information transfer method according to claim 24,
wherein on the side of the collaborator, imparting the force to the collaborator is immediately stopped or resumed according to speech content based on the voice data received from the side of the instructor.

26. The interactive information transfer method according to claim 17,
wherein a series of action content of the instructor and the collaborator regarding the work is stored by mutually associating the series of the action content with each other as instructing-side work data and collaborating-side work data;
wherein feature points of each piece of the action content are sequentially and chronologically extracted from each piece of the action content based on the instructing-side work data and the collaborating-side work data;
wherein whether each of the feature points extracted corresponds to a skill threshold for the work is analyzed; and
wherein the action content including each of the feature points is stored, and on a condition the skill threshold for the work is met, an affirmative analysis result is stored as skill data.

27. The interactive information transfer method according to claim 26, comprising:
sequentially reading the skill data with a predetermined relevance with each piece of the action content from a skill data storage unit when the collaborator executes the series of the action content with regard to different work that is determined to be the work;
sequentially estimating whether each piece of the action content of the collaborator becomes chronologically increasingly likely to match action content that meets the skill threshold; and
instructing the collaborator by reflecting the action content corresponding to the skill threshold in the action content executed by the collaborator on a real-time basis based on a result of the estimation.

* * * * *